(12) United States Patent
Gorodetsky et al.

(10) Patent No.: US 10,899,711 B2
(45) Date of Patent: Jan. 26, 2021

(54) QUINOLINES, POLYQUINOLINES, MOLECULAR SEGMENTS OF FULLERENES AND GRAPHENE NANORIBBONS, AND GRAPHENE NANORIBBONS AND METHODS OF THEIR SYNTHESIS

(71) Applicant: The Regents of the University of California, Oakland, CA (US)

(72) Inventors: Alon Gorodetsky, Irvine, CA (US); David Joshua Dibble, Santa Ana, CA (US); Mehran Umerani, Irvine, CA (US); Amir Mazaheripour, Irvine, CA (US); Young Suk Park, Huntington Beach, CA (US); Anthony Burke, Fountain Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/538,180

(22) PCT Filed: Dec. 31, 2015

(86) PCT No.: PCT/US2015/068339
§ 371 (c)(1),
(2) Date: Jun. 20, 2017

(87) PCT Pub. No.: WO2016/109830
PCT Pub. Date: Jul. 7, 2016

(65) Prior Publication Data
US 2017/0362179 A1 Dec. 21, 2017

Related U.S. Application Data

(60) Provisional application No. 62/135,579, filed on Mar. 19, 2015, provisional application No. 62/098,512, filed on Dec. 31, 2014.

(51) Int. Cl.
| | | |
|---|---|---|
| C07D 215/06 | (2006.01) | |
| C07D 401/14 | (2006.01) | |
| C07D 215/12 | (2006.01) | |
| C07D 215/04 | (2006.01) | |
| C07D 221/12 | (2006.01) | |
| C08L 79/02 | (2006.01) | |
| C07D 215/18 | (2006.01) | |
| C07C 5/02 | (2006.01) | |
| C07D 221/06 | (2006.01) | |
| C08G 18/78 | (2006.01) | |
| C08G 73/06 | (2006.01) | |
| C01B 32/152 | (2017.01) | |
| C01B 32/182 | (2017.01) | |

(52) U.S. Cl.
CPC .............. *C07D 215/06* (2013.01); *C07C 5/02* (2013.01); *C07D 215/04* (2013.01); *C07D 215/12* (2013.01); *C07D 215/18* (2013.01); *C07D 221/06* (2013.01); *C07D 221/12* (2013.01); *C07D 401/14* (2013.01); *C08G 18/7862* (2013.01); *C08G 73/0688* (2013.01); *C08L 79/02* (2013.01); *C01B 32/152* (2017.08); *C01B 32/182* (2017.08)

(58) Field of Classification Search
CPC .. C07D 215/06; C07D 215/04; C07D 215/12; C07D 215/18; C08L 79/02
See application file for complete search history.

(56) References Cited

U.S. PATENT DOCUMENTS

2011/0282065 A1 11/2011 Che

FOREIGN PATENT DOCUMENTS

WO 2016109830 7/2016

OTHER PUBLICATIONS

Kouznetsov, Tetrahedron, 2009, vol. 65, 2721-2750. (Year: 2009).*
Gandeepan, Asian J Org Chem, vol. 3, 2014, 303-308. (Year: 2014).*
International Preliminary Report on Patentability for International Application PCT/US2015/068339, Report dated Jul. 4, 2017, dated Jul. 13, 2017, 7 Pgs.
International Search Report and Written Opinion for International Application No. PCT/US2015/068339, Search completed Jul. 20, 2016, dated Aug. 26, 2016, 10 Pgs.
International Tables for Crystallography 1992, vol. C., Dordrecht: Kluwer Academic Publishers, 1020 pgs. (presented in six parts).
Agrawal et al., "Electrochemical Properties and Electronic Structures of Conjugated Polyquinolines and Polyanthrazolines", Chem. Mater., 1996, vol. 8, No. 2, pp. 579-589.
Agrawal et al., "Synthesis and Processing of Heterocyclic Polymers as Electronic, Optoelectronic, and Nonlinear Opticals. 2. New Series of Conjugated Rigid-Rod Polyquinolines and Polyanthrazolines", Macromolecules, 1993, vol. 26, No. 5, pp. 895-905.
Alberico et al., "Aryl-Aryl Bond Formation by Transition-Metal-Catalyzed Direct Arylation", Chem. Rev., 2007, vol. 107, pp. 174-238.
Anthony, "Functionalized Acenes and Heteroacenes for Organic Electronics", Chem. Rev., 2006, vol. 106, pp. 5028-5048.
Anthony, "Hohere Acene: vielseitige organische Halbleiter", Angew. Chem., 2008, vol. 120, pp. 460-492.
Anthony, "The Larger Acenes: Versatile Organic Semiconductors", Angew. Chem. Int. Ed., 2008, vol. 47, pp. 452-483.

(Continued)

Primary Examiner — D Margaret M Seaman
(74) Attorney, Agent, or Firm — KPPB LLP

(57) ABSTRACT

Quinolines, polyquinolines, polybenzoquinolines, molecular segments of fullerenes and graphene nanoribbons, and graphene nanoribbons and processes for producing such materials are provided. The processes utilize a form of an aza-Diels-Alder (Povarov) reaction to first form quinolines and/or polyquinolines. In some such embodiments polyquinolines thus produced are used to form graphene nanoribbon precursors, and molecular segments and graphene nanoribbons. In many such embodiments the graphene nanoribbon precursors are formed from polybenzoquinolines.

47 Claims, 74 Drawing Sheets

(56) References Cited

OTHER PUBLICATIONS

Anthony et al., "n-Type Organic Semiconductors in Organic Electronics", Advanced Materials, 2010, vol. 22, pp. 3876-3892.
Araujo et al., "Defects and impurities in graphene-like materials", Mater. Today, 2012, vol. 15, pp. 98-109.
Atherton et al., "Diels-Alder reactions of anthracene, 9-substituted anthracenes and 9,10-disubstituted anthracenes", Tetrahedron, 2003, vol. 59, pp. 9039-9057.
Bailey, "Step-Growth Polymerisations", Step Growth Polymerization; Marcel Dekker: New York, 1972; vol. 3, pp. 279-332 (summary only).
Bangcuyo et al., "Quinoline-Containing, Conjugated Poly(aryleneethynylene)s: Novel Metal and H+-Responsive Materials", Macromolecules, 2002, vol. 35, pp. 1563-1568.
Bard et al., "Electrochemical Methods: Fundamentals and Applications", 2nd ed., Wiley, New York, 2000, 850 pgs. (presented in six parts).
Batra et al., "Probing the mechanism for graphene nanoribbon formation on gold surfaces through X-ray spectroscopy", Chemical Science, Jul. 31, 2014, vol. 5, pp. 4419-4423.
Beever et al., "Synthesis and Thermal Properties of Aromatic Polymers Containing 3,6-Quinoline Units in the Main Chain", Macromolecules, Nov.-Dec. 1979, vol. 12, vol. 6, pp. 1033-1038.
Benniston et al., "Simultaneous fluorescence and redox modulation in an irreversible photochrome based on a strained dibenzoacridinium cation", Organic Bimolecular Chemistry, 2006, vol. 4, pp. 3886-3888.
Berger et al., "Synthese Stickstoff-dotierter Zickzacllamtem: Dibenzo-9a-azaphena-len als molkularer Buastein", Angew. Chem. 2014, vol. 126, pp. 10688-10692.
Berger et al., "Synthesis of Nitrogen-Doped ZigZag-Edge Peripheries: Dibenzo-9a-azaphenalene as Repeating Unit", Angew. Chem. Int. Ed., 2014, vol. 53, pp. 10520-10524.
Bilici et al., "Facile and Regioselective synthesis of poly(5-hydroxyquinoline)", Reactive & Functional Polymers, 2011, vol. 71, pp. 675-683, available online Mar. 30, 2011.
Bilici et al., "Tunable Multicolor Emission in Oligo(4-hydroxyquinoline)", J. Phys. Chem. C, Aug. 28, 2012, vol. 116, pp. 19934-19940.
Blankenburg et al., "Intraribbon Heterojunction Formation in Ultranarrow Graphene Nanoribbons", ACS Nano, 2012, vol. 6, No. 3, pp. 2020-2025, published online Feb. 10, 2012.
Braude et al., "Hydrogen Transfer. Part XVI. Dihydrides of Nitrogenous Heterocycles as Hydrogen Donors", J Chem. Soc., 1960, pp. 3249-3257.
Broch et al., "Synthesis and in vitro antiproliferative activities of quinoline derivatives", European Journal of Medicinal Chemistry, 2010, vol. 45, pp. 1657-1662, available online Jan. 14, 2010.
Bronner et al., "Aligning the Band Gap of Graphene Nanoribbons by Monomer Doping", Angew. Chem. Int. Ed. 2013, 52, 4422-4425; Angew. Chem. 2013, 125, 4518-4521.
Bronner et al., "Electronic structure changes during the surface-assisted formation of a graphene nanoribbon", The Journal of Chemical. Physics, 2014, vol. 140, pp. 024701-1-024701-7.
Buckle, "2,3-Dichloro-5,6-dicyano-1,4-benzoquinone", Encyclopedia of Reagents for Organic Synthesis, John Wiley & Sons, Ltd., Oct. 15, 2005, Retrieved from the Internet http://onlinelibrary.wiley.com/doi/10.1002/047084289X.rd114.pub2/pdf on Oct. 1, 2014, 12 pgs.
Buckle et al., "Chloranil", e-EROS Encyclopedia of Reagents for Organic Synthesis, John Wiley & Sons, 2001, pp. 1-2, http://onlinelibrary.wiley.com/doi/10.1002/047084289X.rc057/pdf.
Bunz, "The Larger Linear N-Heteroacenes", Accounts of Chemical Research, May 13, 2015, vol. 48, pp. 1676-1686.
Cai et al., "Atomically precise bottom-up fabrication of graphene nanoribbons", Nature, Jul. 2010, vol. 466, pp. 470-473.
Cai et al., "Graphene nanoribbon heterojunctions", Nature Nanotechnology, Nov. 2014, vol. 9, pp. 896-900, published online Sep. 7, 2014.
Cardona et al., "Electrochemical Considerations for Determining Absolute Frontier Orbital Energy Levels of Conjugated Polymers for Solar Cell Applications", Advanced Materials, 2011, vol. 23, pp. 2367-2371.
Cervantes-Sodi et al., "Edge-functionalized and substitutionally doped graphene nanoribbons: Electronic and spin properties", Physical. Review, B, 2008, vol. 77, pp. 165427.1-165427.13.
Chen et al., "Die chemische Synthese von Nanographen, Graphen-Nanobandern und Graphen-Schichten", Angew. Chem., 2012, vol. 124, pp. 7758-7773.
Chen et al., "Diindeno[1,2-g:1',2'-s]rubicene: all-carbon non-fullerene electron acceptor for efficient bulk-heterojunction organic solar cells with high open-circuit voltage", RSC Adv., 2015, vol. 5, pp. 3381-3385.
Chen et al., "From Nanographene and Graphene Nanoribbons to Graphene Sheets: chemical synthesis", Angew. Chem. Int., 2012, vol. 51, pp. 7640-7654.
Chen et al., "Graphene nano-ribbon electronics", Physica E, 2007, vol. 40, pp. 223-232, available online Jun. 16, 2007.
Chen et al., "Palladium (II)-Catalyzed C—H Activation/C—C Cross-Coupling Reactions: Versatility and Practicality", Angew. Chem. Int. Ed., 2009, vol. 48, pp. 5094-5115.
Chen et al., "Polyquinolines containing both spirobifluorene and cardofluorene units: Synthesis and characterization", J Polym. Sci., Part A: Polym. Chem., 2004, vol. 42, pp. 3314-3322.
Chen et al., "Supramolecular Self-Assembly of Three-Dimensional Nanostructures and Microstructures: Microcapsules from Electroactive and Photoactive Rod-Coil-Rod Triblock Copolymers", Macromolecules, 2000, vol. 33, No. 13, pp. 4610-4612.
Chen et al., "Tuning the saturated red emission: synthesis, electrochemistry and photophysics of 2-arylquinoline based iridium (III) complexes and their application in OLEDs", Journal of Materials Chemistry, 2006, vol. 16, pp. 3332-3339, first published as an Advance Article on the web Jul. 14, 2006.
Chiang et al., "Real-space imaging of molecular structure and chemical bonding by single-molecule inelastic tunneling probe", Science, May 23, 2014, vol. 344, Issue 6186, pp. 885-888.
Clar et al., "2 : 3-Benzorubicene, Rubicene, and their Derivatives", J. Chem. Soc., 1958, pp. 942-946.
Clar et al., "Aromatic Hydrocarbons. Part LXVI. Diperinaphthylene-anthracenes", J. Chem. Soc., 1954, vol. 75, No. 2667, pp. 1108-1111.
Clar et al., "Die Synthese des 1.9, 5.10-Di-[peri-naphthylen]-anthracens (Zur Kenntnis mehrkernigher aromathischer Kohlenwasserstoffe und ihrer Abkommlinge, 19. Mitteil.)", Ber. Dtsch. Chem. Ges. A/B, 1932, vol. 65, pp. 1521-1525.
Claridge et al., "Chapter 8—Correlations through space: The nuclear Overhauser effect", Tetrahedron Organic Chemistry Series, 2009, vol. 27, pp. 247-302 (abstract only).
Lu et al., "Synthesis, characterization, and biological activities of two Cu(II) and Zn(II) complexes with one polyquinoline ligand", Spectrochimica Acta Part A, 2014, vol. 130, pp. 390-396, available online Apr. 18, 2014.
Luca et al., "Catalysis by electrons and holes: formal potential scales and preparative organic electrochemistry", Organic Chemistry Frontiers, Jul. 2015, vol. 2, No. 7, pp. 823-848.
Lv et al., "Towards new graphene materials: Doped graphene sheets and nanoribbons", Material Letters, 2012, vol. 78, pp. 209-218.
Ma et al., "A Convenient Modular Approach of Functionalizing Aromatic Polyquinolines for Electrooptic Devices", Chem. Mater., 1999, vol. 11, pp. 2218-2225.
Ma et al., "Recent Progress and Challenges in Graphene Nanoribbon Synthesis", ChemPhysChem, 2013, vol. 14, pp. 47-54.
Ma et al., "Versatile synthetic Approach to Nonlinear Optical Side-Chain Aromatic Polyquinolines with Large Second-Order Nonlinearity and Thermal Stability", Macromolecules, 1998, vol. 31, pp. 4049-4052.
Maiti et al., "One pot imino Diels-Alder reaction for the synthesis of 3-aryl-3,4-dihydro-benzol[F[quinoline derivatives catalyzed by antimony trichloride", Tetrahedron Letters, 2013, vol. 54, pp. 2920-2923.
Marco-Contelles et al., "Recent Advances in the Fieidländer Reaction", Chem. Rev., 2009, vol. 109, pp. 2652-2671.

(56) References Cited

OTHER PUBLICATIONS

McCartney et al., "The asymmetric Heck and related reactions", Chem. Soc. Rev., 2011, vol. 40, pp. 5122-5150.
McGlacken et al., "Recent advances in aryl-aryl bond formation by direct arylation", Chemical Society Reviews, 2009, vol. 38, pp. 2447-2464, first published as an Advance Article on the web May 22, 2009.
Meyer et al., "Experimental analysis of charge redistribution due to chemical bonding by high-resolution transmission electron microscopy", Nature Materials, 2011, vol. 10, pp. 205-215, published online Jan. 16, 2011.
Meyers et al., "Complete Intramolecular Transfer of a Central Chiral Element to an Azial Chiral Element. Oxidation of (S)-4-Naphthyldihydroquinolines ot (S)-3-Naphthylquinolines", Journal of American Chemical Society, 1984, vol. 106, pp. 1135-1136.
Mi et al., "New polycyclic aromatic hydrocarbon dopants for red organic electroluminescent devices", Journal of Materials Chemistry, 2002, vol. 12, pp. 1307-1310.
Miao, "Polycyclic Arenes and Heteroarenes", Wiley-VCH, Weinhein, 2015, 344 pgs. (presented in three parts).
Mohebbi et al., "Electron-Accepting Dithiarubicene (Emeraldicene) and Derivatives Prepared by Unprecedented Nucleophilic Hydrogen Substitution by Alkyllithium Reagents", Chemistry A European Journal, 2011, vol. 17, pp. 2642-2646.
Mojica et al., "Synthesis of fullerenes", Journal of Physical Organic Chemistry, 2013, vol. 26, pp. 526-539, published online Apr. 29, 2013.
Moszynski et al., "Iron nitriding and reduction of iron nitrides in nanocrystalline Fe—N system", Materials Letters, 2012, vol. 78, pp. 32-34.
Mullen, "Evolution of Graphene Molecules: Structural and Functional Complexity as Driving Forces behind Nanoscience", ACS Nano, 2014, vol. 8, No. 7, pp. 6531-6541, published online Jul. 11, 2014.
Nalwa et al., "Polyquinoline/bismaleimide composites as high-temperature-resistant materials", Applied Physical Letters, Mar. 16, 1998, vol. 72, No. 11, pp. 1311-1313.
Narita et al., "Bottom-Up synthesis of Chemically Precise Graphene Nanoribbons", The Chemical Record, 2015, vol. 15, pp. 295-309, published online Nov. 21, 2014.
Narita et al., "Bottom-Up Synthesis of Liquid-Phase-Processable Graphene Nanoribbons with Near-Infrared Absorption", ACS Nano, 2014, vol. 8, pp. 11622-11630.
Narita et al., "New advances in nanographene chemistry", Chem. Soc. Rev., 2015, vol. 44, pp. 6616-6643.
Narita et al., "Synthesis of structurally well-defined and liquid-phase-processable graphene nanoribbons", Nature Chemistry, Feb. 2014, vol. 6, pp. 126-132.
Neto et al., "The electronic properties of graphene", Rev. Mod. Phys., 2009, vol. 81, pp. 109-162, arXiv:0709.1163.
Nguyen et al., "General Method for the Preparation of Functionalized Fluorinated Phenyl Alkynes", Journal of Organic Chemistry, 1993, vol. 58, pp. 7368-7376. p. 7368, col. 2, first reaction; p. 7370, col. 2, first reaction.
Nolde et al., "Synthesis and Modification of Terrylenediimides as High-Performance Fluorescent Dyes", Chem. Eur. J, 2005, vol. 11, pp. 3959-3967.
Parker et al., "Efficient blue electroluminescence from a fluorinated polyquinoline", Applied Physics Letters, Sep. 5, 1994, vol. 65, pp. 1272-1274, doi: 10.1063/1.112092.
Parsons et al., "Use of intensity quotients and differences in absolute structure refinement", Acta Crystallographica, Section B, Structural Science, Crystal Engineering and Materials., 2013, vol. B69, pp. 249-259.
Pascual et al., "Palladium catalyzed arylation for the synthesis of polyarenes", Organic & Biomolecular Chemistry, 2007, vol. 5, pp. 2727-2734.
Petrukhina et al., "Fragments of Fullerenes and Carbon Nanotubes", Angew. Chem. Int. Ed. 2012, vol. 51, p. 6820.

Pinardi et al., "Tailored Formation of N-Doped Nanoarchitectures by Diffusion-Controlled on-Surface (Cyclo) Dehydrogenation of Heteroaromatics", ACS Nano, 2013, vol. 7, pp. 3676-3684.
Polaske et al., "Thermally Reversible Dendronized Linear AB Step-Polymers via "Click" Chemistry", Macromolecules, Apr. 8, 2011, vol. 44, pp. 3203-3210.
Povarov, "αβ-Unsaturated Ethers and Their Analogues in Reactions of Diene Synthesis", Russian Chemical Reviews, Sep. 1967, vol. 36, No. 9, pp. 656-670.
Prachayasittikul et al., "8-Hydroxyquinolines: a review of their metal chelating properties and medicinal applications", Drug Des, Dev. Ther., 2013, vol. 7, pp. 1157-1178.
Pretsch et al., "Structure Determination of Organic Compounds", Springer-Verlag: New York, 2000, 443 pgs.
Pschirer et al., "Pentarylene- and Hexarylenebis(dicarboximide)s: Near-Infrared-Absorbing Polyaromatic Dyes", Angew Chem Int. Ed., 2006, vol. 45, pp. 1401-1404.
Reddy et al., "Dies-Alder reaction of acenes with singlet and triplet oxygen-theoretical study of two-state reactivity", Chem. Commun., 2006, pp. 1179-1181.
Rempala et al., "Investigation of the Mechanism of the Intramolecualr School Reaction of Contiguous Phenylbenzenes", J. Org. Chem., 2006, vol. 71, pp. 5067-5081.
Rohlmann et al., "Iron-Catalyzed Oxidative Tandem Reactions with TEMPO Oxoammonium Salts: Synthesis of Dihydroquinazolines and Quinolines", J. Org. Chem., May 24, 2013, vol. 78, pp. 6050-6064.
Ruffieux et al., "Electronic Structure of Atomically Precise Graphene Nanoribbons", ACS Nano, 2012, vol. 6, No. 8, pp. 6930-6935, published online Aug. 1, 2012.
Rusanov et al., "Polyquinolines and polyanthrazolines: synthesis and properties", Russian Chemical Reviews, 2005, vol. 74, No. 7, pp. 671-683.
Sakaguchi et al., "Width-Controlled Sub-Nanometer Graphene Nanoribbon Films Synthesized by Radical-Polymerized Chemical Vapor Deposition", Advanced Materials, 2014, vol. 26, pp. 4134-4138.
Sakamoto et al., "A "Green" Route to Perylene Dyes: Direct Coupling Reactions of 1,8-Naphthalimide and Related Compounds under Mild Conditions Using a "New" Base Complex Reagent, t/BuOK/DBN", J. Org. Chem., 2001, vol. 66, pp. 94-98.
Sarmah et al., "Microwave-Promoted Efficient Synthesis of Benzo[h]quinolines by Solvent-Free Three-Component Imino-Diels-Alder Reaction under One-Pot Conditions", Synlett, 2013, vol. 24, pp. 2245-2248.
Saugues et al., "Synthesis and biological activities of polyquinoline derivatives: New Bcl-2 family protein modulators", European Journal of Medicinal Chemistry, 2012, vol. 57, pp. 112-125, available online Sep. 17, 2012.
Schiros et al., "Connecting Dopant Bond Type with Electronic Structure in N-Doped Graphene", Nano Letters, Jun. 29, 2012, vol. 12, pp. 4025-4031.
Schlüter, "Diels-Alder Ladder Polymers: Synthesis and Aromatization", Materials Science and Technology, Wiley-VCH Verlag GmbH, Weinheim, 2008, pp. 460-483.
Scholl et al., "Abspaltung aromatisch gebundenen Wassserstoffs und Verknupfung aromatisher Kerne durch Aluminiumchlorid", Justus Liebigs Ann. Chem., 1912, vol. 394, pp. 111-177.
Schwab et al., "Structurally Defined Graphene Nanoribbons with High Lateral Extension", Journal of the American Chemical Society, Oct. 19, 2012, vol. 134, pp. 18169-18172.
Schwierz, "Graphene transistors", Nature Nanotechnology, Jul. 2010, vol. 5, pp. 487-496.
Scott, "Methoden zur chemischen Synthese vol Fullerenen", Angew. Chem., 2004, vol. 116, pp. 5102-5116.
Scott, "Methods for the Chemical Synthesis of Fullerenes", Angew. Chem. Int. Ed., 2004, vol. 43, pp. 4994-5007.
Scott, "Polycyclic Aromatic Hydrocarbon Bowls, Baskets, Balls, and Tubes: Challenging Trgets for Chemical Synthesis", Polycyclic Aromatic Compounds., 2010, vol. 30, pp. 247-259.
Shen et al., "Synthesis, charge transport and device applications of graphene nanoribbons", Synthetic Metals, 2015, vol. 210, pp. 109-122.

(56) References Cited

OTHER PUBLICATIONS

Siemssen et al., "Synthesis and Photophysics of New Donor-Acceptor Copolymers Based on Fluorene and Phenylquinolines", Molecular Crystal and Liquid Crystals, 2006, vol. 462, No. 1, pp. 159-167.
Delhaes, "Carbon-based Solids and Materials", John Wiley & Sons, Inc., Hoboken, 2011, 645 pgs. (presented in five parts).
Deng et al., "Toward N-Doped Graphene via Solvothermal Synthesis", Chemistry of Materials, Jan. 26, 2011, vol. 23, pp. 1188-1193.
Denk et al., "Exciton-dominated optical response of ultra-narrow graphene nanoribbons", Nature Communications, 2014, vol. 5, 4253, DOI 10.1038/ncomms5253, 7 pgs.
Dennler et al., "Polymer-Fullerene Bulk-Heterojunction Solar Cells", Advanced Materials, 2009, vol. 21, pp. 1323-1338.
Dibble et al., "An Aza-Diels-Alder Route to Polyquinolines", Macromolecules, 2015, vol. 48, pp. 557-561.
Dibble et al., "Synthesis of Polybenzoquinloines as Precursors for Nitrogen-Doped Graphene Nanoribbons", Agnew. Chem. Int. Ed., 2015, vol. 54, pp. 5883-5887.
Dibble et al., "Synthesis of Polybenzoquinolines as Precursors for Nitrogen-Doped Graphene Nanoribbons", Angew. Chem. 2015, vol. 127, pp. 5981-5985.
Dossel et al., "Graphene Nanoribbons by Chemists: Nanometer-Sized, Soluble, and Defect Free", Angew. Chem. Int. Ed. 2011, vol. 123, pp. 2588-2591.
Dossel et al., "Graphene Nanoribbons by Chemists: Nanometer-Sized, Soluble, and Defect-Free", Angew. Chem. Int. Ed., 2011, vol. 50, pp. 2540-2543.
Dutta et al., "Novel properties of graphene nanoribbons: a review", Journal of Materials Chemistry, 2010, vol. 20, pp. 8207-8223.
Echavarren et al., "Palladium-Catalyzed Intramolecular Arylation Reaction: Mechanism and Application for the synthesis of Polyarenes", Synlett, 2003, vol. 5, pp. 585-597.
Fedorov et al., "Observation of a universal donor-dependent vibrational mode in graphene", Nature Communications, Feb. 6, 2014, vol. 5, 3257, pp. 1-8.
Ferrari et al., "Science and technology roadmap for graphene, related tow0dimensional crystals, and hybrid systems", Nanoscale, 2015, vol. 7, pp. 4598-4810.
Fittig et al., "Ueber das Phenanthren, einen neucn Kohlenwasserstoff in Steinkohlenther", Justus Liebigs Ann. Chem. 1873, vol. 166, pp. 361-382.
Fryer et al., "Quinazolines and 1,4-Benzodiazepines. XLV. 1,4, Benzodiazepines from 4-Isoquinolones", J Org. Chem., 1970, vol. 35, No. 7, pp. 2455-2459.
Gao et al., "Development of n-type organic semiconductors for thin film transistors: a viewpoint of molecular design", J. Mater. Chem. C, 2014, vol. 2, pp. 3099-3117.
Geim et al., "Carbon Wonderland", Scientific American, Apr. 2008, pp. 90-97.
Geim et al., "The rise of graphene", Nature Materials, Mar. 2007, vol. 6, pp. 183-191.
Georgakilas et al., "Broad Family of Carbon Nanoallotropes: Classification, Chemistry, and Applications of Fullerenes, caron Dots, Nanotubes, Graphene, Nanodiamonds, and Combined Superstructures", Chemical Reviews, May 27, 2015, vol. 115, pp. 4744-4822.
Gorodetsky et al., "Reticulated Heterojunctions for Photovoltaic Devices", Angew. Chem. Int. Ed., 2010, vol. 49, pp. 7909-7912.
Grzybowski et al., "Comparison of Oxidative Aromatic Coupling and the Scholl Reaction", Angew. Chem. Int. Ed., 2013, vol. 52, pp. 9900-9930.
Grzybowski et al., "Oxidative aromastiche Kupplung and Scholl-Reaktion im Vergleich", Angew. Chem., 2013, vol. 125, pp. 10084-10115.
Han et al., "Selective Aerobic Oxidation of Alcohols to Aldehydes, Carboxylic Acids, and Imines Catalyzed by a Ag—NHC Complex", Organic Letters, 2014, vol. 16, pp. 3428-3431.
Heck, "Palladium-Catalyzed Vinylation of Organic Halides", Organic Reaction, 1982, vol. 27, pp. 345-390.

Hicks et al., "A wide-bandgap metal-semiconductor-metal nanostructure made entirely from graphene", Nature Physics, Jan. 2013, vol. 9, pp. 49-54, published online Nov. 18, 2012.
Holtrup et al., "Terrylenimides: New NIR Fluorescent Dyes", Chem. Eur. J., 1997, vol. 3, No. 2, pp. 219-225.
Huisgen et al., "Diphenyl-Nitrilimin und Seine 1.3-Dipolaren Additionen an Alkene und Alkine", Tetrahedron, 1962, vol. 17, pp. 3-29.
Hummelen et al., "Heterofullerenes", Topics in Current Chemistry, 1999, vol. 199, pp. 93-134.
Ito et al., "Benzene-fused Azacorannulene Bearing an Internal Nitrogen Atom", Angew. Chem. Int. Ed., 2015, vol. 54, pp. 7256-7260.
Ito et al., "Benzene-Fused Azacorannulene Bearing an Internal Nitrogen Atom", Angew. Chem., 2015, vol. 127, pp. 7364-7368.
Jegou et al., "Highly Fluorescent Poly(arylene ethynylene)s Containing Quinoline and 3-Alkylthiophene", Macromolecules, 2001, vol. 34, pp. 7926-7928.
Jen et al., "High-Performance Polyquinolines with Pendent High-Temperature chromophores for Second-Order Nonlinear Optics", Chem. Mater., 1998, vol. 10, pp. 471-473.
Jenekhe et al., "Finite Size Effects on Electroluminescence of Nanoscale Semiconducting Polymer Heterojunctions", Chem. Mater., 1997, vol. 9, pp. 409-412.
Jenekhe et al., "New Conjugated Polymers and Donor-Acceptor Architectures: Synthesis and Photophysics of Carbazole-Quinoline and Phenothiazine-Quinoline Copolymers and Oligomers Exhibiting Large Intramolecular Charge Transfer", Macromolecules, 2001, vol. 34, pp. 7315-7324.
Jiang et al., "Application of named reactions in polymer synthesis", Science China: Chemistry, 2015, vol. 58, 1695-1709.
Kim et al., "Charge-Transport Tuning of Solution-Processable Graphene Nanoribbons by Substitutional Nitrogen Doping", Macromolecular Chemistry and Physics, 2013, vol. 214, pp. 2768-2773.
Kim et al., "New Polyquinoline Copolymers: Synthesis, Optical, Luminescent, and Hole-Blocking/Electron-Transporting Properties", Macromolecules, 2000, vol. 33, pp. 5880-5885.
Kim et al., "Synthesis of graphene nanoribbons with various widths and its application to thin-film transistor", Carbon, 2013, vol. 63, pp. 202-209, available online Jun. 29, 2013.
Kimyonok et al., "Electroluminescent Poly(quinoline)s and Metalloquinolates", Journal of Macromolecular. Science Part C: Polymer Reviews, Nov. 2006, vol. 46, pp. 47-77.
Kivala et al., "Cyclodehydrogenation in the Synthesis of Graphene-Type Molecules", Materials Science and Technology, 2012, pp. 373-420, doi: 10.1002/9783527603978.mst0423.
Koch et al., "Voltage-dependent conductance of a single graphene nanoribbon", Nature Nanotechnology, Nov. 2012, vol. 7, pp. 713-717.
Konatham et al., "Molecular Design of Stable Graphene Nanosheets Dispersions", Nano Letters, 2008, vol. 8, No. 12, pp. 4630-4641, published on web Nov. 5, 2008.
Kotakoski et al., "Imaging atomic-level random walk of a point defect in graphene", Nature Communications, 2014, vol. 5, 3991, doi: 10.1038/ncomms4991, 5 pgs.
Kouznetsov, Vladimir, "Recent synthetic developments in a powerful imino Diels-Alder reaction (Povarov reaction): application to the synthesis of N-polyheterocycles and related alkaloids", Tetrahedron, 2009, vol. 65, pp. 2721-2750.
Kruger et al., "New Organo-Soluble Conjugated Polyquinolines", Macromol. Chem. and Phys., 2003, vol. 204, pp. 1607-1615.
Kulkarni et al., "Electron Transport Materials for Organic Light-Emitting Diodes", Chem. Mater., Oct. 15, 2004, vol. 16, pp. 4556-4573.
Kumar et al., "Biological Activities of Quinoline Derivatives", Mini-Reviews in Medicinal Chemistry, 2009, vol. 9, pp. 1648-1654.
Kumru et al., "Experimental and theoretical studies on IR, Raman, and UV-Vis spectra of Quinoline-7-carboxaldehyde", Spectrochimica Acta Part A: Molecular and Biomolecular Spectroscopy, 2015, vol. 134, pp. 81-89.
Kuninobu et al., "Copper(I)- and Gold(I)-catalyzed Synthesis of 2,4-Disubstituted Quinoline Derivatives from N-Aryl-2-propynylamines", Chemistry Letters, 2007, vol. 36, No. 12, pp. 1422-1423.

(56) References Cited

OTHER PUBLICATIONS

Landberg et al., "Application of functionalised 1,3-Dipoles to the Synthesis of Fused Heterocycles", J Chem. Soc., Perkin Trans., 11975, pp. 1326-1333.

Lee et al., "Charge-Transport Tuning of solution-Processable Graphene Nanoribbons by Substitutional Nitrogen Doping", Macromolecular Chemistry and Physics, 2013, vol. 214, pp. 2768-2773.

Lee et al., "Rubicene: a molecular fragment of c70 for use in organic field-effect transistors", Journal of Materials Chemistry C, 2014, vol. 2, pp. 3361-3366.

Liu et al., "Synthesis and characterization of polyqiniolines for light-emitting diodes", Journal of Materials Chemistry, 1999, vol. 9, pp. 2201-2204.

Singh, "Infrared Spectra of Quinoline and its Addition Compounds with Certain Inorganic Halides", Z. Anorg. Allg. Chem., 1971, vol. 384, pp. 81-88.

Solomon et al., "Quinoline as a Privileged Scaffold in Cancer Drug Discovery", Current Medicinal Chemistry, 2011, vol. 18, pp. 1488-1508.

Stille, "Polyquinolines", Macromolecules, May-Jun. 1981, vol. 14, No. 3, pp. 870-880.

Studer et al., "The electron is a catalyst", Nature Chemistry, Sep. 2014, vol. 6, pp. 765-773, published online Aug. 21, 2014.

Sun et al., "A Study of the Separation Principle in Size Exclusion Chromatography", Macromolecules, 2004, vol. 37, pp. 4304 4312.

Sun et al., "Benzenoid Polycyclic Hydrocarbons with an Open-Shell Biradical Ground State", Chemistry An Asian Journal, 2013, vol. 8, pp. 2894-2904.

Suresh et al., "SnCl2-Catalyzed Selective Atom Economic Imino Diels-Alder Reaction: Synthesis of 2-(1H-Pyrrolo[2,3-b]pryidin-3-yl)quinolines", Journal of Organic Chemistry, Jan. 9, 2012, vol. 77, pp. 1468-1476.

Sutherlin et al., "Biphenylene- and Phenyl-End-Capped Oligomeric Polyquinolines Containing Acetylene Linkages: Preparation, Processing, and Composite Application", Macromolecules, 1986, vol. 19, No. 2, pp. 257-266.

Sygula, "Chemistry on a Half-Shell: Synthesis and Derivatization of Buckybowls", Eur. J. Org. Chem., 2011, pp. 1611-1625.

Taguchi et al., "Catalysis by Molecular Sieves in the Preparation of Ketimines and Enamines", J Org. Chem., 1971, vol. 36, No. 11, pp. 1570-1572.

Talirz et al., "Termini of Bottom-Up Fabricated Graphehe Nanoribbons", Journal of the American Chemical Society, Jan. 27, 2013, vol. 135, pp. 2060-2063.

Tan et al., "Enantioselective synthesis of a chiral nitrogen-doped buckybowl", Nature Communications, Jun. 12, 2012, vol. 3, pp. 1-6.

Tan et al., "Atomically precise edge chlorination of nanographines and its application in graphene nanoribbons", Nov. 11, 2013, vol. 4, 2646, DOI 10.1038/ncomms3646, 7 pgs.

Tasdelen, "Diel-Alder "click" reactions: recent applications in polymer and material science", Polymer Chemistry, 2011, vol. 2, pp. 2133-2145.

Terrones et al., "Graphene and graphite nanoribbons: Morphology, properties, synthesis, defects and applications", Nano Today, 2010, vol. 5, pp. 351-372, available online Aug. 2, 2010.

Thompson et al., "Polymer-Fullerene Composite Solar Cells", Angew. Chem. Int. Ed., 2008, vol. 47, pp. 58-77.

Thompson et al., "Polymer-Fulleren-Solarzellen", Angew. Chem., 2007, vol. 120, pp. 62-82.

Tomar et al., "Facile synthesis of 5,8-linked quinoline-based copolymers", Polym. Int., 2012, vol. 61, pp. 1318-1325, published online Apr. 11, 2012.

Tonzola et al., "A New Synthetic Route to soluble Polyquinolines with Tunable Photophysical, Redox, and Electroluminescent Properties", Macromolecules 2005, vol. 38, pp. 9539-9547.

Tonzola et al., "Blue-Light-Emitting Oligoquinolines: Synthesis, Properties, and High-Efficiency Blue-Light-Emitting Diodes", Advanced Functional Materials, 2007, vol. 17, pp. 863-874.

Tonzola et al., "New Silicon-Containing Polyquinolines: Synthesis, Characterization, and Electroluminescence", Macromolecular Chemistry and Physics, 2005, vol. 206, pp. 1271-1279.

Tonzola et al., "New Soluble n-Type Conjugated Copolymer for Light-Emitting Diodes", Advanced Materials, Aug. 5, 2002, vol. 14, pp. 1086-1090.

Tonzola et al., "New Soluble n-Type Conjugated Polymers for Use as Electron Transport Materials in Light-Emitting Diodes", Macromolecules, 2004, vol. 37, pp. 3554-3563.

Tremblay et al., "Photovoltaic Universal Joints: Ball-and-Socket Interfaces in Molecular Photovoltaic Cells", Chem Phys Chem, 2010, vol. 11, pp. 799-803.

Vo et al., "Bottom-up solution synthesis of narrow nitrogen-doped graphene nanoribbons", Chem. Commun., 2014, vol. 50, pp. 4172-4174.

Vo et al., "Large-scale solution synthesis of narrow graphene nanoribbons", Nature Communications, Feb. 10, 2014, vol. 5, No. 3189, pp. 1-8.

Vostrowsky et al., "Heterofullerenes", Chem. Rev., 2006, vol. 106, pp. 5191-5207.

Wait Jr. et al., "Vibrational Spectra and Assignments for Quninoline and Isoquinoline", Journal of Molecular Spectroscopy, 1970, vol. 34, pp. 56-77.

Wang et al., "A Theoretical Study of the Separation Principle in Size Exclusion Chromatography", Macromolecules, 2010, vol. 43, pp. 1651-1659.

Wang et al., "Heteroatom-doped graphene materials: syntheses, properties and application", Chen, Chem. Soc. Rev., 2014, vol. 43, pp. 7067-7098.

Wang et al., "N-Doping of Graphene Through electrothermal Reactions with Ammonia", Science, May 9, 2009, vol. 324, pp. 768-771.

Wang et al., "Review on Recent Progress in Nitrogen-Doped Graphene: synthesis, Characterization, and Its Potential Applications", ACS Catalysis, Mar. 16, 2012, vol. 2, pp. 781-794.

Wei et al., "Synthesis of N-Doped Graphene by Chemical Vapor Deposition and Its Electrical Properties", Nano Letters, 2009, vol. 9, No. 5, pp. 1752-1758, published on Web Mary 27, 2009.

Whalley et al., "Bending contorted hexabenzocoronene into a bowl", Chemical Science, 2011, vol. 2, pp. 132-135.

Williams et al., "Drying of Organic solvents: Quantitative Evaluation of the Efficiency of Several Desiccants", J Org. Chem., 2010, vol. 75, pp. 8351-8354.

Wu et al., "Graphenes as Potential Materials for Electronics", Chem. Rev., 2007, vol. 107, pp. 718-747.

Wu et al., "Oxygen-and Sulfur-Containing Positively Charged Polycyclic Aromatic Hydrocarbons", Organic Letters, 2009, vol. 11, pp. 5686-5689, published on Web Nov. 17, 2009.

Yan et al., "Intrinsic Current-Voltage Characteristics of Graphene Nanoribbon Transistors and Effect of Edge Doping", Nano Letters, 2007, vol. 7, No. 6, pp. 1469-1473, published on Web Apr. 27, 2007.

Yan et al., "Large, Solution-Processable graphene Quantum Dots as Light Absorbers for Photovoltaics", Nano. Letters, 2010, vol. 10, pp. 1869-1873, published on Web Apr. 8, 2010.

Yan et al., "Synthesis of Large, Stable Colloidal Graphene Quantum Dots with Tunable Size", J. Am. Chem. Soc. Communications, 2010, vol. 132, pp. 5944-5945, published on Web Apr. 8, 2010.

Yanez et al., "A New Approach to the Synthesis of Dibenzo[a,l]pyrenes", J. Org. Chem., 1971, vol. 36, No. 15, pp. 2053-2056.

Yang et al., "Two-dimensional Graphene Nanoribbons", J. Am. Chem. Soc., 2008, vol. 130, pp. 4216-4217, published on Web Mar. 7, 2008.

Yao et al., "One-pot solvent-free synthesis of quinolines by C—H activation/C—C Bond formation catalyzed by recyclable iron(III) triflate", RSC Advances, 2012, vol. 2, pp. 3759-3764.

Yazyev, "A guide to the Design of Electronic Properties of Graphene Nanoribbons", Accounts of Chemical Research, 2013, vol. 46, No. 10, pp. 2319-2328, published on Web Jan. 3, 2013.

Zhan et al., "New Series of Blue-Emitting and Electron-Transporting Copolymers Based on Fluorene", Macromolecules, 2002, vol. 35, pp. 2529-2537.

Zhang et al., "Direct visualization of atomically precise nitrogen-doped graphene nanoribbons", Applied Physics Letters, 2014, vol. 105, pp. 023101-1-023101-4, published online Jul. 14, 2014.

(56) References Cited

OTHER PUBLICATIONS

Zhang et al., "Electroluminescence and Photophysical Properties of Polyquinolines", Macromolecules, 1999, vol. 32, pp. 7422-7429.

Zhang et al., "Electroluminescence of Multicomponent Conjugated Polymers. 1. Roles of Polymer/Polymer Interfaces in Emission Enhancement and Voltage-Tunable Multicolor Emission in Semiconducting Polymer/Polymer Heterojunctions", Macromolecules, 2000, vol. 33, pp. 2069-2082.

Zhang et al., "Iron-Catalyzed Tandem Reactions of Aldehydes, Terminal Alkynes, and Primary Amines as a Strategy for the Synthesis of Quinoline Derivatives", J. Heterocycl. Chem., 2011, vol. 48, pp. 153-157, published online Oct. 6, 2010.

Zhang et al., "Transmission Electron Microscopy and the Science of Carbon Nanomaterials", Small, 2014, vol. 10, No. 2, pp. 222-229.

Zhao et al., "25th Anniversary Article: Recent Advances in n-type and Ambipolar Organic Field Effect Transistors", Advanced Materials, 2013, vol. 25, pp. 5372-5391.

Zhao et al., "Dopant Segregation in Polycrystalline Monolayer Graphene", Nano Letters, Jan. 27, 2015, vol. 15, pp. 1428-1436.

Zhao et al., "Electron transporting semiconducting polymers in organic electronics", Chem. Soc. Rev., Mar. 15, 2011, vol. 40, 3728-3743.

Zhao et al., "Visualizing Individual Nitrogen Dopants in Monolayer Graphene", Science, 2011, vol. 333, pp. 999-1003.

Zhou et al., "Origin of the energy bandgap in epitaxial graphene", Nature Materials, Apr. 2008, vol. 7, pp. 258-260.

Zyung et al., "Electroluminescent Devices Using a Polymer of Regulated Conjugation Length and a Polymer Blend", ETRI Journal, Oct. 1996, vol. 18, No. 3, pp. 181-193.

\* cited by examiner

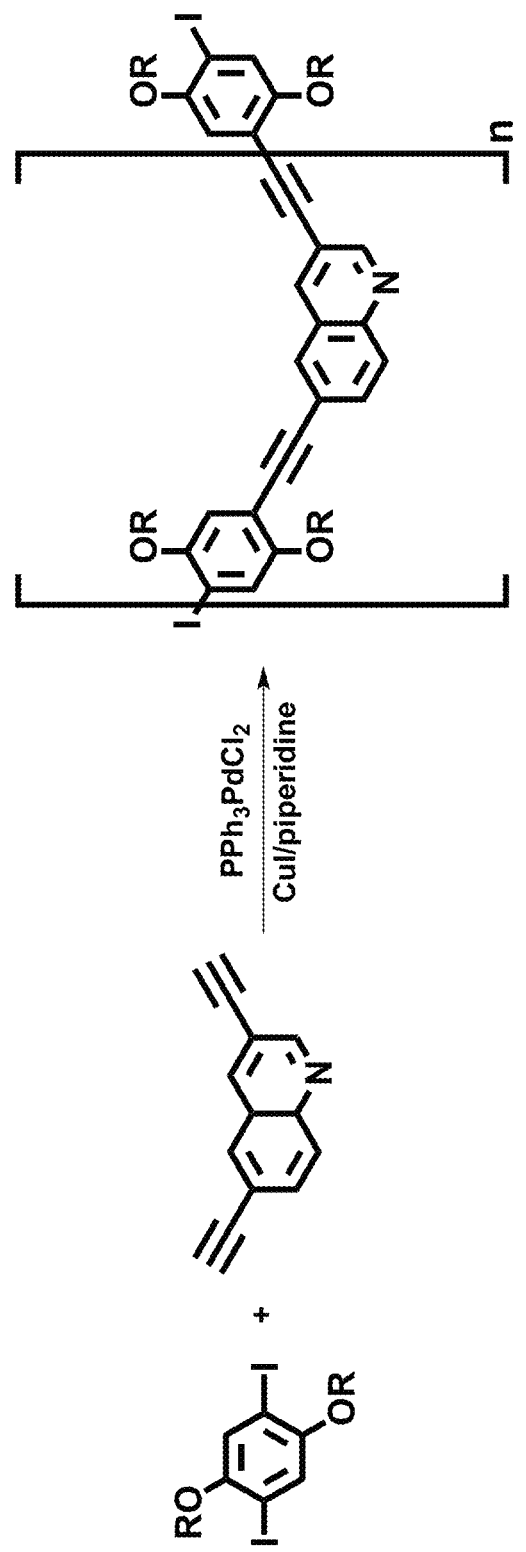
FIG. 1B1
PRIOR ART

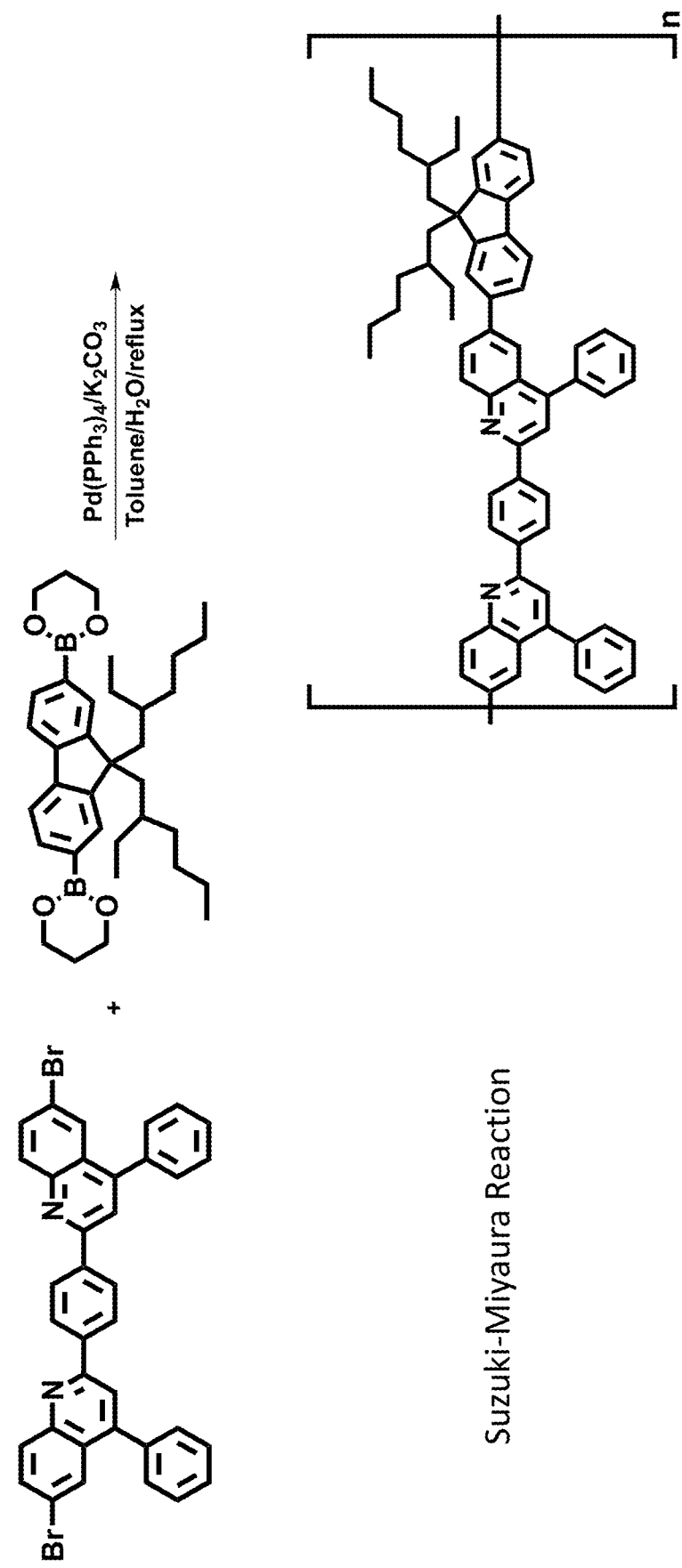
FIG. 1B2
PRIOR ART
Suzuki-Miyaura Reaction

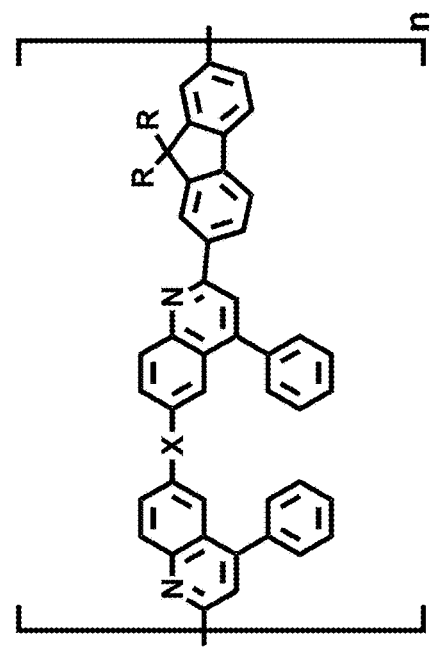
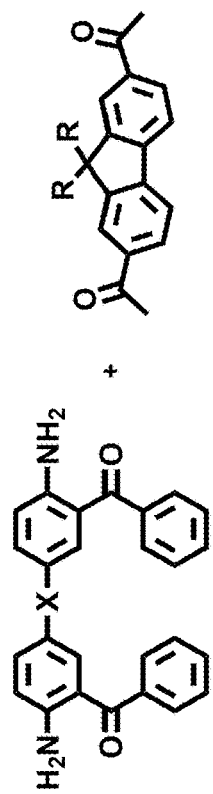
FIG. 1B3
PRIOR ART

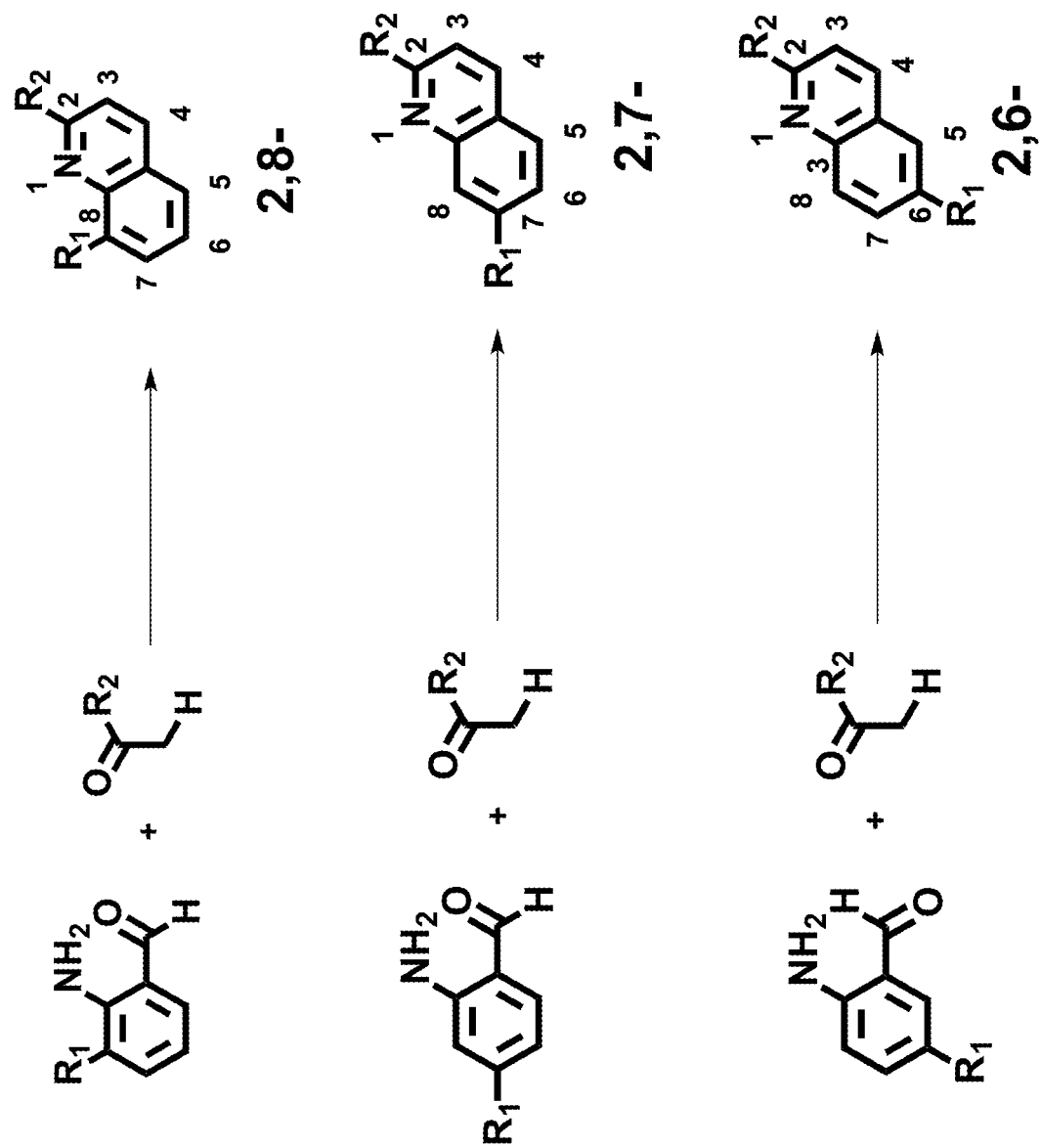
FIG. 1C1
PRIOR ART

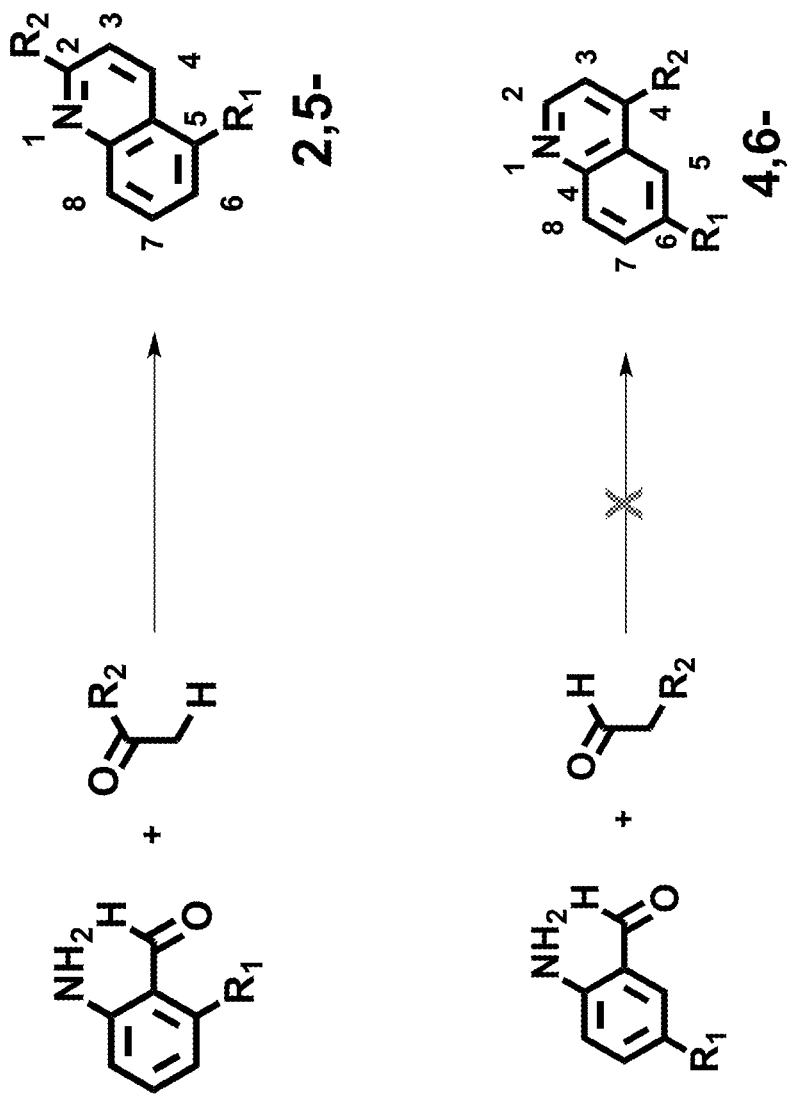
FIG. 1C2
PRIOR ART

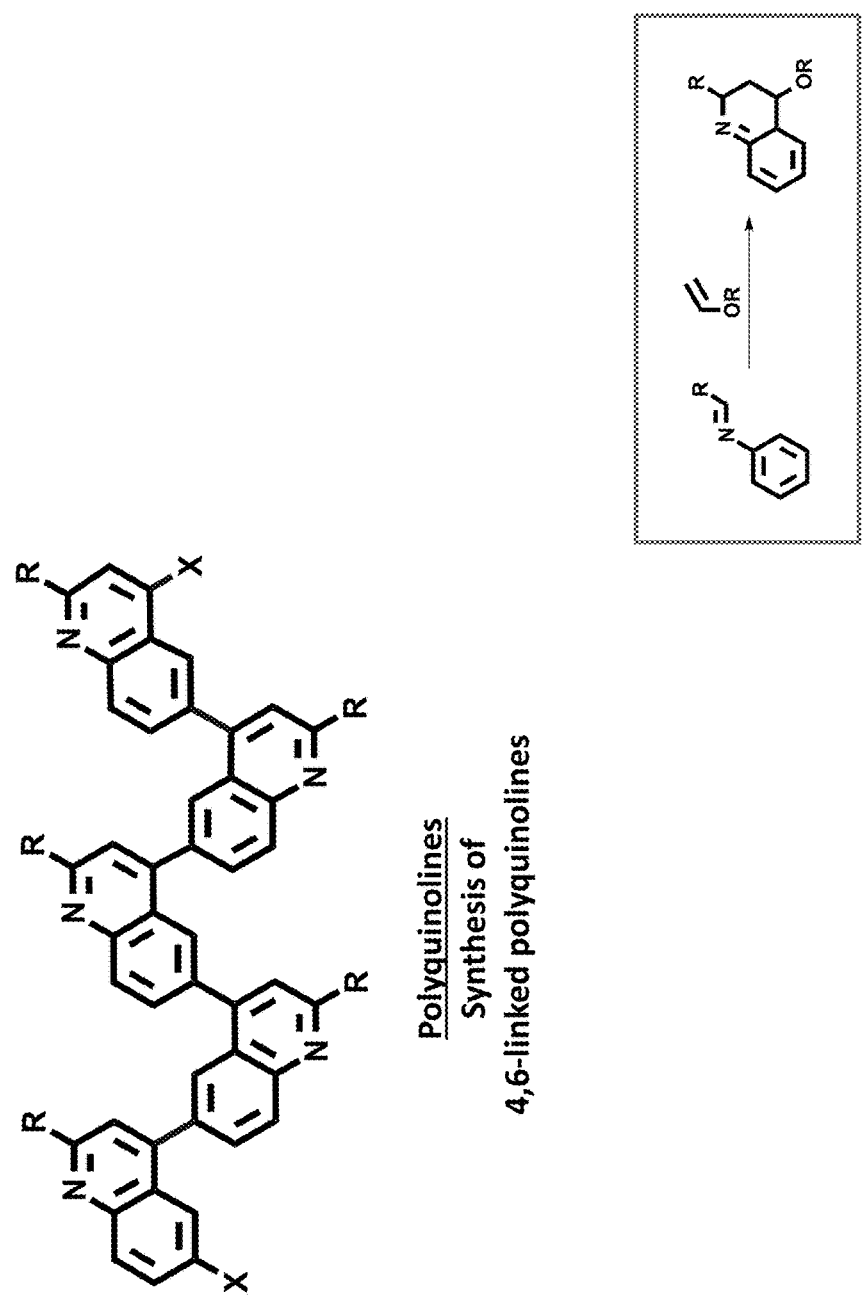
FIG. 2A1

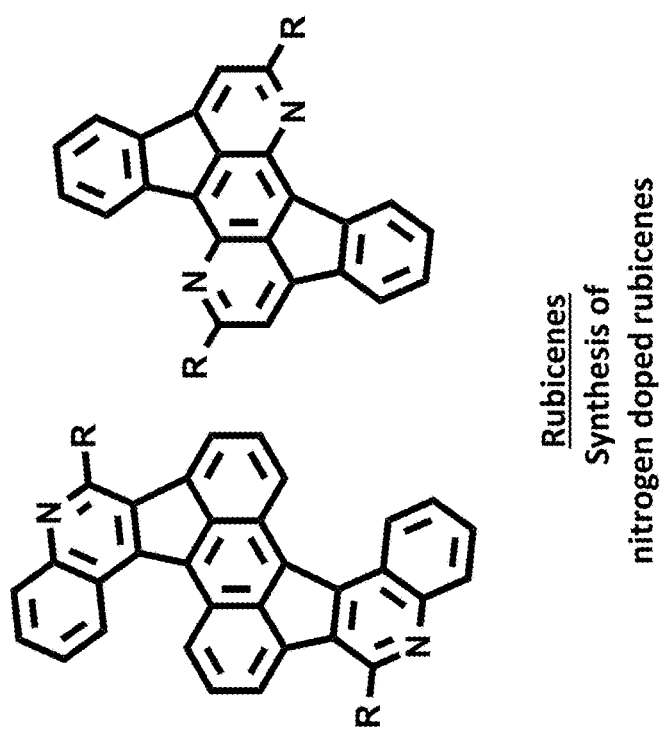
FIG. 2A2

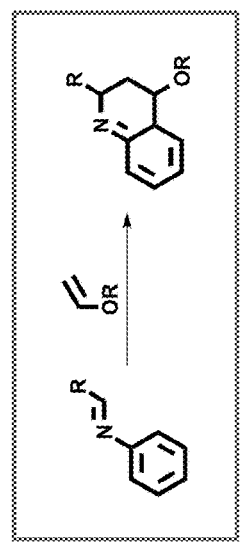
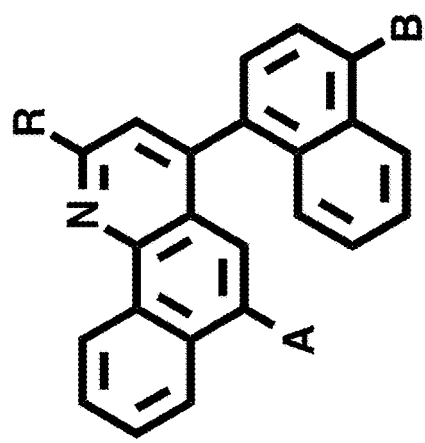
Benzoquinolines
Synthesis of benzoquinolines via the Povarov reaction
FIG. 2A3

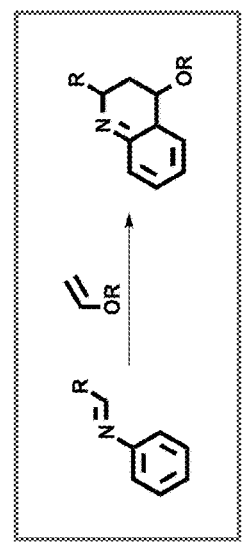
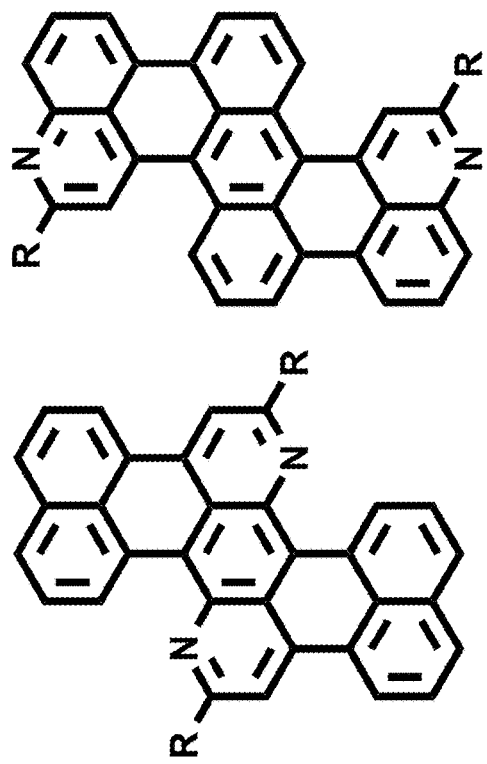
Tetrobenzopentacenes
Synthesis of tetrabenzopentacenes
FIG. 2A4

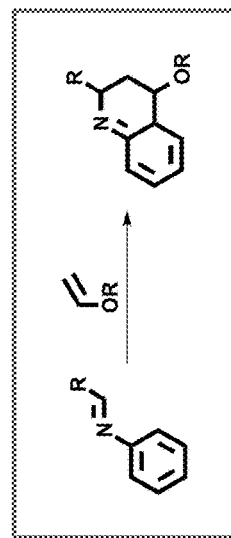
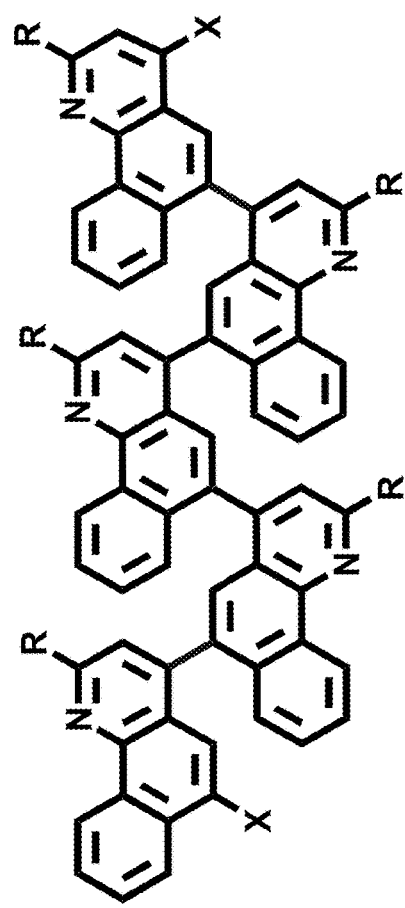
Polybenzoquinolines
Sythesis of oligobenzoquinolines and polybenzoquinolines
FIG. 2A5

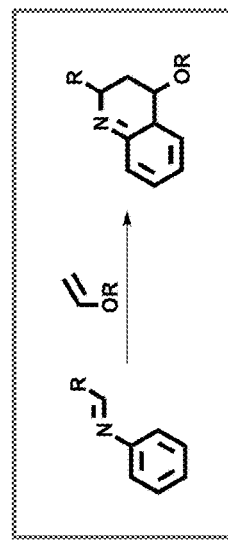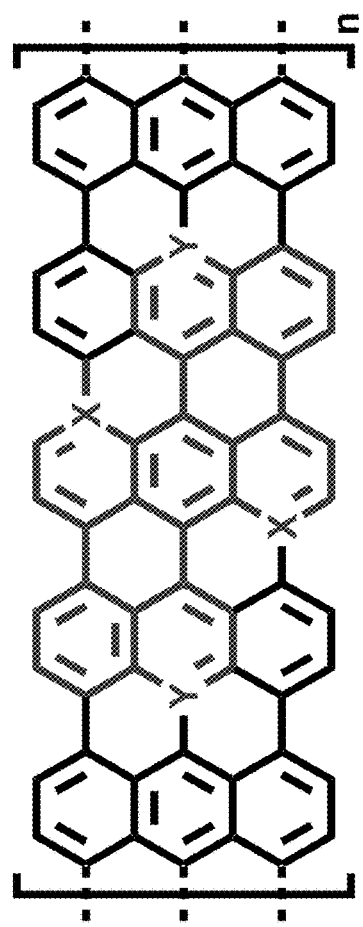
FIG. 2A6
Graphene Nanoribbons
Synthesis of nitrogen doped GNRs

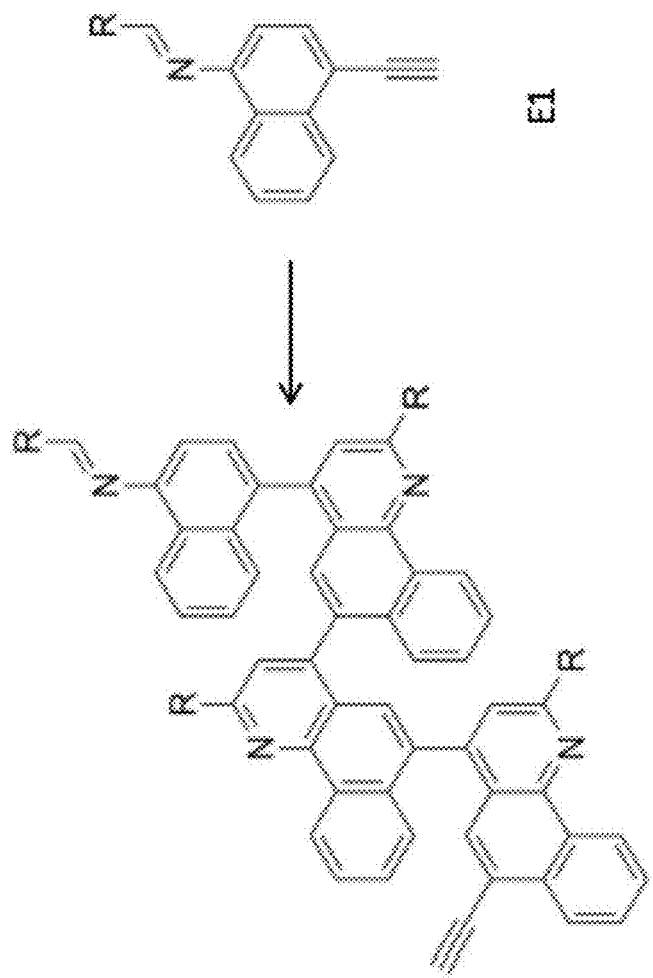
FIG. 4B1

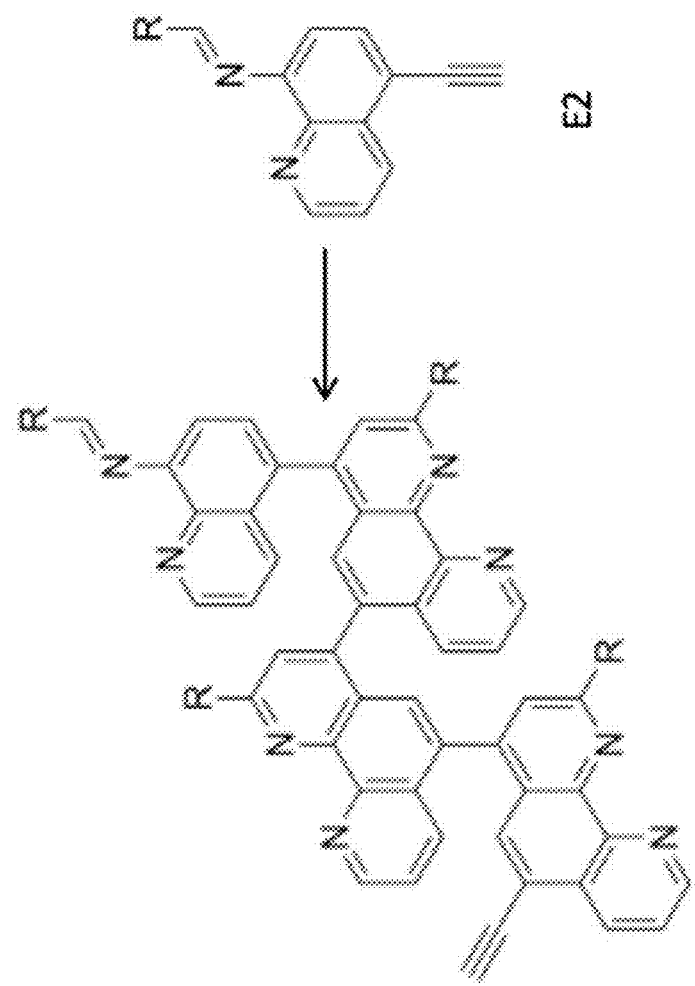
FIG. 4B2

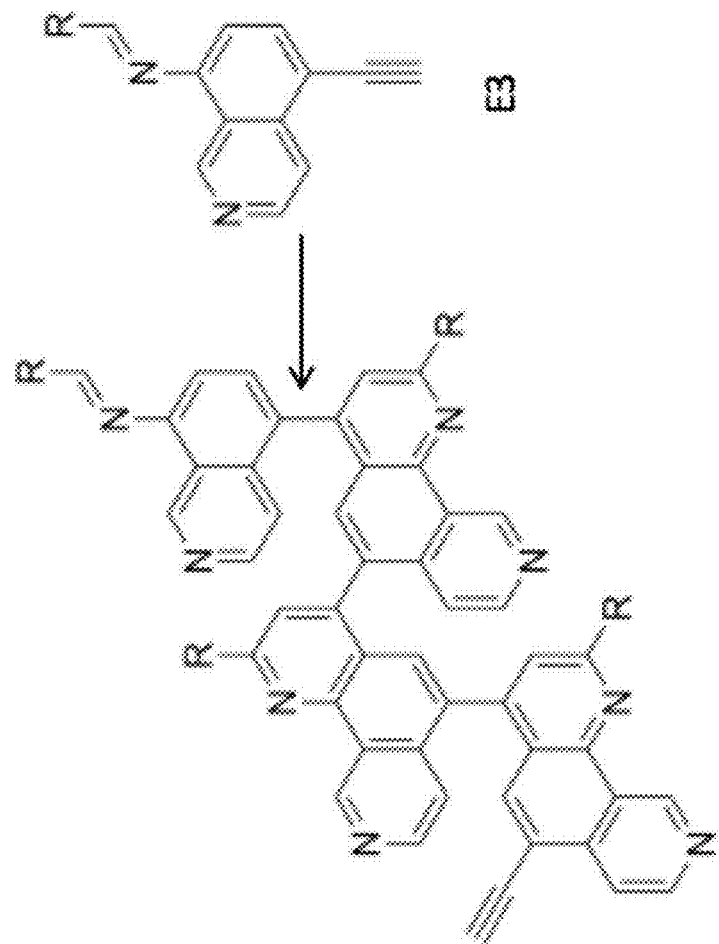
FIG. 4B3

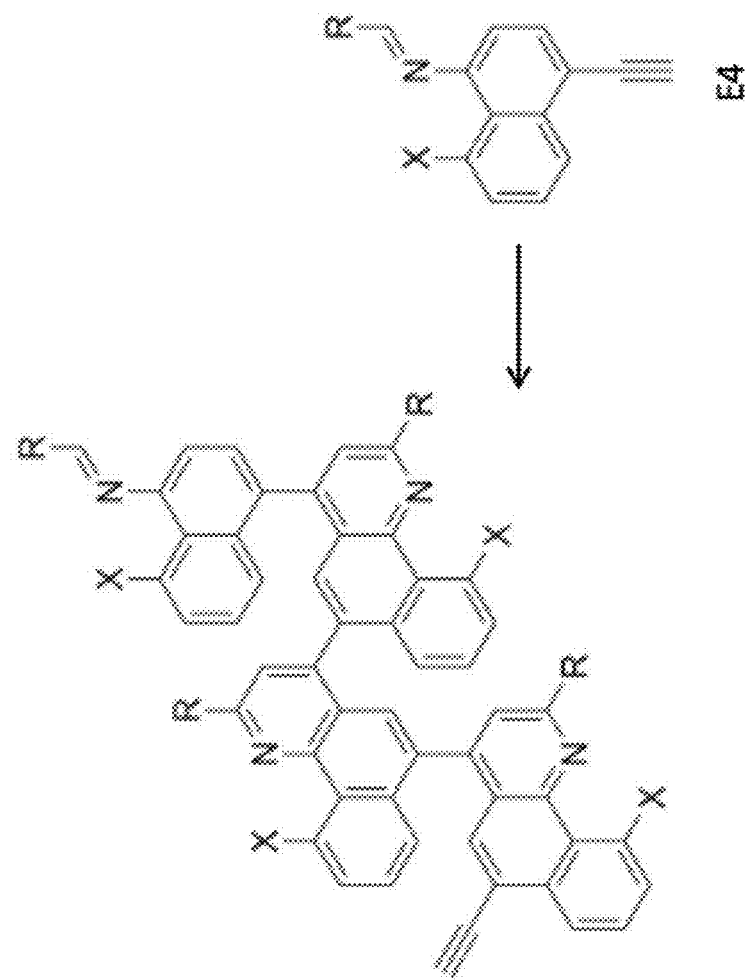
FIG. 4B4

| Entry | Compound[a] | L.A. | R | Yield[b] (%) |
|---|---|---|---|---|
| 1 | 3a | AlCl$_3$ |  | 0 |
| 2 | 3a | Y(OTf) |  | 38 |
| 3 | 3a | FeCl$_3$ |  | 53 |
| 4 | 3a | SnCl$_2$ |  | 33 |
| 5 | 3a | Ag(OTf) |  | 67 |
| 6 | 3a | ZnCl$_2$ |  | 75 |
| 7 | 3a | BF$_3$·OEt$_2$ |  | 83 |
| 8 | 3b | BF$_3$·OEt$_2$ |  | 82 |
| 9 | 3c | BF$_3$·OEt$_2$ |  | 82 |
| 10 | 3d | BF$_3$·OEt$_2$ |  | 76 |
| 11 | 3e | BF$_3$·OEt$_2$ |  | 76 |
| 12 | 3f | BF$_3$·OEt$_2$ |  | 75 |
| 13 | 3g | BF$_3$·OEt$_2$ |  | 70 |
| 14 | 3h | BF$_3$·OEt$_2$ |  | 68 |
| 15 | 3i | BF$_3$·OEt$_2$ |  | 68 |

Model Quinoline

Quinoline Monomer

QUINOLINES, POLYQUINOLINES, MOLECULAR SEGMENTS OF FULLERENES AND GRAPHENE NANORIBBONS, AND GRAPHENE NANORIBBONS AND METHODS OF THEIR SYNTHESIS

CROSS-REFERENCE TO RELATED APPLICATIONS

The present application is a national stage of Application No. PCT/US15/68339, entitled "Quinolines, Polyquinolines, Molecular Segments of Fullerenes and Graphene Nanoribbons, and Graphene Nanoribbons and Methods of Their Synthesis", filed Dec. 31, 2015, which application claims priority to U.S. Provisional Application No. 62/135,579, filed Mar. 19, 2015, and U.S. Provisional Application No. 62/098,512, filed Dec. 31, 2014, the disclosures of which are incorporated herein by reference in their entireties.

STATEMENT OF FEDERAL FUNDING

This invention was made with Government support under Grant No. N00014-13-1-0650 and N00014-12-1-0491 awarded by the Office of Naval Research—N99914. The government has certain rights in the invention.

FIELD OF THE INVENTION

The present disclosure is directed to quinolines, polyquinolines, benzoquinolines, polybenzoquinolines, molecular segments of fullerenes and graphene nanoribbons, and graphene nanoribbons as well as methods of synthesizing such compounds and materials.

BACKGROUND OF THE INVENTION

Carbon-based materials, such as fullerenes, carbon nanotubes and graphene nanoribbons (GNRs)(FIG. 1A), have often been touted as the successors to inorganic semiconductors in solar cells and nanoscale transistors. (See, e.g., Pierre Delhaes, *Carbon-based Solids and Materials*, John Wiley & Sons, Inc., Hoboken, 2011; V. Georgakilas, et al., *Chem. Rev.* 2015, 115, 4744-4822; A. K. Geim, P. Kim, *Sci. Am.* 2008, April, 90-97; B. C. Thompson, J. M. J. Fréchet, *Angew. Chem. Int. Ed.* 2008, 47, 58-77; Angew. Chem. 2007, 120, 62-82; G. Dennler, et al., *Adv. Mater.* 2009, 21, 1323-1338; F. Schwierz, *Nat. Nanotechnol.* 2010, 5, 487-496; and A. C. Ferrari, et al., *Nanoscale* 2015, 7, 4598-4810, the disclosures of which are incorporated herein by reference.) Thus, much research effort has focused on either top-down lithographic approaches (see, e.g., L. Chen, et al. *Angew. Chem. Int.* 2012, 51 7640-7654; L. Ma, et al. *Chem Phys Chem* 2013, 14, 47-54; Z. Chen, et al. *Physica E* 2007, 40, 223-232; M. Terronew, et al. *Nano Today* 2010, 5, 351-372; and K. Mullen, *ACS Nano* 2014, 8, 6531-6541, the disclosures of which are incorporated herein by reference), or the bottom-up preparation of structurally and chemically well-defined variants of these carbon allotropes, as well as their molecular segments, via traditional organic chemistry techniques. (See, e.g., L. T. Scott, *Angew. Chem. Int. Ed.* 2004, 43, 4994-5007; L. T. Scott, Angew. Chem. 2004, 116, 5102-5116; A. Sygula, *Eur. J. Org. Chem.* 2011, 1611-1625; *Fragments of Fullerenes and Carbon Nanotubes: Designed Synthesis, Unusual Reactions, and Coordination Chemistry* (Eds.: M. A. Petrukhina, L. T. Scott), John Wiley & Sons, Inc., Hoboken, 2011; L. T. Scott, *Polycyclic Aromat. Compd.* 2010, 30, 247-259; M. Mojica, et al., *J. Phys. Org. Chem.* 2013, 26, 526-539; A. Narita, et al., *Chem. Soc. Rev.* 2015, 44, 6616-6643; L. Chen, et al., *Angew. Chem. Int. Ed.* 2012, 51, 7640-7654; J. Wu, et al., *Chem. Rev.* 2007, 107, 718-747; A. Narita, et al., *Chem. Rec.* 2015, 15, 295-309; and Z. Sun, et al., *Chem. Asian J.* 2013, 8, 2894-2904, the disclosure of which is incorporated herein by reference.) However, far fewer studies have demonstrated the solution-phase synthesis of analogous nitrogen-doped constructs. (See, e.g., T. H. Vo, et al., *Chem. Commun.* 2014, 50, 4172-4174; K. T. Kim, J. W. Lee, W. H. Jo, *Macromol. Chem. Phys.* 2013, 214, 2768-2773; D. J. Dibble, et al., *Angew. Chem. Int. Ed.* 2015, 54, 5883-5887; Q. Tan, et al., *Nat. Commun.* 2012, 3, 891; S. Ito, et al., *Angew. Chem. Int. Ed.* 2015, 54, 7256-7260; and R. Berger, et al., Angew. *Chem. Int. Ed.* 2014, 53, 10520-10524, the disclosures of which are incorporated herein by reference.) Given that substitutional doping is a classic strategy for tuning the properties of electronic materials, this gap in the literature is surprising and likely stems from the difficulties inherent to the synthetic incorporation of nitrogen heteroatoms at arbitrary locations in graphitic systems. (See, e.g., X. Wang, et al. Chen, *Chem. Soc. Rev.* 2014, 43, 7067-7098; O. Vostrowsky, A. Hirsch, *Chem. Rev.* 2006, 106, 5191-5207; J. C. Hummelen, C. Bellavia-Lund, F. Wudl, *Top. Curr. Chem.* 1999, 199, 93-134; P. T. Araujo, M. Terrones, M. S. Dresselhaus, *Mater. Today* 2012, 15, 98-109; R. Lv, M. Terrones, *Mater. Lett.* 2012, 78, 209-218, the disclosures of which are incorporated herein by reference.) Consequently, the development of new routes to nitrogen-containing segments of fullerenes and GNRs remains of paramount importance for the next generation of semiconductor devices and technologies.

Polyquinolines have been studied in both academia and industry since the early 1970s due to their impressive chemical stability as well as their excellent optical, electrical, and mechanical properties. Such favorable properties have enabled polyquinolines to demonstrate their promise for not only optoelectronic but also biomedical applications. (See, e.g., Stille, J. K. *Macromolecules* 1981, 14, 870-880; Kulkarni, A. P., et al. *Chem. Mater.* 2004, 16, 4556-4573; Rusanov, et al. *Russ. Chem. Rev.* 2005, 74, 671-683; Kimyonok, A., et al. *Macromol. Sci., Polym. Rev.* 2006, 46, 47-77; Zhao, X. and Zhan, X. *Chem. Soc. Rev.* 2011, 40, 3728-3743; Nalwa, H. S., et al. *Appl. Phys. Lett.* 1998, 72, 1311-1313; Parker, I. D. et al., *Appl. Phys. Lett.* 1994, 65, 1272-1274; Liu, M. S., et al. *Mater. Chem.* 1999, 9, 2201-2204; Tonzola, C. J. *Macromolecules* 2005, 38, 9539-9547; Tonzola, C. J., et al. *Adv. Funct. Mater.* 2007, 17, 863-874; Kim, J. L., et al. *Macromolecules* 2000, 33, 5880-5885; Zhang, X., et al. *Chem. Mater.* 1997, 9, 409-412; Kumar, S., et al. *Rev. Med. Chem.* 2009, 9, 1648-1654; Broch, S., et al. *Eur. J. Med. Chem.* 2010, 45, 1657-1662; Solomon, V. R. and Lee, H. *Curr. Med. Chem.* 2011, 18, 1488-1508.; Saugues, E., et al. *J. Med. Chem.* 2012, 57, 112-125; and Lu, J., et al. *Spectrochim. Acta, Part A* 2014, 130, 390-396, the disclosures of which are incorporated herein by reference.) To date, polyquinolines have been prepared via a limited number of synthetic strategies, including Suzuki couplings, the Sonogashira reaction, oxidative polymerizations, and the Friedländer synthesis, which are summarized in FIGS. 1B1 to 1B3. (See, e.g., Siemssen, B., et al. *Mol. Cryst. Liq. Cryst.* 2006, 462, 159-167; Tomar, M., et al. *J. Polym. Int.* 2012, 61, 1318-1325; Bangcuyo, C. G., et al. *Macromolecules* 2002, 35, 1563-1568; Bilici, A., et al. *React. Funct. Polym.* 2011, 71, 675-683; Beever, W. H. and Stille, J. K. *Macromolecules* 1979, 12, 1033-1038.; Marco-Contelles, J., et al. *Chem. Rev.* 2009, 109, 2652-2671; Sutherlin, D. M., et al.

Macromolecules 1986, 19, 257-266; Jen, A. K.-Y., et al. *Chem. Mater.* 1998, 10, 471-473; Ma, H., et al. *Macromolecules* 1998, 31, 4049-4052; Ma, H., et al. *S. Chem. Mater.* 1999, 11, 2218-2225; and Agrawal, A. K. and Jenekhe, S. A. *Macromolecules* 1993, 26, 895-905, the disclosure of which are incorporated herein by reference.) The latter approach has proven particularly effective, as demonstrated in seminal studies by Jenekhe and co-workers. (See, e.g., Agrawal, A. K. and Jenekhe, S. A. *Chem. Mater.* 1996, 8, 579-589; Zhang, X. and Jenekhe, S. A. *Macromolecules* 2000, 33, 2069-2082; Chen, X. L. and Jenekhe, S. A. *Macromolecules* 2000, 33, 4610-4612; and Jenekhe, S. A., et al. *Macromolecules* 2001, 34, 7315-7324, the disclosures of which are incorporated herein by reference.) However, the known routes to polyquinolines suffer from some disadvantages; they frequently necessitate difficult multi-step monomer syntheses, yield products with poor solubility, or provide access to only a limited number of structural motifs. For example, the Friedländer synthesis often requires the resulting polyquinolines to possess complex side chain substituents for enhanced solubility and cannot provide access to certain backbone architectures, such as those containing 4,6-linked quinoline subunits, as shown in FIGS. 1C1 and 1C2. (See, e.g., Tonzola, C. J., et al. *Adv. Mater.* 2002, 14, 1086-1090; Tonzola, C. J., et al. *Macromolecules* 2004, 37, 3554-3563; Krüger, H., et al. *Macromol. Chem. Phys.* 2003, 204, 1607-1615; Zhan, X., et al. *Macromolecules* 2002, 35, 2529-2537; Chen, C.-H. and Shu, C.-F. *J. Polym. Sci., Part A: Polym. Chem.* 2004, 42, 3314-3322; and Tonzola, C. J., et al. *Macromol. Chem. Phys.* 2005, 206, 1271-1279, the disclosure of which are incorporated herein by reference.) Thus, given the aforementioned limitations, there remains a need for the development of alternative routes to polyquinoline-type materials.

BRIEF SUMMARY OF THE INVENTION

The disclosure is generally directed generally to quinolines and polyquinolines, benzo- and polybenzoquinolines, molecular segments of fullerenes and graphene nanoribbons, and graphene nanoribbons and methods for the synthesis thereof.

Some embodiments of the disclosure are directed to methods of producing a quinoline including:
providing a halogenated aromatic aldimine according to:

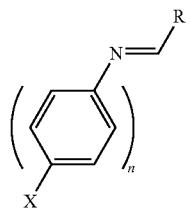

wherein X is a halogen, n is an integer of at least 1, and R is an unsubstituted or substituted aromatic ring; and
reacting the halogenated aromatic aldimine with an alkynyl in the presence of a Lewis acid mediator and an oxidant such that the imine group of the halogenated aromatic aldimine reacts with the alkyne group of the alkynyl yielding a quinoline wherein the nitrogen from the imine group is incorporated into the multicyclic quinoline ring.

In other embodiments n is at least 2 and the alkynyl comprises a multicyclic aromatic ring such that a benzoquinoline is formed.

In still other embodiments the alkynyl is a naphthyl alkyne such that a 2,4,6 substituted benzoquinoline is formed.

In yet other embodiments at least one of the substituents is selected from the group of electron withdrawing, electron donating, and aliphatic substituents.

In still yet other embodiments the halogenated aromatic comprises an ortho substituent on a pendant phenyl ring thereof.

In still yet other embodiments the method includes converting the halogen of the benzoquinoline to form an alkyne functionalized benzoquinoline and reacting such alkyne functionalized benzoquinolines with the halogenated aromatic aldimine in a Lewis acid mediator and an oxidant such that the imine group of the halogenated aromatic aldimine reacts with the alkyne group of the alkyne functionalized benzoquinoline yielding a dimeric oligobenzoquinoline.

In still yet other embodiments the alkynyl further comprises an acetyl-protected amine; and the method further includes converting the acetyl-protected amine to an imine to form imine functionalized benzoquinoline and reacting such alkyne and imine functionalized benzoquinolines in a Lewis acid mediator and an oxidant such that the imine group of the imine functionalized benzoquinoline reacts with the alkyne group of the alkyne functionalized benzoquinoline yielding a pentameric oligobenzoquinoline.

In still yet other embodiments the R group comprises a benzene having at least one heteroatom and/or further substitution selected from a halogen, an alkyl chain, an alkoxy (e.g., OMe), an acetyl (Ac), an N-acetyl, an amine, an alkyl amine (e.g., N(Me)$_2$), and a sulfide (e.g., SMe).

Some other embodiments of the disclosure are directed to a method of producing polyquinoline including:
providing a bifunctional monomer according to:

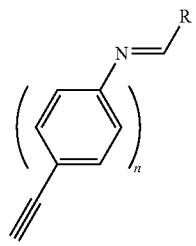

wherein n is an integer of at least 1, and R is an unsubstituted or substituted aromatic ring; and
polymerizing the bifunctional monomer in the presence of a Lewis acid mediator and a sacrificial oxidant such that the imine group of one bifunctional monomer reacts with the alkyne group of another bifunctional monomer, yielding a polyquinoline product wherein the nitrogen from the imine group is incorporated into each of the multicyclic quinoline rings of the polyquinoline.

In other embodiments the aromatic ring of R has at least one heteroatom and/or is further substituted with at least one of the following a halogen, an alkyl chain, an alkoxy (e.g., OMe), an acetyl (Ac), an N-acetyl, an amine, an alkyl amine (e.g., N(Me)$_2$), and a sulfide (e.g., SMe).

In still other embodiments the aromatic ring of R has at least two substitutions.

In yet other embodiments the method further includes terminating the polymerization reaction to obtain a polyquinoline of specified length.

In still yet other embodiments n is at least 2 such that a polybenzoquinoline product is formed. In some such embodiments the second aromatic ring comprises at least one heteroatom and/or a further substituent. In some other such embodiments the substituent is selected from the group of a halogen, an alkyl chain, an alkoxy (e.g., OMe), an acetyl (Ac), an N-acetyl, an amine, an alkyl amine (e.g., N(Me)$_2$), and a sulfide (e.g., SMe). In still other such embodiments the bifunctional monomer further comprises an additional benzoquinoline subunit. In yet other such embodiments the additional benzoquinoline subunit further comprises at least one heteroatom and/or an additional substituent group selected from the group of a halogen, an alkyl chain, an alkoxy (e.g., OMe), an acetyl (Ac), an N-acetyl, an amine, an alkyl amine (e.g., N(Me)$_2$), and a sulfide (e.g., SMe).

In still yet other embodiments the individual quinolines of the polyquinoline are linked at the 4 and 6 positions.

Still some other embodiments of the disclosure are directed to a method of producing biquinoline including:
providing an AA-type monomer comprising an aromatic bisaldimine and a BB-type monomer comprising an aromatic alkynyl; and
reacting the AA-type monomer with the BB-type monomer in the presence of a Lewis acid mediator and an oxidant such that the imine group of AA-type monomer reacts with the alkyne group of the aromatic alkynyl yielding a biquinoline wherein the nitrogen from the imine group is incorporated into each of the multicyclic quinoline rings.

In other embodiments the aromatic rings of the AA-type monomer are further functionalized by a substituted or unsubstituted aromatic ring. In some such embodiments the aromatic ring has at least one heteroatom and/or is further substituted with at least one of the following a halogen, an alkyl chain, an (e.g., OMe), an acetyl (Ac), an N-acetyl, an amine, an alkyl amine (e.g., N(Me)$_2$), and a sulfide (e.g., SMe).

In still other embodiments the bisaldimine comprises at least two aromatic rings.

Yet some other embodiments of the disclosure are directed to a method of producing polyquinoline including:
providing an AA-type monomer comprising an aromatic bisaldimine and a BB-type monomer comprising an aromatic dialkynyl; and
reacting the AA-type monomer with the BB-type monomer in the presence of a Lewis acid mediator and an oxidant such that the imine group of the AA-type monomer reacts with the alkyne group of the BB-type monomer yielding a polyquinoline wherein the nitrogen from the imine group is incorporated into each of the multicyclic quinoline rings of the polyquinoline.

In other embodiments the aromatic rings of the AA-type monomer are further functionalized by a substituted or unsubstituted aromatic ring. In some such embodiments the aromatic ring has at least one heteroatom and/or is further substituted with at least one of the following a halogen, an alkyl chain, an alkoxy (e.g., OMe), an acetyl (Ac), an N-acetyl, an amine, an alkyl amine (e.g., N(Me)$_2$), and a sulfide (e.g., SMe).

In still other embodiments the bisaldimine comprises at least two aromatic rings.

Still yet some other embodiments of the disclosure are directed to a method of forming a molecular segment including:
reacting a halogenated aromatic bisaldimine and an alkyne functionalized aromatic ring in the presence of a Lewis acid mediator and an oxidant such that the imine groups of the bisaldimine reacts with the alkyne group of the alkyne functionalized aromatic ring yielding a halogenated anthracene precursor having at least two pendant aromatic groups; and
forming intramolecular C—C bonds between the acene cored and pendant aromatic groups to form a nitrogen-doped molecular segment.

In other embodiments the pendant aromatic groups are phenyls and the step of forming intramolecular C—C bonds utilizes a Heck reaction to yield a nitrogen-doped rubicene molecular segment product.

In still other embodiments the pendant aromatic groups are naphthyls and the step of forming intramolecular C—C bonds utilizes a base mediated cyclodehydrogenation to yield a nitrogen-doped tetrabenzopentacene molecular segment product.

Still yet some other embodiments of the disclosure are directed to a method of forming a molecular segment including:
reacting a halogenated anthracene bisalkyne and an aromatic adimine in the presence of a Lewis acid mediator and an oxidant such that the imine groups of the aldimine reacts with the alkyne group of the halogenated anthracene bisalkyne yielding a halogenated anthracene precursor having at least two pendant quinoline groups; and
forming intramolecular C—C bonds between the acene cored and pendant quinoline groups to form a nitrogen-doped molecular segment.

In other embodiments the step of forming intramolecular C—C bonds utilizes a Heck reaction to yield a nitrogen-doped rubicene molecular segment product.

In still other embodiments the step of forming intramolecular C—C bonds utilizes a base mediated cyclodehydrogenation to yield a nitrogen-doped tetrabenzopentacene molecular segment product.

Still yet some other embodiments of the disclosure are directed to a method of forming graphene nanoribbon including:
providing a bifunctional monomer according to:

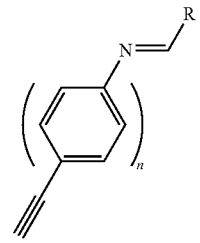

wherein n is an integer of at least 1, and R is an unsubstituted or substituted aromatic ring;
polymerizing the bifunctional monomer in the presence of a Lewis acid mediator and a sacrificial oxidant such that the imine group of one bifunctional monomer reacts with the alkyne group of another bifunctional monomer, yielding a polyquinoline product wherein the nitrogen from the imine group is incorporated into each of the multicyclic quinoline rings of the polyquinoline;

continuing the polymerization of the polyquinoline to yield a polyquinoline precursor; and cyclodehydrogenating the polyquinoline precursor to yield a graphene nanoribbon.

In other embodiments n is at least 2 such that a polybenzoquinline product is formed. In some such embodiments the benzoquinolines incorporate substituents at the 2 position, such that the substituents are disposed at edge locations along the graphene nanoribbon.

In still other embodiments the graphene nanoribbon is a nitrogen-doped N=7 armchair graphene nanoribbon. In some such embodiments the concentration of nitrogen doping can vary from 7 to 14%.

Still yet some other embodiments of the disclosure are directed to polyquinolines formed of a plurality of quinolines interlinked at the 4 and 6 positions.

Still yet some other embodiments of the disclosure are directed to polybenzoquinolines comprising two or more benzoquinolines interlinked at the 4 and 6 positions.

Still yet some other embodiments of the disclosure are directed to nitrogen-doped molecular segments selected from one of either rubicene or tetrapentacene.

Still yet some other embodiments of the disclosure are directed to quinoline monomers including:

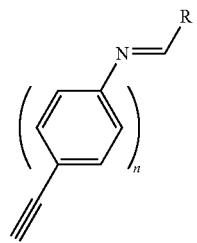

wherein n is an integer of at least 1, and R is an unsubstituted or substituted aromatic ring.

In other embodiments the aromatic ring of R has at least one heteroatom and/or is further substituted with at least one of the following a halogen, an alkyl chain, an alkoxy (e.g., OMe), an acetyl (Ac), an N-acetyl, an amine, an alkyl amine (e.g., $N(Me)_2$), and a sulfide (e.g., SMe). In some such embodiments the aromatic ring of R has at least two substitutions.

In still other embodiments n is at least 2. In some such embodiments the second aromatic ring comprises at least one heteroatom and/or a further substituent. In other such embodiments the substituent is selected from the group of a halogen, an alkyl chain, an alkoxy (e.g., OMe), an acetyl (Ac), an N-acetyl, an amine, an alkyl amine (e.g., $N(Me)_2$), and a sulfide (e.g., SMe).

In yet other embodiments the bifunctional monomer further comprises an additional benzoquinoline subunit. In some such embodiments the additional benzoquinoline subunit further comprises at least one heteroatom and/or an additional substituent group selected from the group of a halogen, an alkyl chain, an alkoxy (e.g., OMe), an acetyl (Ac), an N-acetyl, an amine, an alkyl amine (e.g., $N(Me)_2$), and a sulfide (e.g. SMe).

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein:

FIGS. 1B1 to 1B3 provide synthesis schemes for conventional Sonogashira, Suzuki-Miyaura and Friedlander polyquinoline synthetic routes.

FIGS. 1C1 to 1C2 provide synthesis schemes for molecular architectures available using a conventional Friedlander polyquinoline synthetic route.

FIGS. 2A1 to 2A6 provide an overview of synthesis targets utilizing an aza-Diels-Alder (Povarov) reaction in accordance with embodiments of the invention.

FIGS. 4B1 to 4B4 provide molecular diagrams for bifunctional monomers and polyquinolines in accordance with embodiments of the invention.

FIG. 6 provides a synthesis scheme for an AA/BB-type aza-Diels-Alder biquinoline synthetic route in accordance with embodiments of the invention.

DETAILED DESCRIPTION OF THE INVENTION

Turning now to the drawings, novel quinolines, polyquinolines, polybenzoquinolines, molecular segments of fullerenes (e.g., rubicenes) and graphene nanoribbons (e.g., and tetrobenzopentacenes), and graphene nanoribbons, and processes for producing such materials are provided. In many embodiments the processes utilize a form of an aza-Diels-Alder (Povarov) reaction to form quinolines, polyquinolines, benzoquinolines, polybenzoquinolines and oligobenzoquinolines. In some such embodiments polyquinolines thus produced are used to form molecular segments, graphene nanoribbon precursors and graphene nanoribbons. In many such embodiments the graphene nanoribbone precursors are formed from polybenzoquinolines and/or oligobenzoquinolines.

Figure 1A:
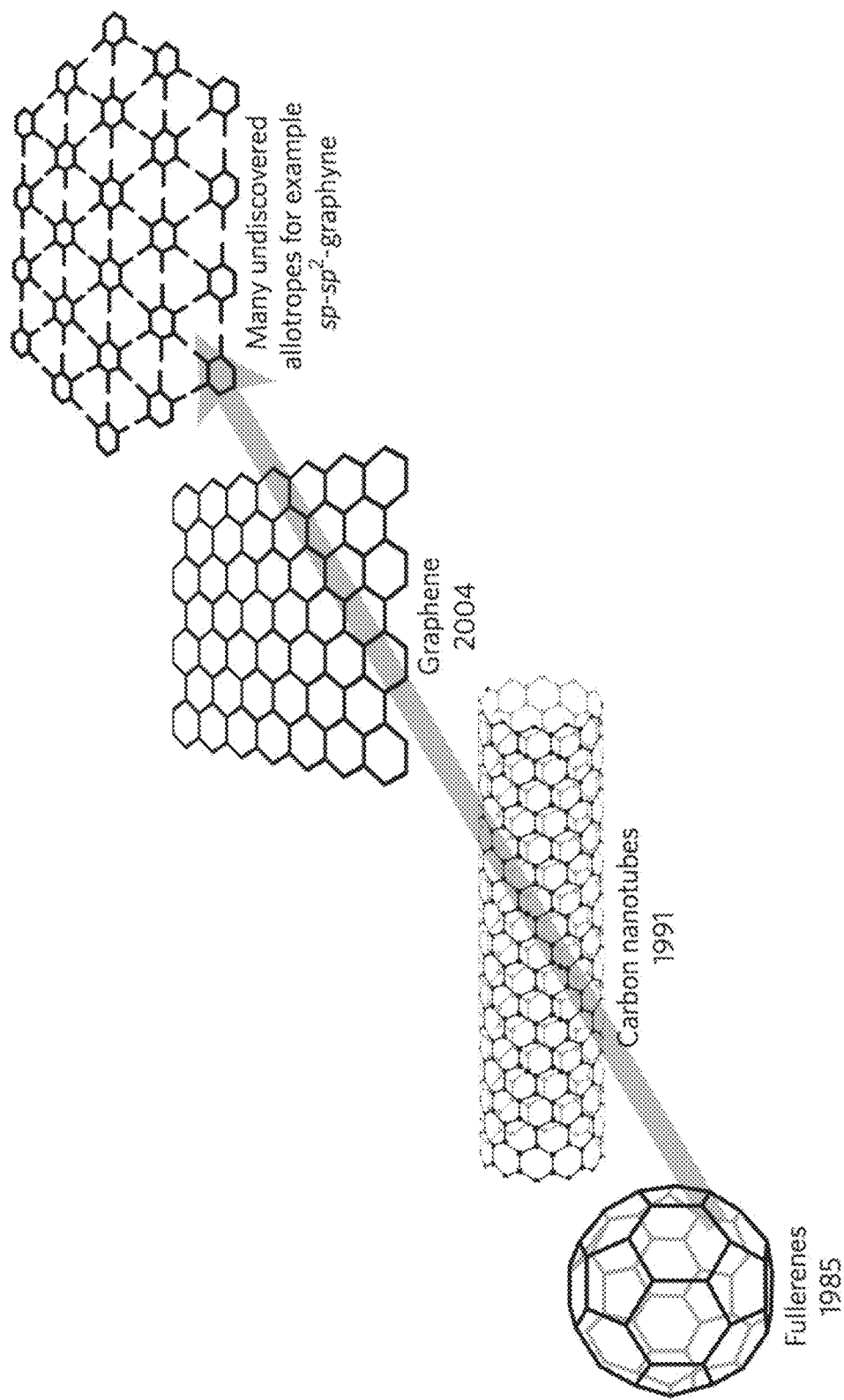
FIG. 1A provides schematics of fullerenes, carbon nanotubes and graphene.
Figure 6:
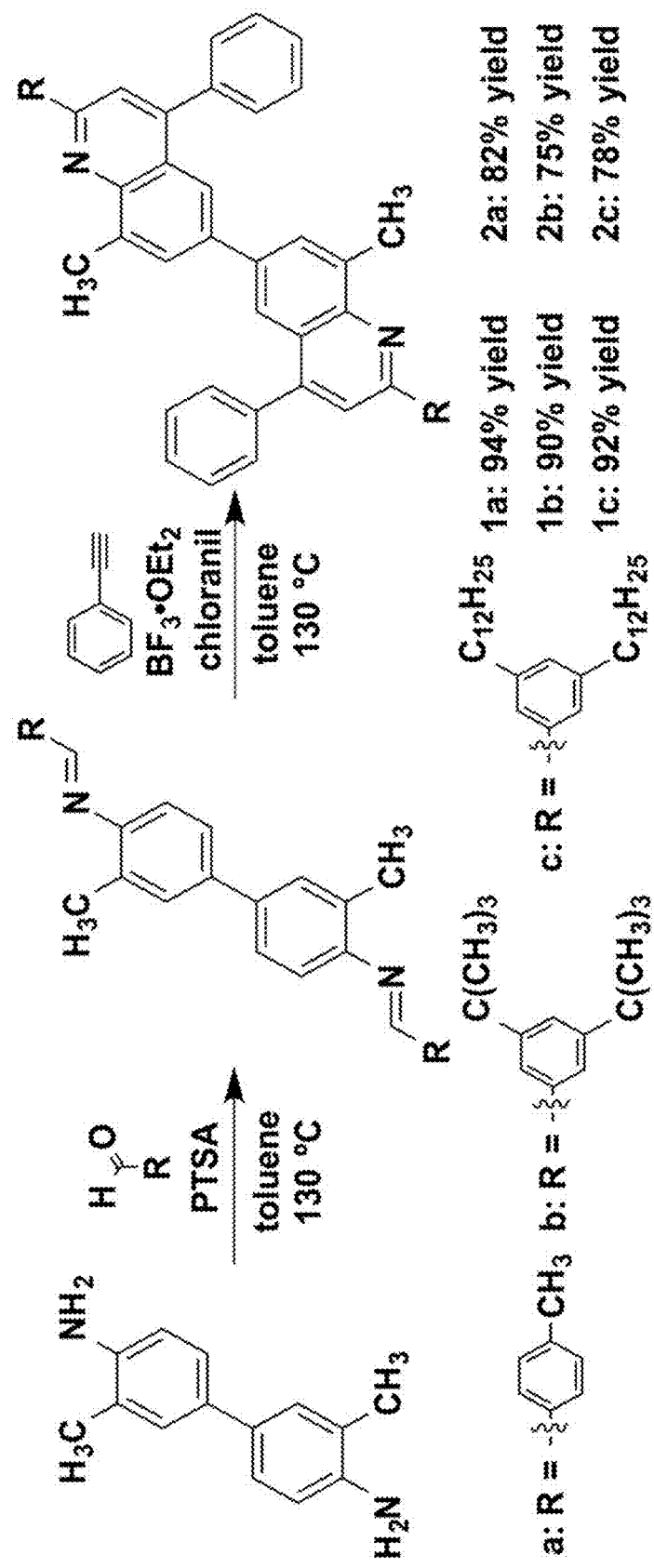

Many embodiments of the aza-Diels-Alder (Povarov) reaction utilize imine and alkynyl functionalized aromatic reagents in the presence of a Lewis acid mediator and a sacrificial oxidant to form the novel quinolines, polyquinolines, polybenzoquinolines, molecular segments, and graphene nanoribbons, as illustrated in FIGS. 2A1 to 2A6. In some such embodiments the imine and alkynyl functional groups may be collocated on a single bifunctional monomer. In other embodiments the imine and alkynyl functional groups may be located on separate compounds. These reagents may be further substituted as desired (e.g., alkyls, aromatic groups, heteroatoms, etc.) to yield functionalized quinolines, biquinolines, benzoquinolines and polyquinolines that may then be used to form graphene ribbons.

Figure 2B:
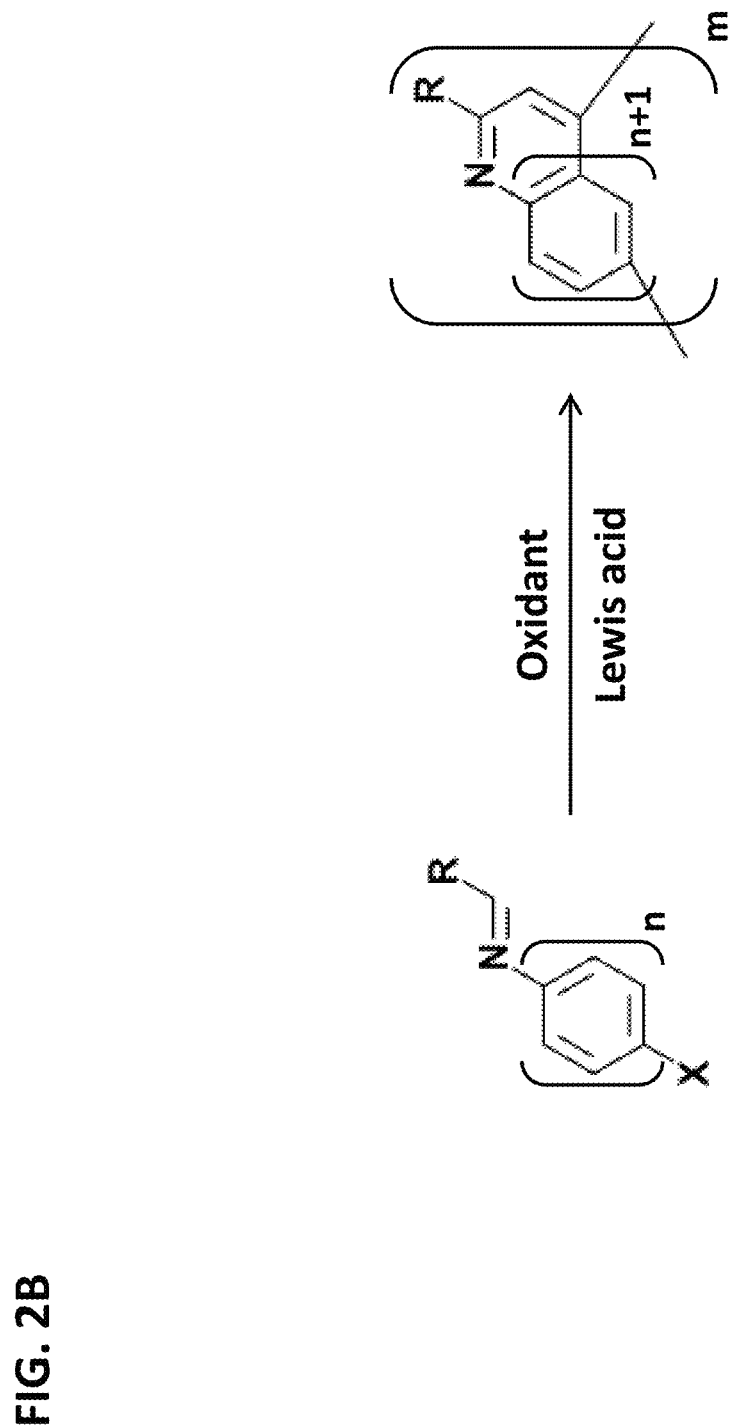
FIG. 2B provides a synthesis scheme for an aza-Diels-Alder polyquinoline synthetic route in accordance with embodiments of the invention.

An exemplary synthesis scheme in accordance with many embodiment is provided in FIG. 2B. In some such embodiments the reaction proceeds by either reacting a halogenated monomer with an R-group containing alkynyl or by polymerizing a bifunctional monomer (i.e., a monomer having both alkynyl and imine functional groups co-located on a single monomer molecule) in the presence of a Lewis acid mediator and a sacrificial oxidant such that the imine group of one bifunctional monomer reacts with the alkyne group of another bifunctional monomer, yielding a polyquinoline product wherein the nitrogen from the imine group is incorporated into each of the multicyclic quinoline rings of the polyquinoline. In some such embodiments:

X may be a halogen or an alkynyl;

n and m may be an integer of at least 1; and

R is an unsubstituted or substituted aromatic ring.

In other embodiments the aromatic ring of R may contain at least one heteroatom and may be further substituted with at least one of the following a halogen, an alkyl chain, an alkoxy (e.g., OMe), an acetyl (Ac), an N-acetyl, an amine, an alkyl amine (e.g., $N(Me)_2$), and a sulfide (e.g., SMe). In yet other embodiments the method further includes terminating the polymerization reaction to obtain a polyquinoline of specified length (designated by m in FIG. 2B). In still yet other embodiments n is at least 2 such that a polybenzoquinoline product may be formed. In some such embodiments the second aromatic ring may comprise a heteroatom and a further substituent. In some other such embodiments the further substituent is selected from the group of a halogen, an alkyl chain, an alkoxy (e.g., OMe), an acetyl (Ac), an N-acetyl, an amine, an alkyl amine (e.g., $N(Me)_2$), and a sulfide (e.g., SMe). In still other such embodiments the bifunctional monomer further may comprise an additional benzoquinoline subunit. In yet other such embodiments the additional benzoquinoline subunit may further comprise a heteroatom and an additional substituent group selected from the group of a halogen, an alkyl chain, an alkoxy (e.g., OMe), an acetyl (Ac), an N-acetyl, an amine, an alkyl amine (e.g., $N(Me)_2$), and a sulfide (e.g., SMe). In still yet other embodiments the individual quinolines of the polyquinoline are linked at the 4 and 6 positions.

In various other embodiments a cyclodehydrogenation reaction may be used to transform polyquinoline and/or polybenzoquinoline precursors into molecular segments and/or graphene nanoribbons.

The aza-Diels-Alder reactions described herein may be conducted under a variety of reaction conditions, including, temperatures (e.g., 30 to 130° C.), reaction times (e.g., 2 to 50 hours), etc. using a variety of Lewis acids (e.g., $BF_3.OEt_2$), non-polar solvents (e.g., toluene) and oxidants (e.g., chloranil). Likewise, the cyclodehydrogenation reactions described herein may be conducted under a variety of reaction conditions, including, various metallic catalysts (e.g., Pd and/or Fe). Further purification steps may also be incorporated in the methods to improve the reactant yield and purity (e.g., filtration, precipitation, chromatography, etc.).

These and other aspects of the embodiments will be described in greater detail in the following sections of the disclosure.

Synthesis of Quinolines and Polyquinolines

Quinoline is a heterocyclic aromatic organic compound with the chemical formula $C_9H_7N$. Quinoline itself has few applications, but many of its derivatives are useful in diverse applications. Polyquinolines are conjugated polymers of quinolines and are compounds with interesting electronic and optical products. However, until recently their synthesis has been constrained to cumbersome methods with limited flexibility for the synthesis of diverse compounds. Thus, there is a need in the art for facile methods of quinoline and polyquinoline synthesis that can be utilized to make a broad range of end products. Accordingly, many embodiments are provided which disclose novel quinoline and polyquinoline synthetic methods that enable the easy production of diverse quinoline and polyquinoline end products from inexpensive, commercially available starting materials.

Various embodiments of the synthetic methods for quinolines and polyquinolines incorporate an aza-Diels-Alder (Povarov) reaction. A set of exemplary synthesis scheme for such a reaction are provided in FIGS. 2A1 to 2A6. As shown, in many such embodiments the aza-Diels-Alder synthetic methods encompass a two-step process whereby an aromatic compound having an aldimine functional group (e.g., a Schiff base) is reacted with a compound having an alkyne functional group in the presence of a Lewis acid mediator. In some embodiments the reaction further incorporates a sacrificial oxidant to prevent endogenous consumption of imine during the process. In embodiments where quinolines are to be produced the aromatic aldimine and alkyne functional groups are located on separate reagents. In other embodiments where polyquinolines are to be produced the aromatic aldimine and alkyne functional groups are co-located on a single bifunctional monomer. In many such embodiments the bifunctional monomer comprises a Schiff base having an alkyne substituent. Various embodiments methods implement an AB-type aza-Diels-Alder reaction to form quinolines and polyquinolines. In other embodiments methods implement an AA/BB-type aza-Diels Alder reaction to form biquinolines and polyquinolines. In still other embodiments modular benzo-, polybenzo- and oligobenzoquinolines are produced using an aza-Diels-Alder reaction. In some such embodiments, methods allow the incorporation of a variety of functional groups (R-groups) onto the aldimine/alkyne reagents or bifunctional monomer, and subsequently onto the polyquinoline ring produced therefrom.

Quinoline Synthesis

Turning now to methods for producing quinolines and quinolines produced therefrom, embodiments are provided that implement an aza-Diels-Alder (Povarov) reaction to yield a facile means of producing a wide-variety of quinoline compounds. An exemplary embodiment of such a process is shown schematically in FIG. 3A. As shown, in many embodiments a two-step process is utilized to produce quinolines from commercially available reactants. In many such embodiments the first-step comprises the production of one or more Schiff bases 1a and 1b from an amine substituted aromatic compound and an aldehyde containing a desired substituent group (hereinafter referred to as an "R-group") utilizing standard protocols as will be known to those skilled in the art. (See, e.g., Taguchi, K. and Westheimer, F. H. *J. Org. Chem.* 1971, 36, 1570-1572, the disclosure of which is incorporated herein by reference.) In many embodiments the R-group at least comprises an aromatic ring (e.g., a benzoaldehyde) or an alkyl chain, and in many other embodiments the R-group is an aromatic ring having an alkyl substituent. The product of this initial reaction according to embodiments is a Schiff base having an aromatic substituent (e.g., an imine substitute aromatic structure) that is functionalized with the R-group.

In the second-step according to embodiments a compound comprising at least an alkyne functional group is reacted with the Schiff base 1a and/or 1b in the presence of a Lewis acid mediator. In accordance with embodiments of the process the resulting condensation results in the addition of the Schiff base with the alkyne substitute compound to form a quinoline heterocyclic ring 2a and/or 2b wherein the R-group is substituted on the heterocyclic ring ortho to the nitrogen, as shown in FIG. 3A.

Figure 3A:
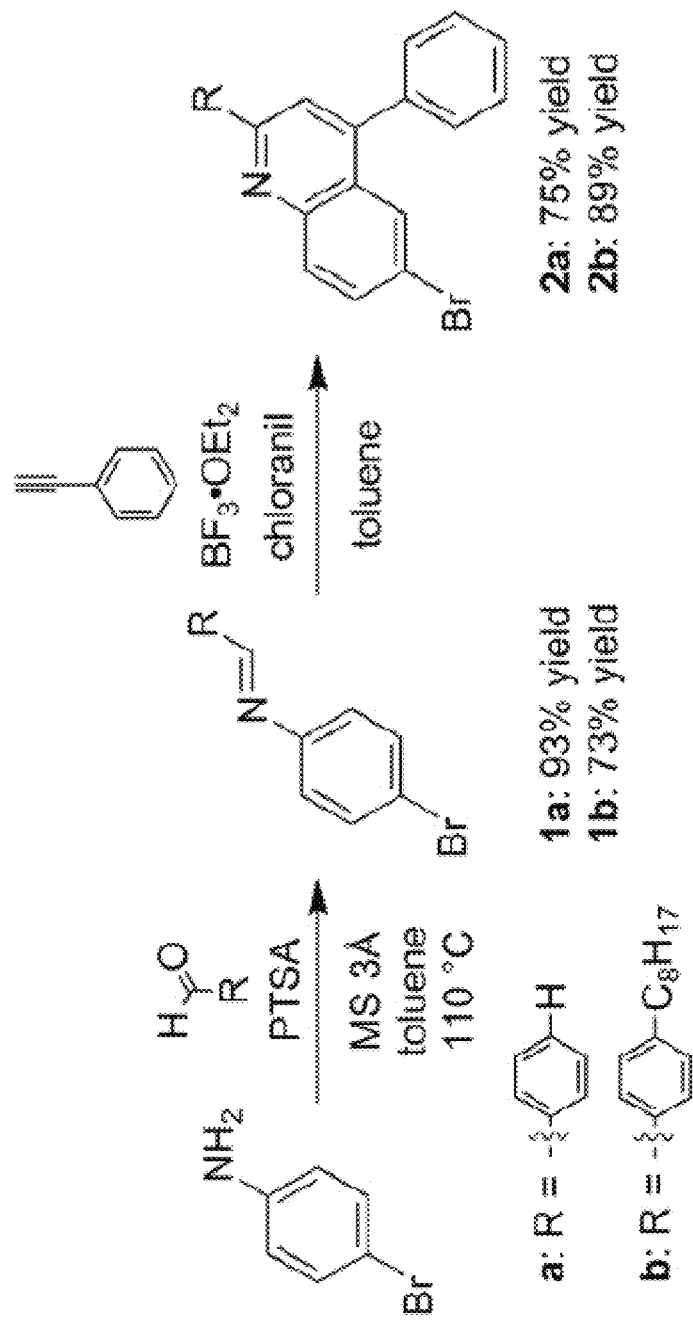
FIG. 3A provides a synthesis scheme for an aza-Diels-Alder quinoline synthetic route in accordance with embodiments of the invention.

It should be understood that although specific compounds are shown in the reaction diagram provided in FIG. 3A, these species are merely exemplary. It will be understood that the synthesis scheme may be generalized by altering the nature of the aromatic aldimine, the aldehyde and the alkyne containing reagents. For example, although an amine substitute benzene ring is shown as one of the initial reagents in FIG. 3A, it should be understood that any suitable amine substitute aromatic may be used. Likewise, although the R-groups attached to the aldehyde reagent are shown to be functionalized benzene, it should be understood that any suitable substituent may be used in accordance with embodiments, including, for example, alternative substituted aromatic groups. In addition, although the R-group in the exemplary embodiment provided in FIG. 3A comprises a further 8-carbon alkyl substituent attached to the aromatic group, it should be understood that the R-group in accordance with embodiments may further comprise one or more para- or meta-substituted substituents, such as, for example alkyl chains of a suitable length, heteroatoms or other functional groups. In some embodiments, for example, an alkyl chain of 2 to 50 carbons is used, while in other embodiments an alkyl chain of 5 to 10 carbons is used. In many embodiments the R-group may be chosen to selectively engineer one or more properties of the quinoline. For example, although not to be bound by theory, generally the longer the alkyl chain(s), the more soluble the end products will be, as may be understood by one of ordinary skill in the art. Finally, although phenylacetylene is used as an example of a suitable alkyne containing molecule, it should be understood that any suitable alkyne containing molecule may be thus provided. Thus, by altering the functional groups of the R-group or alkyne any number of quinolones quinolines may be produced, such as, for example, bicyclic, tricyclic, and other multicyclic aromatic or heteroaromatic structures, for example with any number of additional substituent functional groups. Including, for example, aromatic heteroatoms (e.g., N, S, etc.) and substituent halogens (e.g., F, Cl, etc.), alkyl chains, alkoxys (e.g., OMe), acetyls, N-acetyls, amines, alkyl amines (e.g., $N(Me)_2$), and sulfides (e.g., SMe), among others, all of which may be incorporated via the aromatic aldimine and/or alkyl reagents.

Figure 3B:
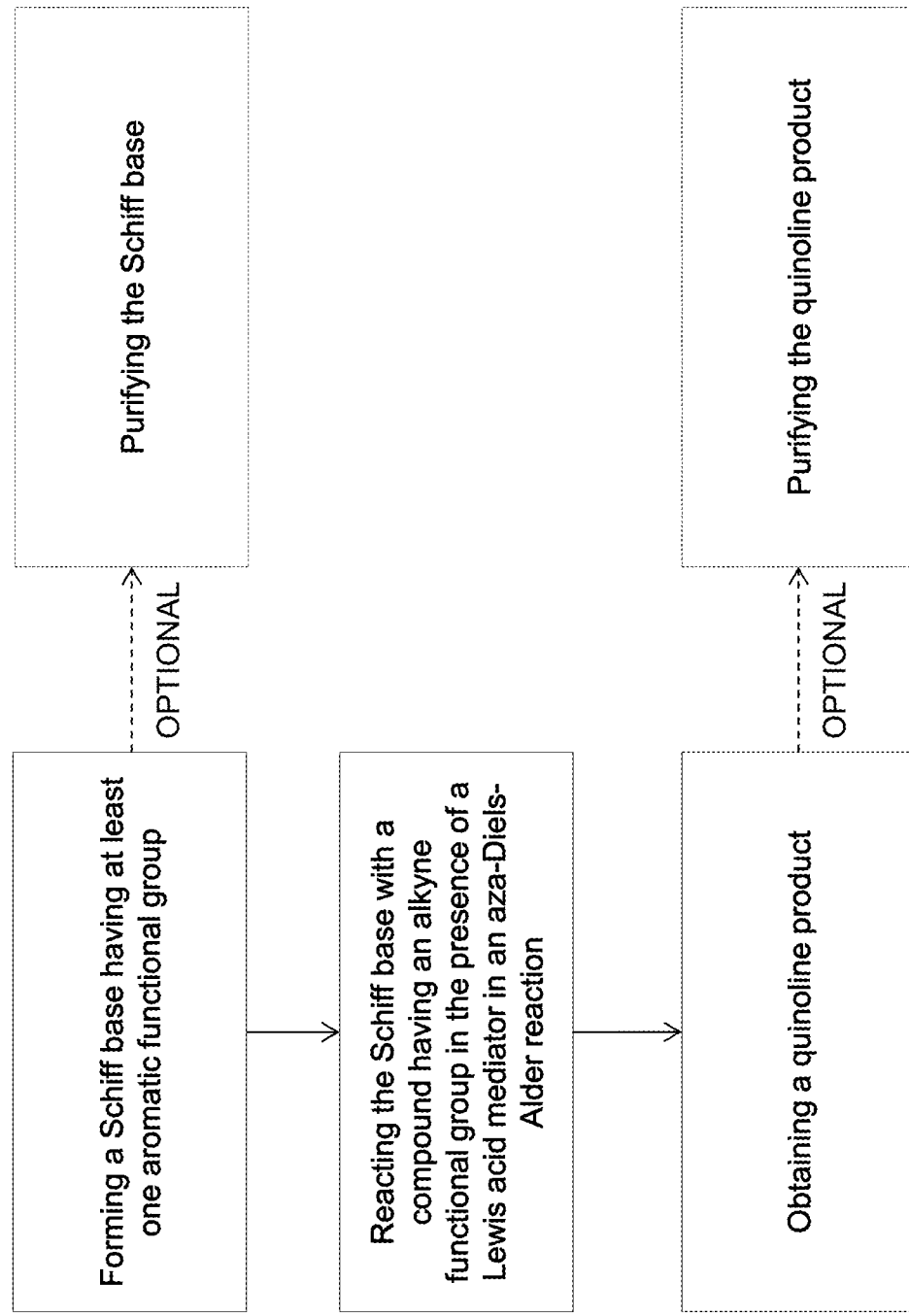
FIG. 3B provides a flow-chart for a method for synthesizing quinolines in accordance with embodiments of the invention.

A flow-chart is provided in FIG. 3B that provides a flow-chart for forming quinolines in accordance with embodiments. As shown, in many embodiments as an initial step a Schiff base having an aromatic functional group is formed from commercially available reagents (e.g., an amine functionalized aromatic and a substituted aldehyde). The Schiff base is then reacted with an alkyne substituted compound in the presence of a Lewis acid mediator to form quinoline via a Povarov reaction. Finally, purification of one or both of the Schiff base or the final quinoline product may optionally be performed. Such purification may be performed by any suitable method, such as, for example, filtering, chromatography, and precipitation, as will be described in greater detail in the Exemplary Embodiments, below. Some exemplary embodiments of purification procedures include, for example, filtering the reaction mixture through celite and solvent removal, for example by vacuum, or flash chromatography using deactivated silica gel with pure hexanes as the mobile phase.

Although specific embodiments of reaction conditions, reagents and solvents will be described in detail in the Exemplary Embodiments, it will be understood that there is a great deal of flexibility in such parameters. For example, the first reaction may comprise the use of any suitable non-polar solvent such as, for example, toluene. The reaction may be carried out at any suitable temperature, such as, for example, from 90-150° C. In some specific embodiments the reaction may be carried out at a temperature of around 130° C. In some embodiments the reaction may be facilitated utilizing a molecular sieve to remove side products and water, when forming the Schiff base. Any suitable mesh size for the molecular sieve may be used, such as, for example such as, for example a 3 Angstrom molecular sieve. Any reaction time may be used, for example reaction times of 4 to 50 hours are used in some exemplary embodiments, while in others the exemplary reaction time is 16 hours. Likewise, although a $BF_3$—$OEt_2$ Lewis acid is provided in the exemplary embodiments, it should be understood that any number of Lewis acids known to mediate the Povarov reaction may be used. (See, e.g., Kouznetsov, V. V. *Tetrahedron* 2009, 65, 2721-2750, the disclosure of which is incorporated herein by reference.) Finally, the exemplary embodiments show the condensation reaction being performed in the presence of a sacrificial oxidant, such as, for example, chloranil. It should be understood that any suitable sacrificial oxidant may be used. (See, e.g., *Chloranil Encyclopedia of Reagents for Organic Synthesis*, John Wiley & Sons; Braude, E. A., et al. *J. Chem. Soc.* 1960, 32, 49-3257; Huisgen, R., et al. *Tetrahedron* 1962, 17, 3-29; Fryer, R. I., et al. *J. Org. Chem.* 1970, 35, 2455-2459; and Landberg, B. E. and Lown, J. W. *J. Chem. Soc., Perkin Trans.* 11975, 1326-1333, the disclosure of which is incorporated herein by reference.)

As will be understood, regardless of the specific reagents and techniques used it will be understood that the methods for forming quinolines in accordance with embodiments provides a simple two-step aza-Diels-Alder synthetic route that requires only commercially available starting materials. In addition, the procedures allow for the use of a large number of commercially available benzaldehyde derivatives (e.g., having various R-groups), which can provide facile access to a diverse library of new quinoline materials.

Polyquinoline Synthesis (AB-Type Polymerization)

Turning now to methods for producing polyquinolines and polyquinolines produced therefrom, embodiments are provided that implement an aza-Diels-Alder (Povarov) reaction to yield a wide-variety of polyquinoline-type compounds. An exemplary embodiment of such a process is shown schematically in FIG. 4A. It will be understood that the synthesis scheme may be generalized by altering the nature of the aromatic aldimine, the aldehyde and the alkyne containing reagents. As shown, in many embodiments a two-step process is utilized to produce polyquinolines from commercially available reactants. In many such embodiments the first-step comprises the production of a Schiff base 3 having both alkyne and aldimine functional groups, which will be referred to herein as a "bifunctional monomer." Although the embodiment provided in FIG. 4A shows a specific bifunctional AB-type monomer, as will be described in greater detail, these bifunctional monomers may take many forms and types, including, for example, aza-Diels-Alder AA/BB-type monomers.

In this first reaction, an aldehyde functionalized R-group is combined with a bifunctional aromatic compound having at least amine and alkyne functional groups (e.g., alkyne functionalize aniline). In this reaction, the aldehyde on the R-group facilitates bonding of the R-group to the nitrogen on the bifunctional aromatic compound. As illustrated in FIG. 4A, the resulting product of the first reaction comprises the bifunctional monomer with its nitrogen substituent double bonded to the aromatic constituent of the R-group, such that the bifunctional monomer 3 comprises at least one aromatic ring (e.g. a benzene ring or the like), with an imine substituent and a substituted alkyne. Although the exemplary embodiment shows the alkyne being para-substituted, it will be understood that in other embodiments meta-substituted alkyne groups may also be used.

Figure 4A:
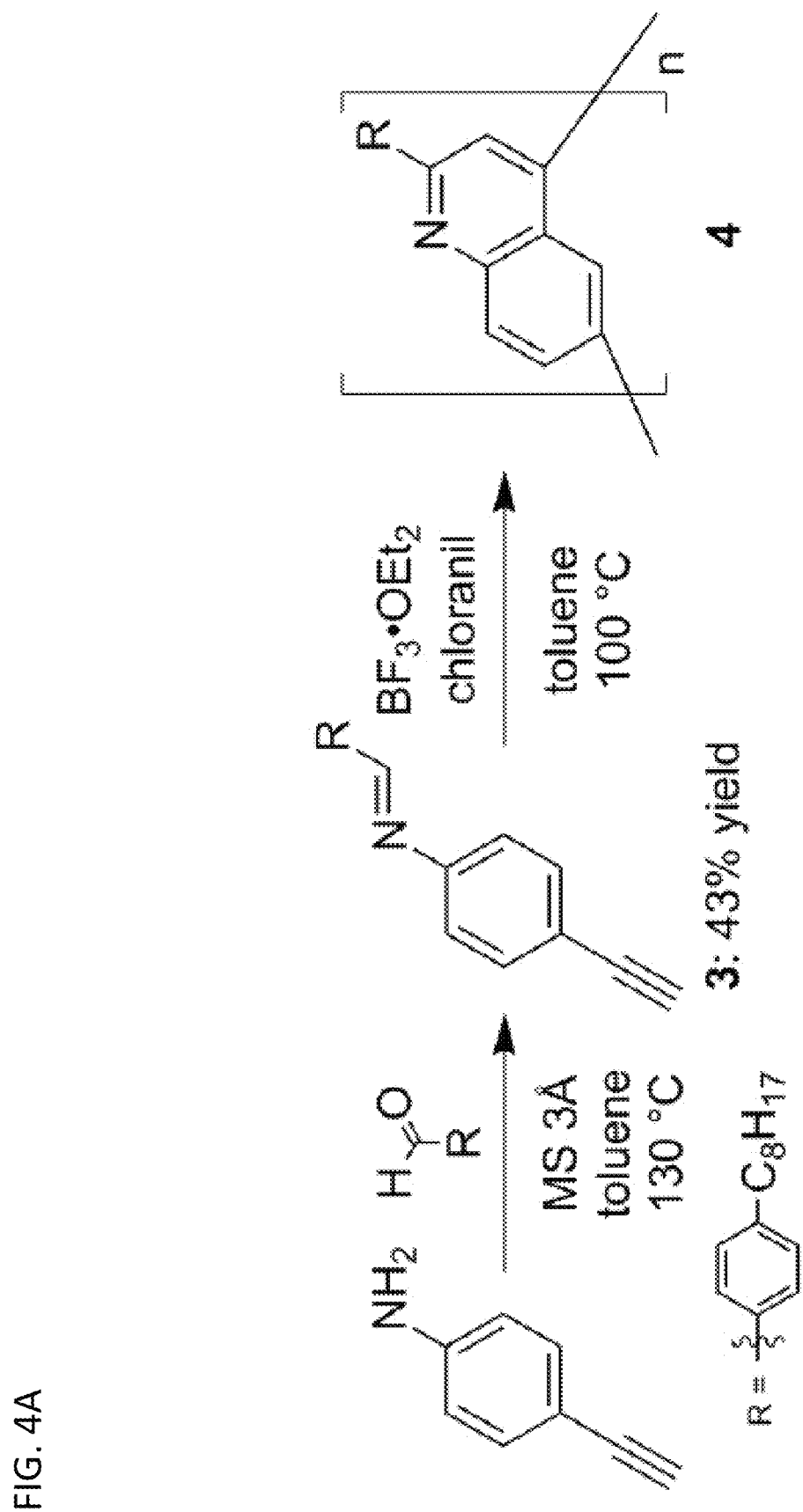
FIG. 4A provides a synthesis scheme for an aza-Diels-Alder polyquinoline synthetic route in accordance with embodiments of the invention.

Although in the exemplary embodiment of the process shown in FIG. 4A the bifunctional monomer comprises at least one benzene ring with an imine substituent and a para-substituted alkyne, it should be understood that alternative arrangements might be used with the reaction described in accordance with embodiments. For example, the monomer may comprise any suitable aromatic group. Moreover, the bifunctional monomer may comprise bicyclic, tricyclic, and other multicyclic aromatic structures, such as are depicted, for example, in monomers E1 to E4 provided in FIG. 4B. In addition, although the R-group in the exemplary embodiment provided in FIG. 4A comprises a further 8-carbon alkyl substituent, it should be understood that the R-group in accordance with embodiments may further comprise one or more para- or meta-substituted substituents, such as, for example alkyl chains of a suitable length. In some embodiments, for example, an alkyl chain of 2 to 50 carbons is used, while in other embodiments an alkyl chain of 5 to 10 carbons is used. In many embodiments the R-group may be chosen to selectively engineer one or more properties of the end product. For example, although not to be bound by theory, generally the longer the alkyl chain(s), the more soluble the end products will be, as may be understood by one of ordinary skill in the art. Finally, as shown in FIGS. 4B1 to 4B4, many other substitutions and substituents may be made to the bifunctional monomers in accordance with embodiments, including the introduction of halogens (e.g., F, Cl, etc.), alkyl chains, alkoxys (e.g., OMe), acetyls, N-acetyls, amines, alkyl amines (e.g., $N(Me)_2$), and sulfides (e.g., SMe), among others.

As will be understood, regardless of the specific reagents and techniques used methods for forming bifunctional monomers in accordance with embodiments provide a simple synthetic route that requires only commercially available starting materials. In addition, the procedures allow for the use of a large number of commercially available benzaldehyde derivatives (e.g., for use as R-groups), which provides facile access to a diverse library of alternative bifunctional monomer compounds.

Figure 4C:
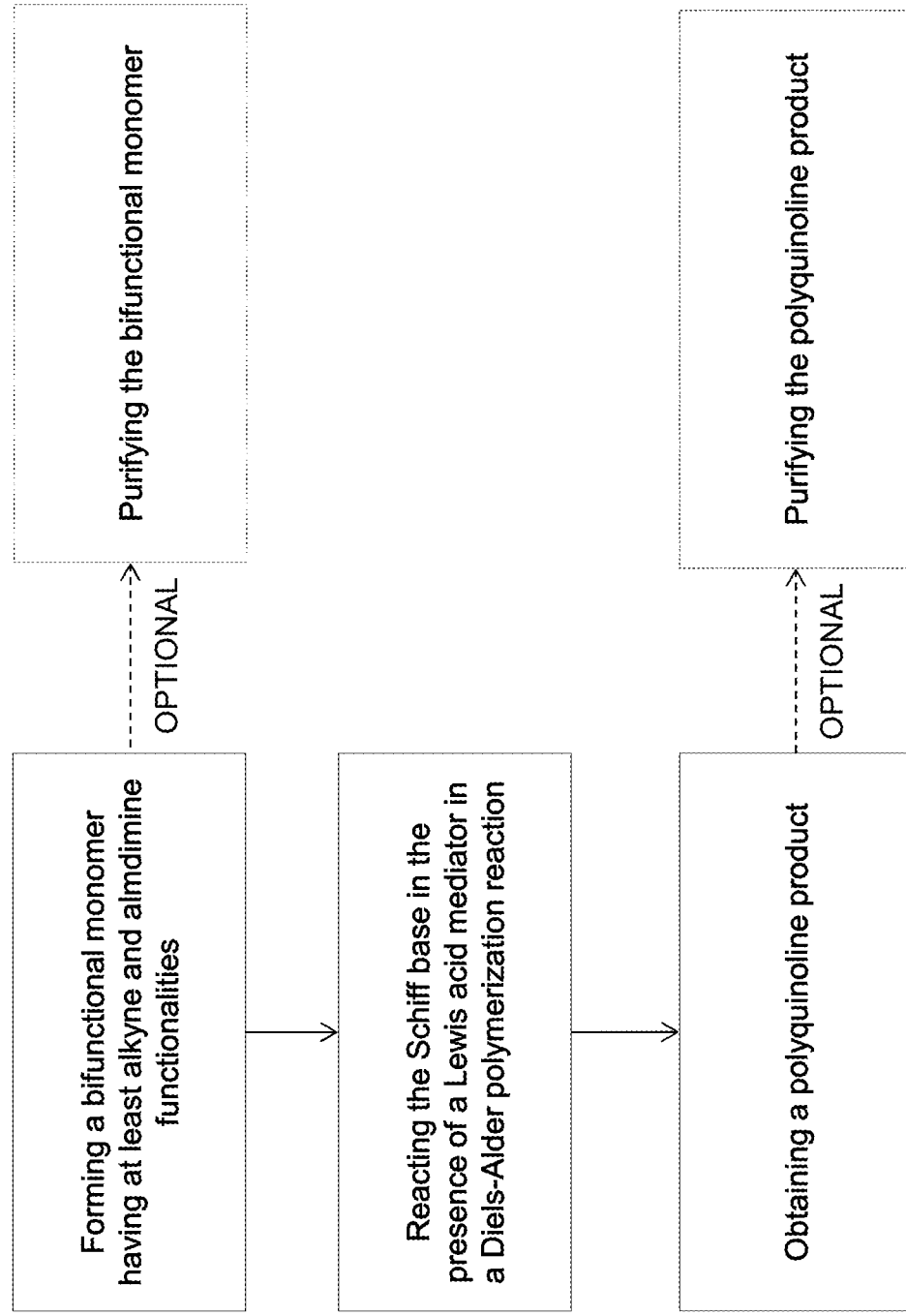
FIG. 4C provides a flowchart of a process for producing polyquinoline in accordance with embodiments of the invention.

As shown in the flow-chart in FIG. 4C, the first-step of the reaction in accordance with embodiments may be completed by combining the reactants (e.g., R-group and bifunctional aromatic) into solution with a suitable polar solvent (e.g., toluene) to form the bifunctional monomer. The reactants are allowed to react under suitable conditions (e.g., reaction temperature such as 90-150° C. for 16 hours) followed by cooling the reaction vessel to room temperature. Purification of the bifunctional monomer may then be performed prior to performance of the second reaction.

Although specific embodiments of reaction conditions, reagents and solvents of this first-step of the reaction will be described in detail below, it will be understood that there is a great deal of flexibility in such parameters. For example, the first reaction may comprise the use of any suitable non-polar solvent such as, for example, toluene. The reaction may be carried out at any suitable temperature, such as, for example, from 90-150° C. In some specific embodiments the reaction may be carried out at a temperature of around 130° C. In some embodiments the reaction may be facilitated utilizing a molecular sieve to remove side products and water, when forming the bifunctional monomer. Any suitable mesh size for the molecular sieve may be used, such as, for example such as, for example a 3 Angstrom molecular sieve. Any reaction time may be used, for example reaction times of 4 to 50 hours are used in some exemplary embodiments, while in others the exemplary reaction time is 16 hours.

Turning to the second-step of the method, as shown in FIG. 4A, in many embodiments a polyquinoline is produced from the bifunctional monomer via a Diels-Alder AB-type polymerization reaction wherein the imine group of one bifunctional monomer combines with the alkyne group of a second bifunctional monomer. As shown in the reaction diagram, the second-step of the reaction according to embodiments results in the incorporation of the nitrogen from the imine group into a multicyclic quinoline group, with the R-group as a substituent, adjacent (i.e., ortho) to the nitrogen. In many embodiments this allows for polyquinolines that are linked at the 4,6 positions of the quinoline ring, as shown for example in FIG. 4A.

As shown in the diagram provided in FIG. 4A, the bifunctional Schiff base monomer 3 is reacted in the presence of a Lewis acid mediator to form the polyquinoline 4 via an AB-type Diels-Alder polymerization (Povarov) reaction. In embodiments of the process this second polymerization step may be halted and the reaction products isolated or purified using any means known in the art. For example, the reaction may be halted by cooling the reaction mixture to room temperature and dilution with a suitable solvent, such as, for example, $CH_2Cl_2$. Reagents may be quenched with saturated $NaHCO_3$ and the organics may then be washed with saturated $NaHCO_3$. Finally, purification of the polyquinolines may then optionally be performed. Purification may be performed by any suitable method, such as, for example, filtering, chromatography, and precipitation, as will be described in greater detail in the Exemplary Embodiments, below. Some exemplary embodiments of purification procedures include, for example, filtering the reaction mixture through cotton and solvent removal, for example by vacuum, or size-exclusion chromatography where the mixture is dissolved in $CHCl_3$ and, after being purified, is precipitated from ethanol to yield the product. Using purification techniques in accordance with such embodiments it is possible to obtain nearly monodisperse polyquinoline products.

Although specific embodiments of reaction conditions, reagents and solvents of this second-step of the reaction will be described in detail in the Exemplary Embodiments, it will be understood that there is a great deal of flexibility in such parameters. For example, the first reaction may comprise the use of any suitable non-polar solvent such as, for example, toluene. The reaction may be carried out at any suitable temperature, such as, for example, from 70-130° C. In some specific embodiments the reaction may be carried out at a temperature of around 110° C. Any reaction time may be used, for example reaction times of 2 to 50 hours are used in some exemplary embodiments, while in others the exemplary reaction time is 24 hours. Likewise, although a $BF_3$—$OEt_2$ Lewis acid is provided in the exemplary embodiments, it should be understood that any number of Lewis acids known to mediate the Povarov reaction may be used. (See, e.g., Kouznetsov, V. V. *Tetrahedron* 2009, 65, 2721-2750, the disclosure of which is incorporated herein by reference.) Finally, the exemplary embodiments show the condensation reaction being performed in the presence of a sacrificial oxidant, such as, for example, chloranil. It should be understood that any suitable sacrificial oxidant may be used. (See, e.g., *Chloranil Encyclopedia of Reagents for Organic Synthesis*, John Wiley & Sons; Braude, E. A., et al. *J. Chem. Soc.* 1960, 32, 49-3257; Huisgen, R., et al. *Tetrahedron* 1962, 17, 3-29; Fryer, R. I., et al. *J. Org. Chem.* 1970, 35, 2455-2459; and Landberg, B. E. and Lown, J. W. *J. Chem. Soc., Perkin Trans.* 11975, 1326-1333, the disclosure of which is incorporated herein by reference.)

Regardless of the specific reaction conditions used, it should be understood that utilizing the bifunctional monomers and AB-type Diels-Alder polymerization methods described herein in accordance with embodiments allows for the facile production of a wide-variety of polyquinolines. In particular, as the structure of the polyquinolines in accordance with embodiments is determined by the structure of the bifunctional monomer including the substituent R-group, a number of diverse starting materials may be used in order to synthesize a large number of different polyquinoline materials as illustrated by exemplary monomers E1 to E4 and associated polyquinolines in FIGS. 4B1 to 4B4.

Biquinoline and Polyquinoline Synthesis (AA/BB-Type Polymerization)

Although the above discussion focused on the use of an AB-type bifunctional monomer to form polyquinolines via an AB-type Diels-Alder polymerization reaction (i.e. having single imine and alkyne functionalities), other embodiments are directed to methods of forming polyquinolines that implement an AA/BB-type Diels-Alder polymerization (i.e., using reagents having multiple imine and alkyne functionalities).

Figure 5A:
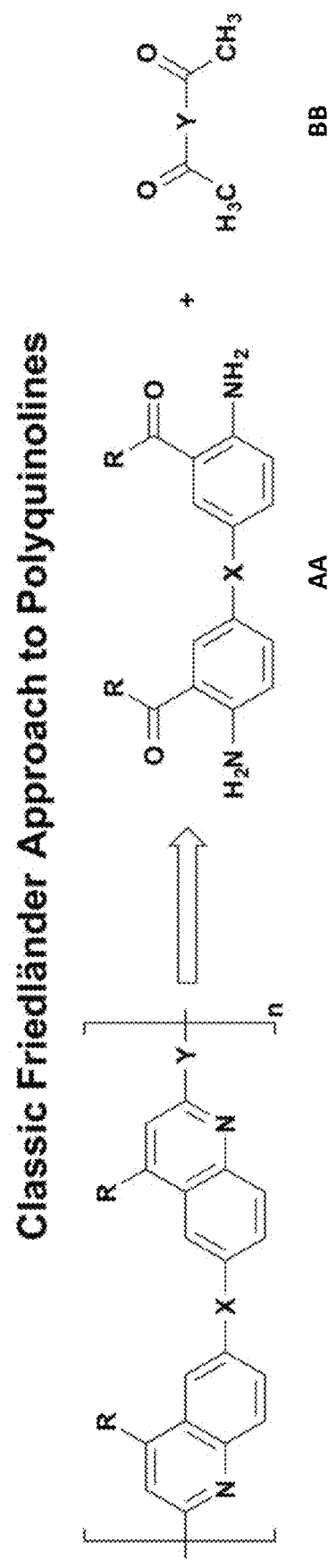
FIG. 5A provides an illustration of a retrosynthetic analysis of an AA/BB-type Friedländer polymerization.

A conventional AA/BB-type polymerization is used in the Friedländer approach, which to date has served as the workhorse of polyquinoline synthesis. (See, e.g., J. K. Stille, *Macromolecules*, 1981, 14, 870; and L. S. Povarov, *Russ. Chem. Rev.*, 1967, 36, 656, the disclosures of which are incorporated herein by reference.) FIG. 5A provides an illustration of a retrosynthetic analysis of a typical AA/BB-type Friedländer polymerization, entailing the reaction of an AA-type bis(amino ketone) monomer with a BB-type bis(keto methylene) monomer. However, as previously discussed, the Friedländer synthesis often requires the resulting polyquinolines to possess complex side chain substituents and cannot provide access to certain backbone architectures (as previously described with respect to FIG. 1C.

Figure 5B:
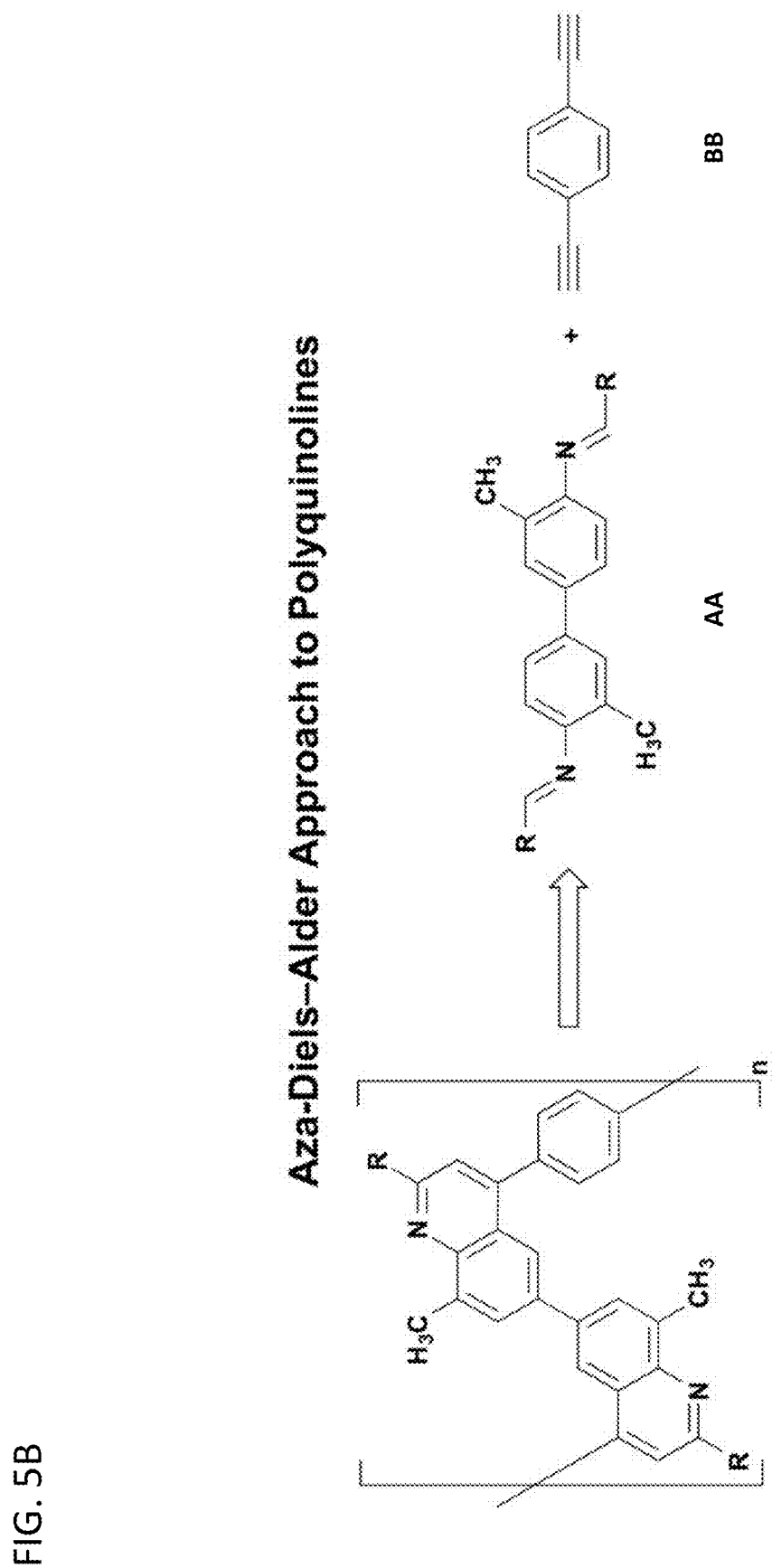
FIG. 5B provides an illustration of a retrosynthetic analysis of an AA/BB-type aza-Diels-Alder polymerization in accordance with embodiments of the invention.

Methods according to embodiments implement an AA/BB-type aza-Diels-Alder polymerization as illustrated in FIG. 5B that provide a simple method of obtaining a wide-variety of polyquinolines, including polyquinolines containing 4,6-linked quinoline subunits. As shown, such embodiments comprise the reaction of an AA-type aromatic diimine monomer with a BB-type dialkynyl monomer to furnish a polyquinoline. It will be understood that the synthesis scheme shown in FIG. 5B is merely exemplary and may be generalized by altering the nature of the AA-type aromatic diimine monomer and the BB-type dialkynyl monomer reagents.

Some embodiments of an AA/BB-type aza-Diels-Alder reaction are utilized to form biquinolines. An exemplary embodiment of such a biquinoline synthetic route is provided in FIG. 6. Again it will be understood that the synthesis scheme shown in FIG. 6 is merely exemplary and may be generalized by altering the nature of the aromatic diimine monomer and the alkynyl monomer reagents. As shown, the process according to embodiments utilizes the aza-Diels-Alder reaction previously described above but wherein bis(aldimines) 1a-c are reacted with an alkyne functionalized compound (e.g. phenylacetylene) in the presence of a Lewis acid mediator (e.g., $BF_3.OEt_2$) and a sacrificial oxidant (e.g., chloranil) to yield biquinolines 2a-c. It should be understood that although certain bis(aldimines) 1a-c are used to form the biquinolines in these exemplary embodiments, any suitable aromatic bisaldimine may be formed in accordance with established methods known to those skilled in the art. (See, e.g., D. J. Dibble, et al., *Macromolecules*, 2015, 48, 557 and D. J. Dibble, et al., *Angew. Chem. Int. Ed.*, 2015, 54, 5883, the disclosures of which are incorporated herein by reference.) In particular, it will be understood that the R-groups used in the bis(aldimines) allow for the installation of nearly arbitrary substituents on the peripheral aromatic (e.g., phenyl) groups, including electron donating, electron withdrawing, sterically hindered and saturated alkyl moieties as will be discussed in greater detail below. As will be discussed in greater detail in the Exemplary Embodiments the AA/BB-type aza-Diels-Alder biquinoline synthesis in accordance with embodiments utilized mild conditions and commercial starting materials to produce regioisomerically pure products in excellent yield.

Figure 7:
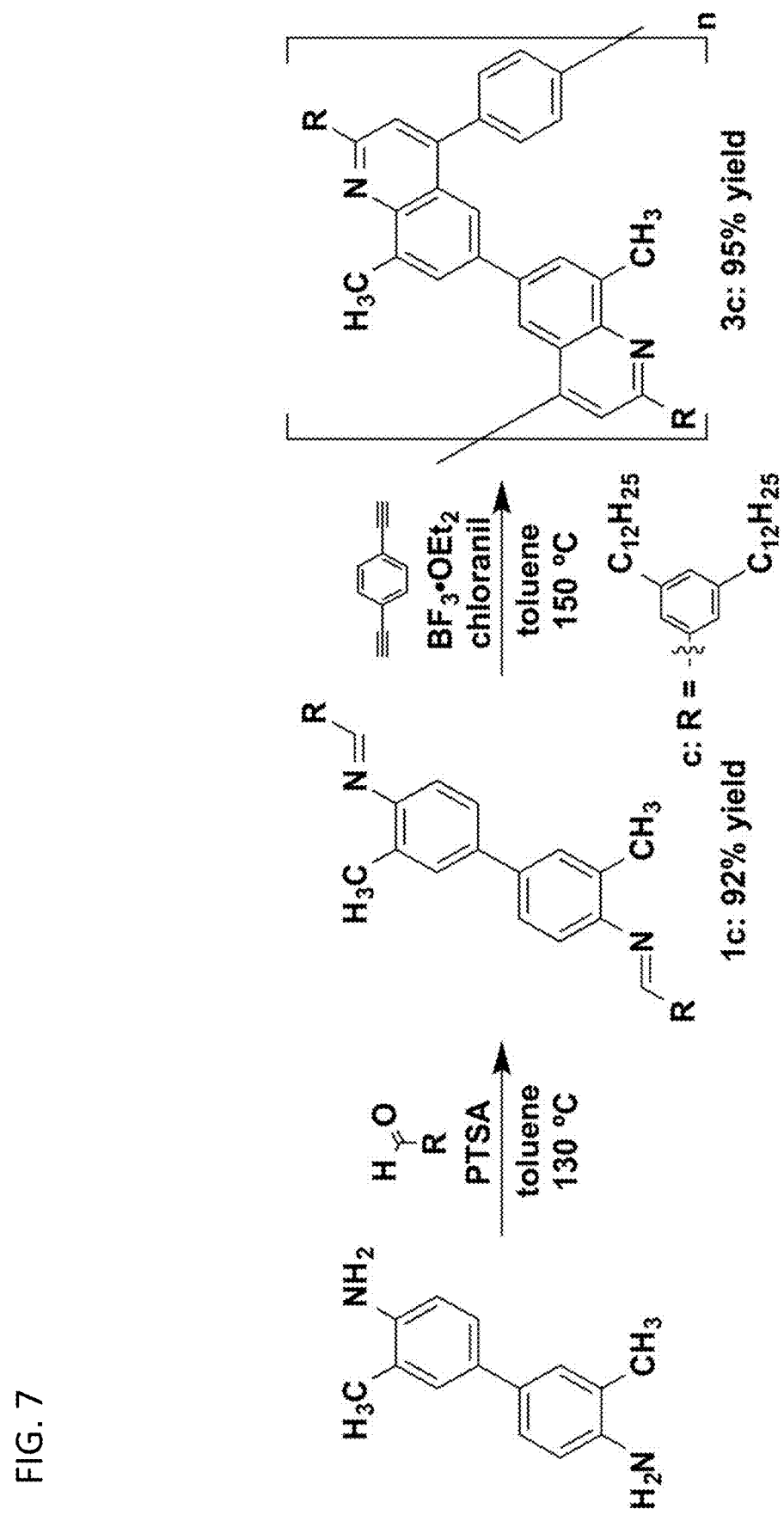
FIG. 7 provides a synthesis scheme for an AA/BB-type aza-Diels-Alder polyquinoline synthetic route in accordance with embodiments of the invention.

Other embodiments implement this AA/BB-type aza-Diels-Alder reaction to prepare polyquinolines, as illustrated in FIG. 7. In these embodiments a diimine 1c is reacted with a dialkynyl (e.g. diethynyl benzene) in an AA/BB-type polymerization under the conditions discussed above for the synthesis of biquinolines to yield the polyquinoline 3c. It will be understood that the synthesis scheme shown in FIG. 7 is merely exemplary and may be generalized by altering the nature of the aromatic diimine monomer and the BB-type dialkynyl monomer reagents, as previously discussed.

In both embodiments of the biquinoline synthesis and the polyquinoline synthesis, it should be understood that alternative reagents might be used with the reaction described in accordance with embodiments. For example, the imine and alkynyl containing reagents may comprise any suitable aromatic group. Moreover, the reagents may comprise bicyclic, tricyclic, and other multicyclic aromatic structures. In addition, although certain R-groups are provided in the exemplary embodiment provided in FIGS. 6 and 7, it should be understood that the R-group in accordance with embodiments may further comprise one or more para- or meta-substituted substituents, such as, for example alkyl chains of a suitable length. In some embodiments, for example, an alkyl chain of 2 to 50 carbons is used, while in other embodiments an alkyl chain of 5 to 10 carbons is used. In many embodiments the R-group may be chosen to selectively engineer one or more properties of the end product. For example, although not to be bound by theory, generally the longer the alkyl chain(s), the more soluble the end products will be, as may be understood by one of ordinary skill in the art. Finally, as will be discussed in greater detail below, many other substitutions and substituents may be made to the bifunctional monomers in accordance with embodiments, including the introduction of heteroatoms into the aromatic structures and substituent halogens (e.g., F, Cl, etc.), alkyl chains, alkoxys (e.g., OMe), acetyls, N-acetyls, amines, alkyl amines (e.g., $N(Me)_2$), and sulfides (e.g. SMe), among others.

Finally, as in the other embodiments thus far discussed, although specific embodiments of reaction conditions, reagents and solvents will be described in detail in the Exemplary Embodiments, it will be understood that there is a great deal of flexibility in such parameters including, for example: the nature of the non-polar solvent (e.g., toluene), the reaction temperature (which may range for example from 70-130° C.), the reaction times (e.g., 2 to 50 hours), the Lewis acid used (e.g., $BF_3$—$OEt_2$), the presence of a sacrificial oxidant (e.g., chloranil), etc.

Benzoquinoline Synthesis

Many embodiments are directed to novel benzoquinolines and polybenzoquinolines and methods of their manufacture. More particularly, embodiments provide methods for the modular synthesis of polybenzoquinolines, which, as will be discussed in greater deal later, constitute a generic class of GNR precursor polymers. In various embodiments a general aza-Diels-Alder reaction for the synthesis of a series of benzoquinoline compounds is provided. In other embodiments an AB-type bifunctional monomer and methods for synthesizing congested polybenzoquinoline via a Diels-Alder-type polymerization reaction from such monomers are also provided. Methods are also provided for the modular preparation of polybenzoquinolines of varying size and having variable peripheral substituents. Finally, molecules and methods are provided in various embodiments capable of serving as precursors to a nitrogen-doped GNR.

Figure 8A:
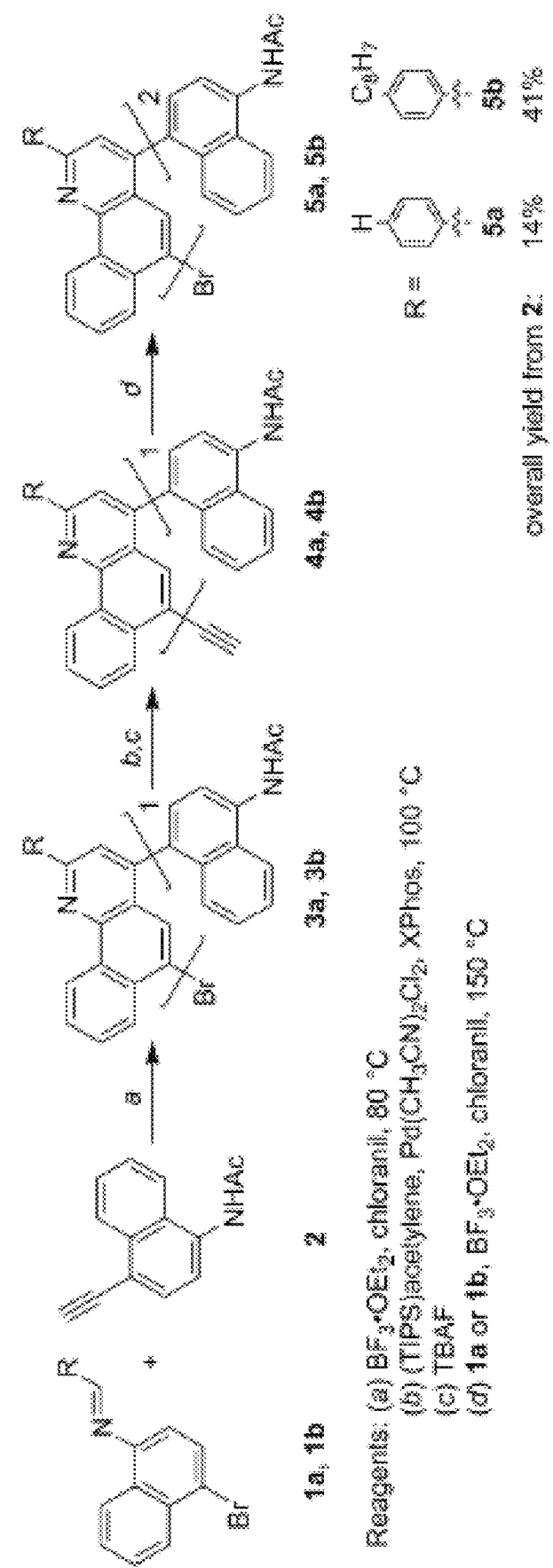
FIGS. 8A and 8B provide synthesis schemes for model benzoquinoline compounds in accordance with embodiments of the invention.

Some embodiments directed to benzoquinoline compounds and their method of manufacture are shown in the diagram provided in FIG. 8A. As described in previous embodiments benzoquinoline compounds (such as those shown by example at FIG. 8A, 3a and 3b) are formed by the reaction of an aldimine having at least two aromatic groups (e.g. napthalene) (FIG. 8A, 1a and 1b) with an alkyne having one or more aromatic groups (e.g., naphthylalkyne) (FIG. 8A, 2) in the presence of a suitable Lewis acid mediator ($BF_3.O$ $Et_2$) and a sacrificial oxidant (e.g., chloranil). It will be understood that the synthesis scheme shown in FIG. 8A is merely exemplary and may be generalized by altering the nature of the reagents and their substituents Although the production of single benzoquinolines have been described, as shown in FIG. 8A (compounds 5a and 5b) and FIG. 8B (compound 8), in other embodiments oligobenzoquinolines and methods of their manufacture are also provided. In such embodiments the pendant bromides of the benzoquinolines (e.g., compounds 3a and 3b in FIG. 8A) are converted to alkynes, forming an alkyne functionalize benzoquinoline (e.g., compounds 4a and 4b of FIG. 8A). The alkyne functionalized benzoquinoline is then reacted with the aldimine (e.g., compound 1a or 1b in FIG. 8A) again using a Lewis acid mediator and sacrificial oxidant to produce oligobenzoquinolines (compounds 5a and 5b.)

Figure 8B:
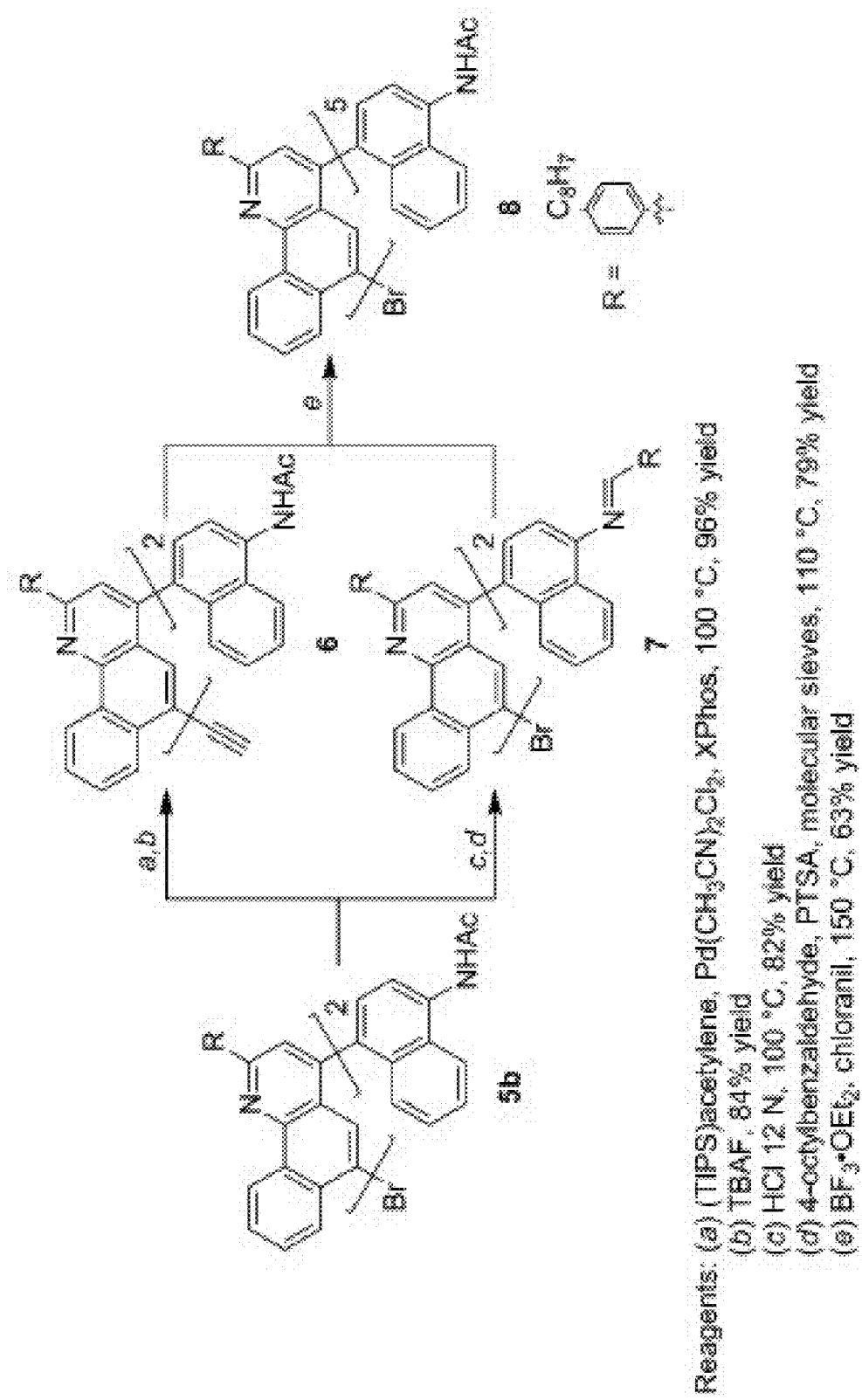

This linear synthetic strategy in accordance with embodiments is capable of producing regioisomerically pure products, and may be utilized to produce compounds having an arbitrary number of benzoquinolines interconnected. For example, FIG. 8B provides a diagram of a process for producing pentameric benzoquinolines (FIG. 8B, compound 8a) in accordance with embodiments of the method. It will be understood that the synthesis scheme shown in FIG. 8B is merely exemplary and may be generalized by altering the nature of the reagents and their substituents. As shown, in this embodiments the dimeric benzoquinoline (FIG. 8B, compound 5b) is used as the starting material to generate complementary benzoquinoline reagents having alkyne (FIG. 8B, compound 6) and imine (FIG. 8B, compound 7) functionalities. Thus in embodiments an alkyne functionalized benzoquinoline reagent is formed by converting the pendant bromide of the benzoquinoline (FIG. 8b, compound 5b) to an alkyne, and an imine functionalized benzoquinoline reagent is formed by converting the acetyl-protected amine of the benzoquinoline (FIG. 8B, compound 5b) to an aldimine using reactions and reagents that will be known to those skilled in the art. These imine and alkyne functionalize benzoquinoline reagents are then combined under the Povarov reaction conditions (e.g., in the presence of a Lewis acid and a sacrificial oxidant) to furnish a pentameric benzoquinoline (FIG. 8B, compound 8). Accordingly, using embodiments, it is not only possible to prepare benzoquinoline macromolecules using a linear synthetic strategy, but also to more facilely create larger benzoquinoline macromolecules by independently modifying the bromide and amine termini of such benzoquinoline precursors.

Figure 9A:
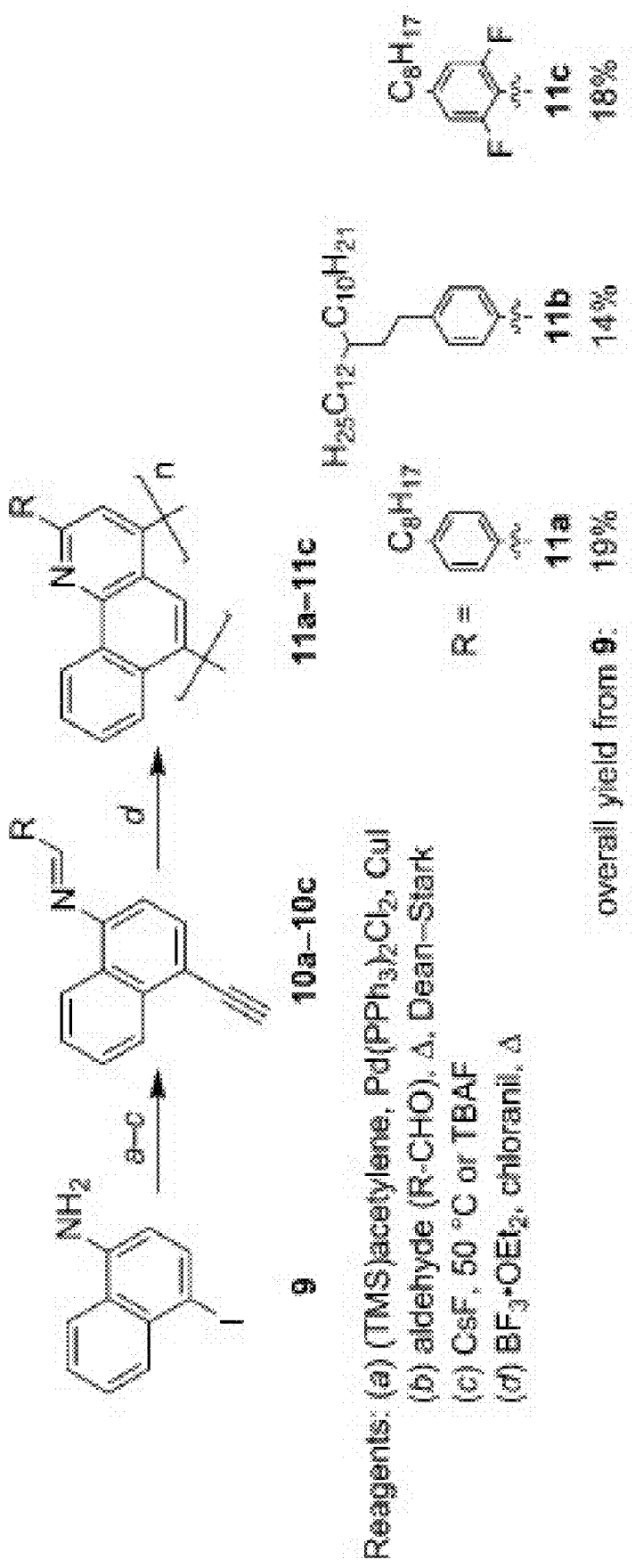
FIGS. 9A and 9B provide synthesis schemes for polybenzoquinoline compounds in accordance with embodiments of the invention.
Figure 9B:
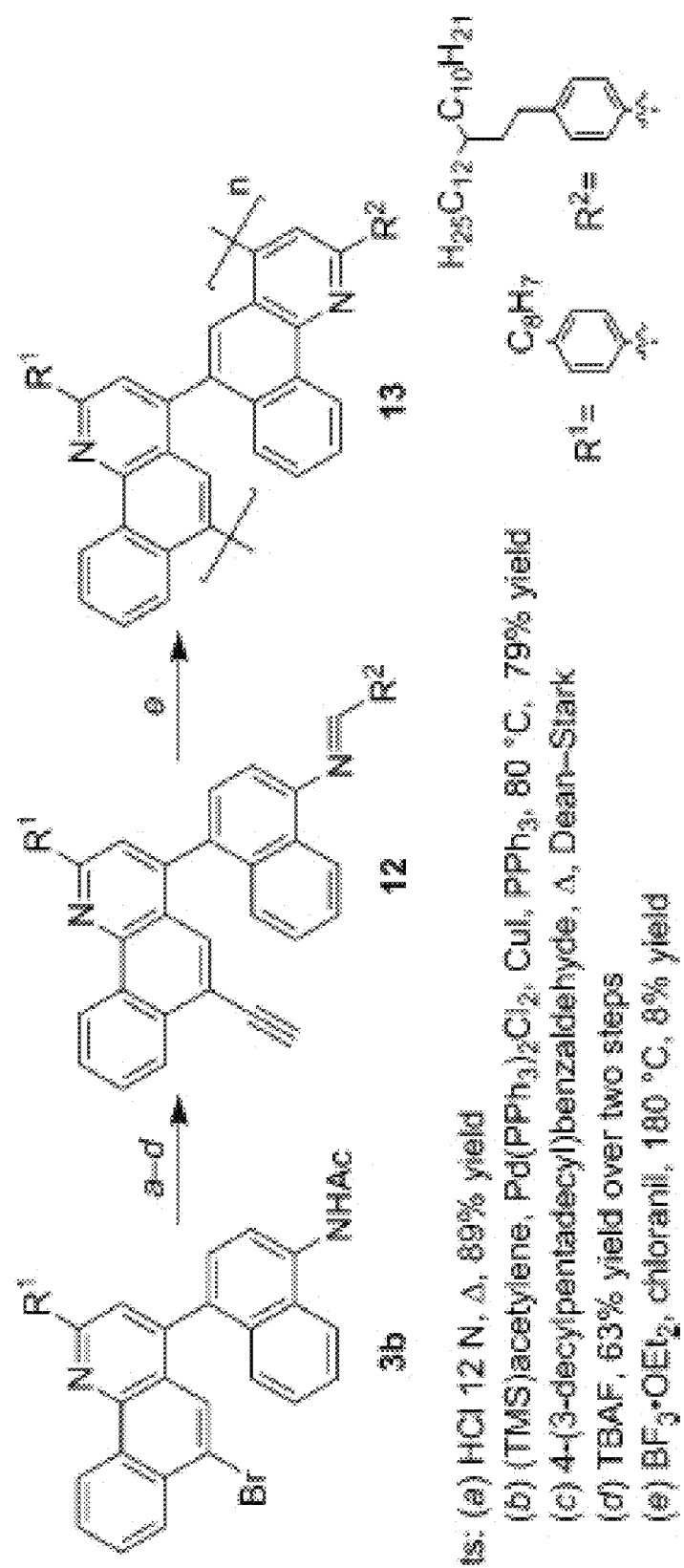

In addition to such benzoquinoline macromolecules, in other embodiments elongated benzoquinoline macromolecules and methods of producing the same are also provided. In many such embodiments, as shown in the schematic provided in FIGS. 9A and 9B, an AB-type aza-Diels-Alder (Povarov) polymerization reaction is implemented using an aromatic bifunctional monomer. It will be understood that the synthesis schemes shown in FIGS. 9A and 9B are merely exemplary and may be generalized by altering the nature of the reagents and their substituents.

In such embodiments, the aromatic bifunctional monomer having both alkyne and aldimine functionalities (e.g., compound 10a in FIG. 9A) is produced in a first-step from a suitable amine functionalized aromatic reagent (e.g., an 4-iodonaphthylamine: compound 9 in FIG. 9A) and a suitable aldehyde reagent. In many preferred embodiments the bifunctional monomer has both the requisite alkyne and aldimine functional groups within a single substrate, as well as an alkyl chain for enhanced solubility. Using the bifunctional monomer thus provided an AB-type aza-Diels-Alder (Povarov) polymerization reaction (as described above) is implemented to polymerize the bifunctional monomer and yield a polybenzoquinoline (FIG. 9A, compound 11a).

Many embodiments of the methods of polymerization allow for a modularity that provides for the accommodation of different peripheral substituents within the benzoquinolines and polybenzoquinolines. In many such embodiments bifunctional monomers are provided that incorporate desired substituent groups, such as, for example, branched alkyl chains (FIG. 9A, compound 11b) and/or fluorine substituents (FIG. 9A, compound 11c). In such embodiments the methods described above in relation to embodiments for producing benzoquinolines and polybenzoquinolines (e.g., FIGS. 8A, 8B and 9A, compounds 3b, 5b, 8 and 11a) may be adapted to furnish substituted polybenzoquinolines (e.g., FIG. 9A, compounds 11 b from 10b and polybenzoquinoline 11c from 10c) by simply altering the functional R-groups attached to the bifunctional monomer. For example, many other substitutions and substituents may be made to the bifunctional monomers in accordance with embodiments by simply altering the R-group of the aldehyde reagent utilized to produce the bifunctional monomer. Some examples of such substitutions may include the introduction of heteroatoms into the aromatic rings and substituent halogens (e.g., F, Cl, etc.), alkyl chains, alkoxys (e.g., OMe), acetyls, N-acetyls, amines, alkyl amines (e.g., $N(Me)_2$), and sulfides (e.g., SMe), among others. Accordingly, embodiments of such methods allow for the preparation of distinct polybenzoquinolines under similar conditions underscoring the potential general scope of embodiments of the approach.

In other embodiments the polymerization strategy for producing polybenzoquinolines outlined above may also be used in the preparation of longer, sequence-variable polybenzoquinoline macromolecules. In such embodiments (an example of which is provided in FIG. 9B) the procedure for the preparation of the bifunctional monomer (e.g., compounds 10a-10c in FIG. 9A) is slightly modified. In such embodiments the bifunctional monomer comprising the requisite alkyne and aldimine functional groups incorporates an expanded aromatic core containing an additional benzoquinoline subunit. In some such embodiments this additional benzoquinoline subunit also comprises optional heteroatoms and an alternating substituent group of interest ($R^2$-group), such as linear and/or branched alkyl sidechains (e.g., FIG. 9B, compound 12, or other desired R-groups as previously discussed (e.g., halogens (e.g., F, Cl, etc.), alkyl chains, alkoxys (e.g., OMe), acetyls, N-acetyls, amines, alkyl amines (e.g., $N(Me)_2$), and sulfides (e.g., SMe), etc.). Once the expanded bifunctional monomer is prepared, polymerization may be undertaken via the aza-Diels-Alder (Povarov) reaction described earlier to yield a polybenzoquinoline having incorporated therein the desired additional functionality (e.g., $R^2$-group in compound 13 of FIG. 9B).

Other embodiments are directed to 2,4,6 substituted benzoquinolines and methods of their production. In such embodiments, a methodology is provided for the installation of varying chemical substituents at the 2 position of 4,6-linked benzoquinolines (corresponding to edge locations in GNRs formed therefrom, as will be discussed in greater detail below). Given the well-known sensitivity of the electronic structure of GNRs to edge modification, embodiments that allow for such edge modification provide the further ability to control the electrical functionality of the envisioned GNR materials.

Figure 10:
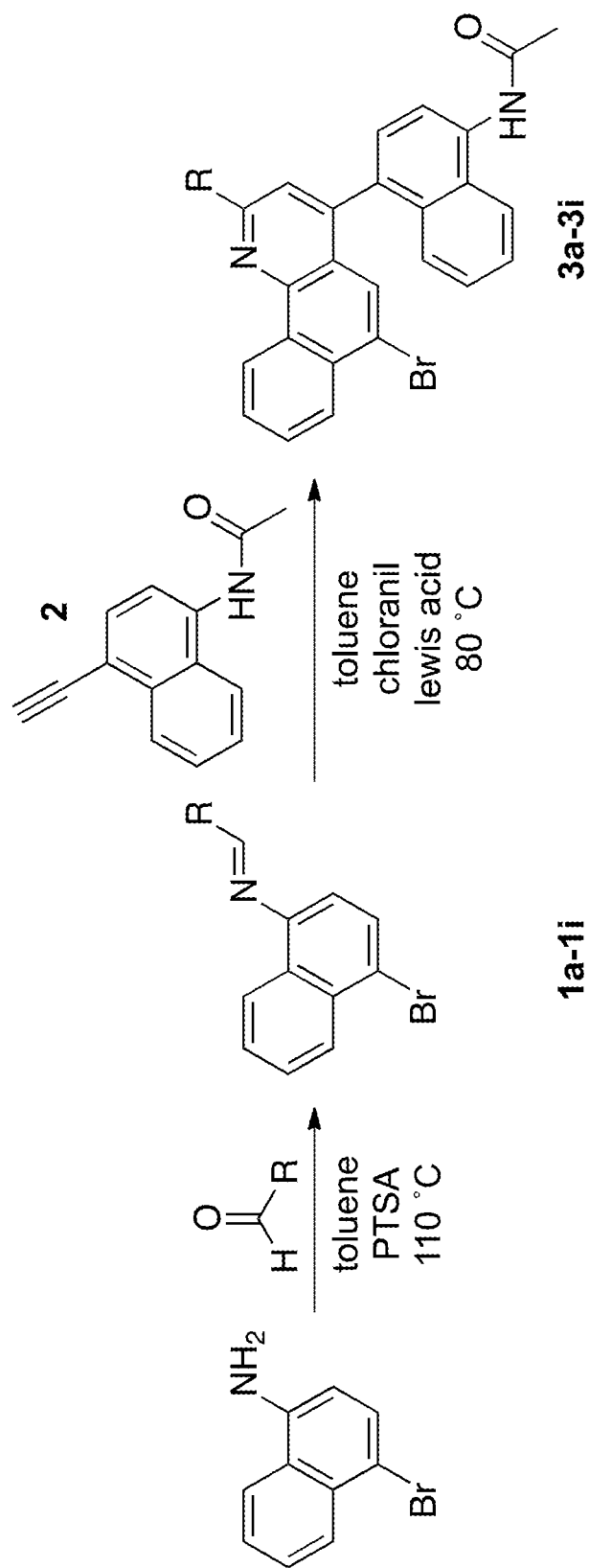
FIG. 10 provides a synthesis scheme for crowded benzoquinoline compounds in accordance with embodiments of the invention.
Figure 11:
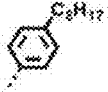
FIG. 11 provides a table of properties of various benzoquinoline compounds in accordance with embodiments of the invention.
Figure 11:
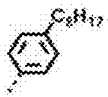
Figure 11:
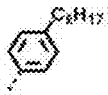
Figure 11:
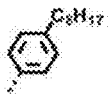
Figure 11:
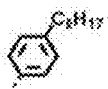
Figure 11:
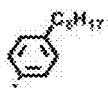
Figure 11:
Figure 11:
Figure 11:
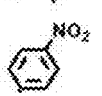
Figure 11:
Figure 11:
Figure 11:
Figure 11:
Figure 11:
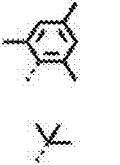
Figure 11:
Figure 12A:
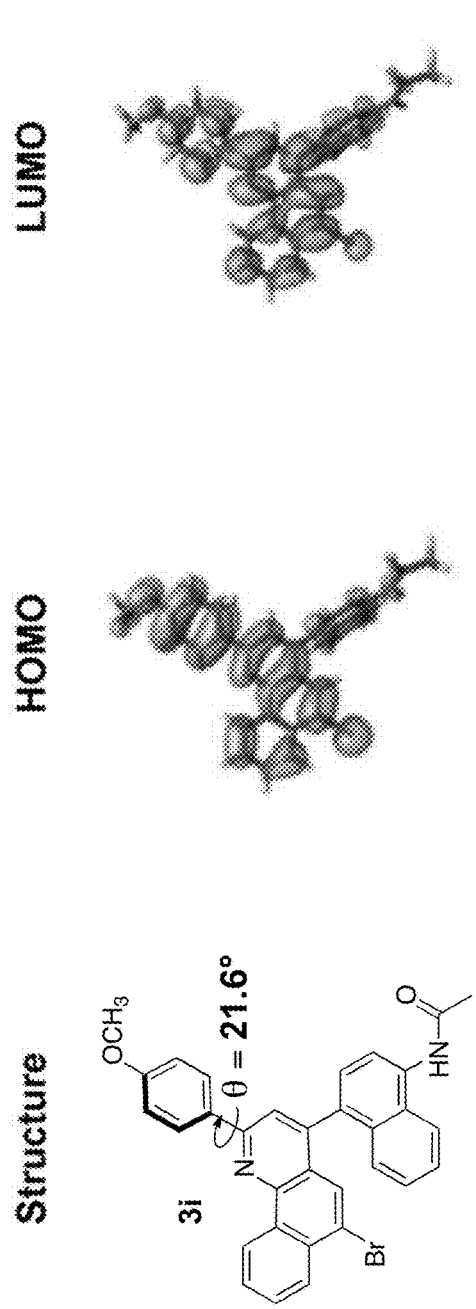
FIGS. 12A to 12E provide the chemical structure and HOMO and LUMO for various benzoquinoline compounds in accordance with embodiments of the invention.
Figure 12B:
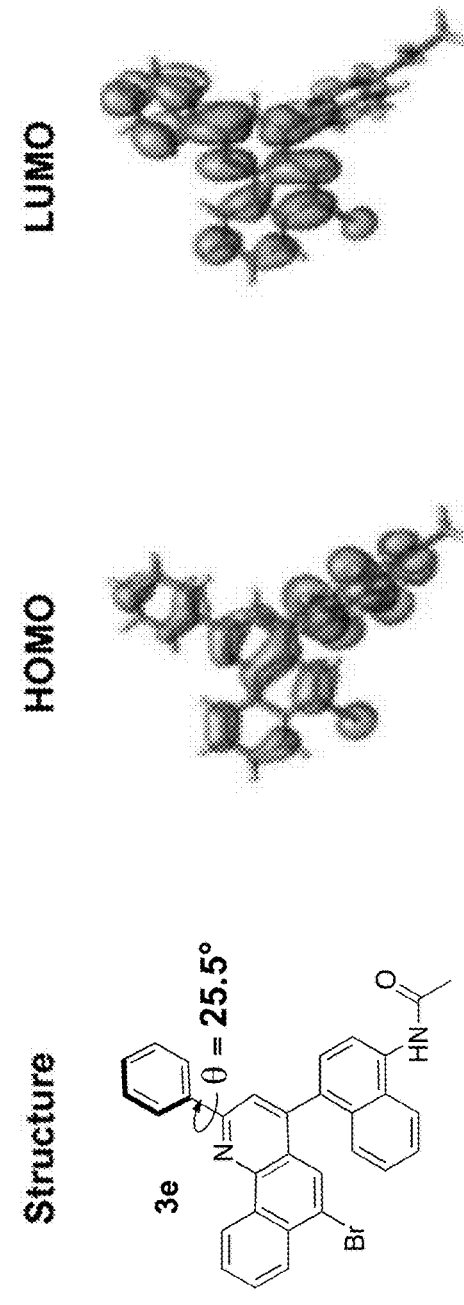
Figure 12C:
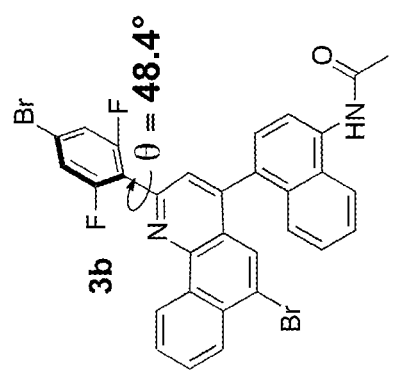
Figure 12C:
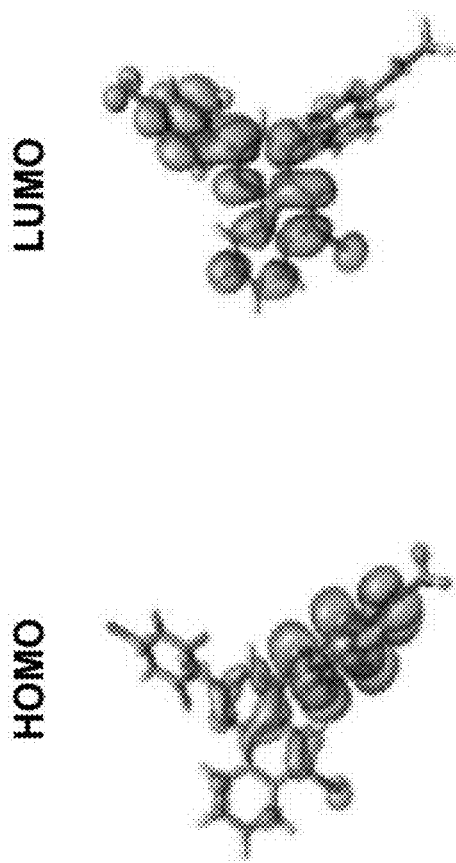
Figure 12D:
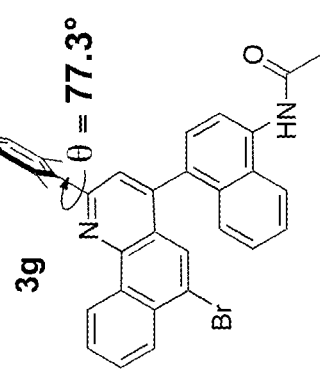
Figure 12D:
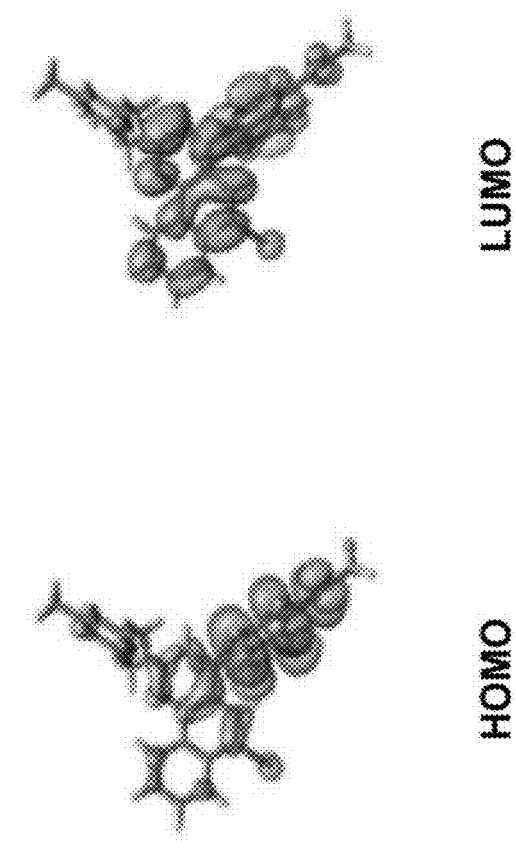
Figure 12E:
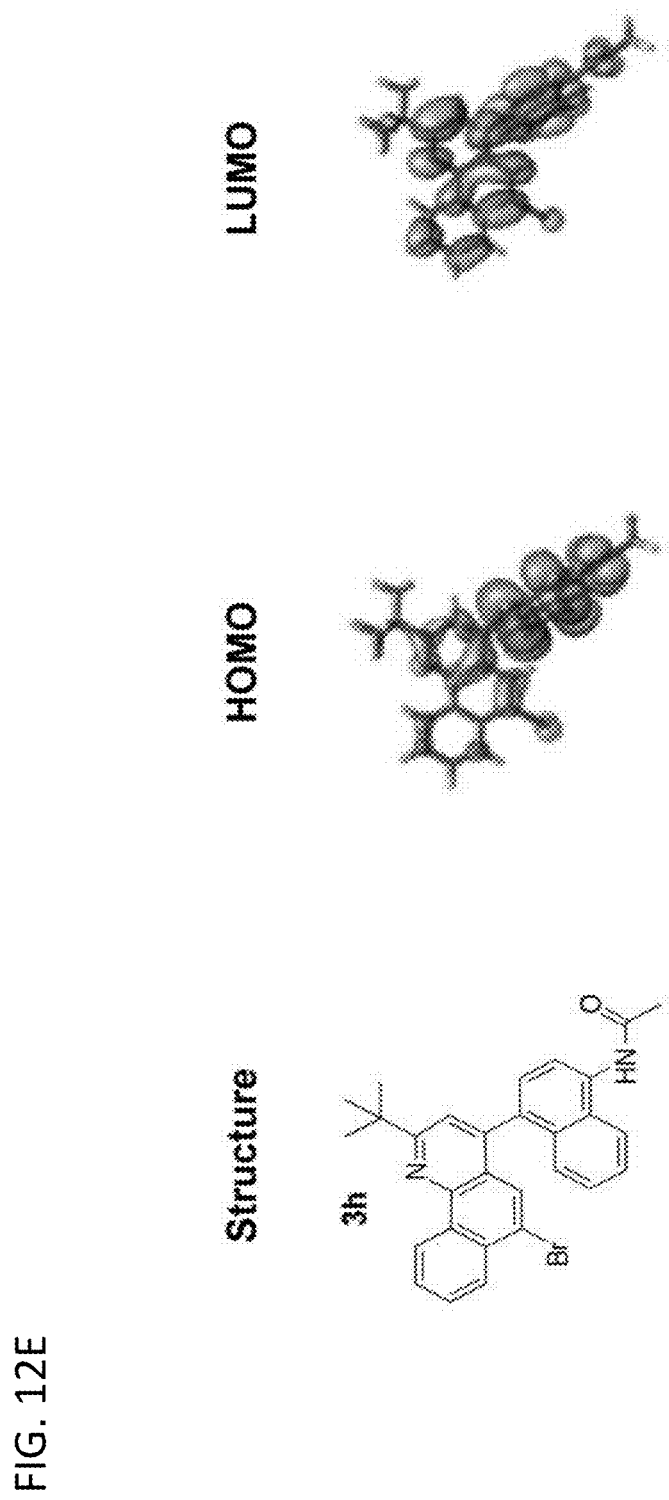

As shown in FIG. 10, in many embodiments an aza-Diels-Alder reaction is provided that allows for the synthesis of 2,4,6-substituted benzoquinoline compounds via a Lewis acid-promoted Povarov reaction as described elsewhere herein. It will be understood that the synthesis schemes shown in FIG. 10 is merely exemplary and may be generalized by altering the nature of the reagents and their substituents. Thus, in accordance with embodiments an aromatic aldimine precursor (compound 1a in FIG. 10) is produced from commercially available starting materials (e.g., 4-bromonaphylamine and octyl benzaldehyde) through known literature protocols. (See, e.g., See, e.g., D. J. Dibble, et al., *Macromolecules,* 2015, 48, 557 and D. J. Dibble, et al., *Angew. Chem. Int. Ed.,* 2015, 54, 5883, cited above.) The aromatic aldimine is then reacted with an aromatic alkyne having a further aldehyde functionality attached thereto (e.g., naphthyl alkyne, compound 2 in FIG. 10) in the presence of a Lewis acid to furnish the crowded benzoquinoline (e.g., compound 3a in FIG. 10). As previously described, a sacrificial oxidant (e.g., chloranil) may also be provided to ensure the benzoquinoline is fully aromatized. As described previously, a number of suitable Lewis acids may be used to promote the cycloaddition of the alkyne to the aldimine. The table provided in FIG. 11 provides the results from several Lewis acids (entries 1 to 4 in Table 1). As shown a number of the Lewis acids resulted in measurable yields. In particular, good yields and regioselectivity were obtained for the following Lewis acids: AgOTf (67%), $ZnCl_2$ (75%), and $BF_3.OEt_2$ (83%) (entries 6-8 in Table 1) showing that a range of possible Lewis acids are usable with embodiments of the methods.

As discussed previously, many different commercially available benzaldehyde derivatives may be utilized to prepare distinct aromatic aldimines (e.g., compounds 1b to 1i in FIG. 11). Embodiments allow for these structurally variant aromatic aldimines to be combined with the aromatic alkyne to furnish a vast array of regioisomerically pure 2,4,6-substituted benzoquinolines (e.g., compounds 3b-3i in FIG. 11). Notably methods according to embodiments allow for the preparation of benzoquinolines featuring both electron withdrawing (e.g., entries 8, 9, 10, and 12 in Table 1 of FIG. 11) and electron donating (e.g., entry 15 in Table 1 of FIG. 11) substituents in good yields of >65%. Moreover, embodiments of the protocol are also capable of accommodating sterically hindered aldimines featuring ortho substituents on their pendant phenyl rings (e.g., entries 8 and 13 in Table 1), with little deleterious effect on the yields. Embodiments of methods also accommodate aliphatic substituents (e.g., entry 14 in Table 1 of FIG. 11). Accordingly, embodiments readily accommodate varying chemical functionalities, including electron donating, electron withdrawing, sterically hindered, and saturated alkyl moieties.

Studies on the electronic properties of these exemplary compounds with ultra-violet-visible (UV-vis) spectroscopy, as described in greater detail in the Exemplary Embodiments, establish that steric effects can be utilized in accordance with embodiments to alter the electronic properties of the benzoquinoline compounds. For example, FIGS. 12A to 12E provide the chemical structures and corresponding HOMO and LUMO isosurface plots for compounds a number of exemplary compounds made in accordance with embodiments (e.g., compounds 3b, 3e, 3g, 3h, and 3i, from FIG. 11). As shown, the orientation of the naphthyl substituent relative to the benzoquinoline core was similar for these molecules, with a typical dihedral angle of ~74°, however, the dihedral angle between the pendant phenyl ring and benzoquinoline core could be roughly correlated with the localization of the HOMO and LUMO (FIGS. 12A to 12E). Overall, this analysis indicates that steric effects play an important role in dictating the electronic properties of the exemplary compounds. Accordingly, although not to be bound by theory, in some embodiments steric interactions between the crowded benzoquinoline core and the 2,6 substituents of the pendant phenyl rings can increase the dihedral angle between the two systems, twisting them out of co-planarity thereby decoupling the phenyl and benzoquinoline aromatic systems and reducing the overall size of the pi-conjugated framework and altering the electronic properties of the compounds. As such, some embodiments are directed to methods of utilizing steric effects to alter the electronic properties of crowded benzoquinolines, and for the use of such engineered compounds as precursors to provide for the rational design and bottom-up preparation of nitrogen-doped GNRs and their electronic properties.

In summary, embodiments have been developed for the preparation of polybenzoquinolines implementing an aza-Diels-Alder (Povarov) reaction capable of synthesizing modular polybenzoquinolines in relatively few steps using inexpensive precursor materials, and straightforward reaction conditions. Utilizing such embodiments it is possible to prepare a variety of benzoquinoline compounds, including crowded yet soluble polymers with variable peripheral substituents and sizes. Indeed, given the large number of commercially available benzaldehyde derivatives, embodiments of methods allow access to a diverse family of novel benzoquinoline-based materials. Moreover, as will be discussed in greater detail below, the polybenzoquinolines constitute a novel class of precursor polymers for N=7 armchair GNRs, which conventionally have been prepared exclusively from polyanthracenes, some of which have a known propensity to oxidation and undesirable photochemistry. (See, e.g., J. C. C. Atherton and S. Jones, *Tetrahedron* 2003, 59, 9039-9057; and A. R. Reddy and M. Bendikov, *Chem. Commun.* 2006, 1179-1181, the disclosures of which are incorporated herein by reference.) Finally, embodiments provide methods of altering the electronic structures of substituted benzoquinolines by controlling steric factors, which embodiments allow for the control of and ability to rationally design the electronic properties of materials such as GNRs from such building blocks. Finally, given the known general utility of the quinoline motif in medicinal, inorganic, and materials chemistry, embodiments provide broad relevance not only for carbon-based electronics but also for a wide range of other chemical disciplines.

Syntheses of Molecular Segments of Fullerenes and Graphene Nanoribbons

Carbon-based materials, such as fullerenes and graphene nanoribbons (GNRs), have often been touted as the successors to inorganic semiconductors in solar cells and nanoscale transistors. Thus, much research effort has focused on the bottom-up preparation of structurally and chemically well-defined variants of these carbon allotropes, as well as their molecular segments, via traditional organic chemistry techniques. In particular, graphene nanoribbons (GNRs), which are narrow strips of graphene that feature a quantum confinement-induced band gap, constitute a promising class of materials for the next generation of semiconductor devices. The electronic properties of GNRs are exquisitely sensitive to their width, heteroatom content, and edge character. Thus, much research effort has been devoted to the preparation of GNRs that are structurally and chemically defined at the atomic level. Although traditional top-down lithographic approaches have exhibited only limited success in this regard, more recent studies have demonstrated the bottom-up preparation of pristine GNRs via the surface-assisted or solution-phase synthesis of nanoribbon precursor polymers, followed by their cyclodehydrogenation. To date, these bottom-up strategies have primarily focused on all-carbon systems, with only a limited number of studies describing the preparation of nitrogen-containing GNR frameworks. Given the immense potential of substitutional nitrogen doping for tailoring the properties of GNRs, this sparse literature precedent is surprising and likely arises from the substantial challenges associated with the incorporation of heteroatoms at arbitrary locations in graphitic materials.

Figure 13A:
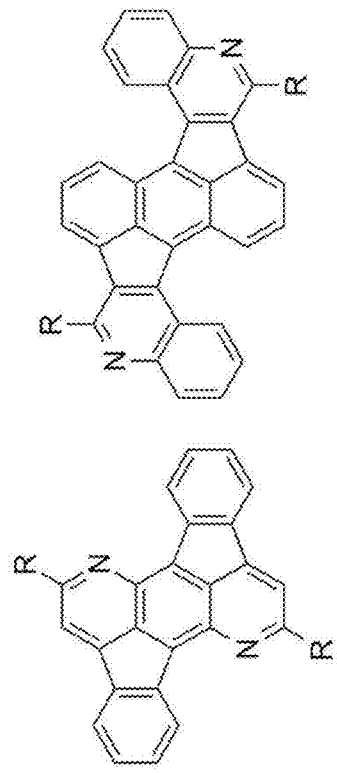
FIGS. 13A and 13B provide illustrations of: A) tetrabenzopentacenes and graphene nanoribbons; and B) rubicenes and fullerenes of both a conventional design and designs in accordance with embodiments of the invention.
Figure 13A:
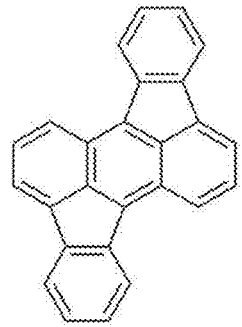
Figure 13A:
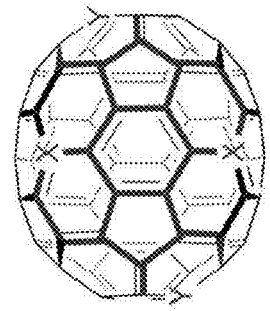
Figure 13A:
Figure 13B:
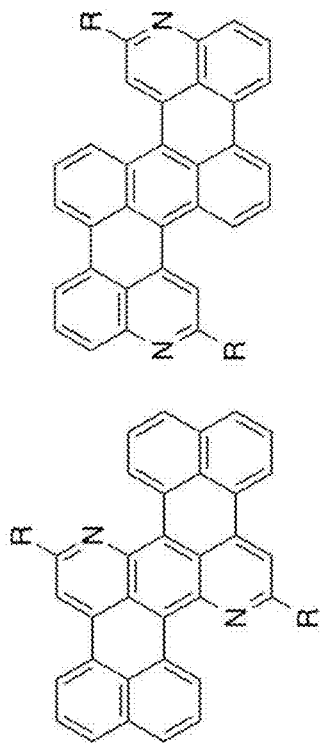
Figure 13B:
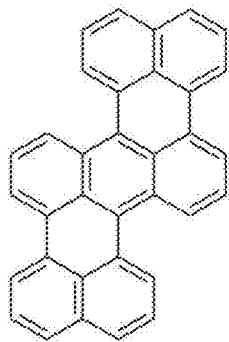
Figure 13B:
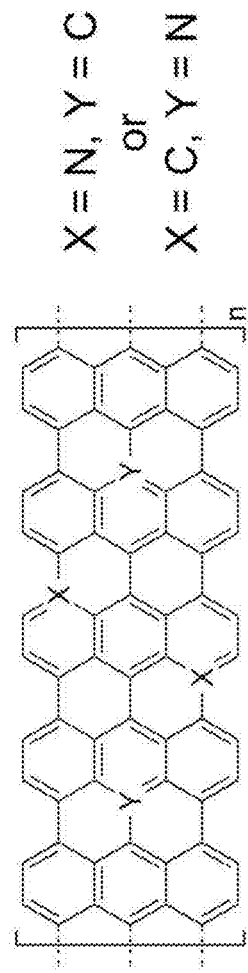

Accordingly, embodiments are directed to molecular segments of fullerenes and graphene nanoribbons, and methods for the rational design and preparation of such materials and their precursors. In many such embodiments, the molecular segments (e.g., rubicene and tetrabenzopentacenederivatives), which constitute molecular segments of C70 fullerenes and the graphene nanoribbons (e.g., N=7 armchair graphene nanoribbons) are nitrogen-doped as illustrated in FIGS. 13A and 13B. Some such embodiments implement the formation of molecular segments and graphene nanoribbons using a combination of an aza-Diels-Alder reaction to form quinoline precursors followed by the cyclodehydrogenation of the quinoline precursor to the molecular segments and/or graphene nanoribbons, as will be described in greater detail below.

Various embodiments of methods of forming such molecular segments and graphene nanoribbons encompass bifunctional quinoline and/or monomers, wherein the monomers comprise at least one aromatic ring incorporating at least an imine and an alkyne substituent. In many such embodiments the aromatic ring is a fused aromatic ring and the imine and aldehyde substituents are collocated on a first of said aromatic rings at the 1 and 4 positions. In other embodiments the second aromatic ring may comprise all carbons or may comprise one or more heteroatoms, including, for example, nitrogen. The monomers may also comprise more than two aromatic rings. The monomers may be polymerized using an aza-Diels-Alder reaction, as described herein, to create a variety of graphene nanoribbon precursors and molecular segments of fullerenes. Many embodiments are thus directed to such quinoline monomers as well as precursors based on such structures and molecular segments and graphene nanoribbons formed therefrom.

Synthesis of Molecular Segments

In some aspects, embodiments provide doped molecular segments and methods of the rational design and preparation of such molecular segments. Some embodiments of such molecular segments include, for example, nitrogen-doped molecular segments, including, rubicene and tetrabenzopentacene derivatives, which constitute molecular segments of C70 fullerenes and N=7 armchair graphene nanoribbons, respectively. Embodiments of these molecular segments are illustrated in FIGS. 13A and 13B. Embodiments of methods for forming molecular segments provide facile access to previously unknown polycyclic aromatic hydrocarbons (PAHs), which hold promise both as organic electronic functional materials and as model compounds for the ultimate construction of larger carbonaceous systems, such as, for example, graphene nanoribbons. It will be understood that embodiments of such molecular segments and graphene nanoribbons are formed as alternatives to classic all-carbon rubicene (FIG. 13A, left) and tetrabenzopentacene (FIG. 13B, left) motifs. In such embodiments, these molecules incorporate nitrogen heteroatoms within their aromatic systems (FIG. 13A, right and FIG. 13B, right). Such PAHs constitute molecular segments of nitrogen-doped C70 fullerenes (FIG. 13A, bottom) and N=7 armchair graphene nanoribbons (FIG. 13B, bottom), which have been difficult historically to access synthetically.

In many such embodiments the methods involve a two-step process wherein a first step comprises the synthesize of bifunctional halogenated building blocks followed by the conversion of these building block to form highly derivatized anthracene precursors via the aza-Diels-Alder (Povarov) reaction previously described. (See, e.g., D. J. Dibble, et al., *Macromolecules* 2015, 48, 557-561, the disclosure of which is incorporated herein by reference.) Embodiments of such two-steps processes further incorporate a second step wherein the precursors formed in the first Povarov conversion step are used to form two 5-membered fused rings via a Heck reaction (see, e.g., X. Chen, et al., *Angew. Chem. Int. Ed.* 2009, 48, 5094-5115; *Angew. Chem.* 2009, 121, 5196-5217; D. McCartney, P. J. Guiry, *Chem. Soc. Rev.* 2011, 40, 5122-5150; and R. F. Heck, *Org. React.* 1982, 27, 345-390, the disclosures of which are incorporated herein by reference), or to form two 6-membered fused rings via a base-mediated cyclodehydrogenation reaction (see, e.g., A. Studer, D. P. Curran, *Nat. Chem.* 2014, 6, 765-773; O. R. Luca, et al., *Org. Chem. Front* 2015, 2, 823-848; and M. Kivala, et al., *Cyclodehydrogenation in the Synthesis of Graphene-Type Molecules In Materials Science and Technology*, 2013, pp. 373-420, the disclosures of which are incorporated herein by reference) within the obtained anthracene skeletal frameworks, furnishing nitrogen-containing molecular segments, such as, for example, rubicene or tetrabenzopentacene derivatives, respectively.

Figure 14A:
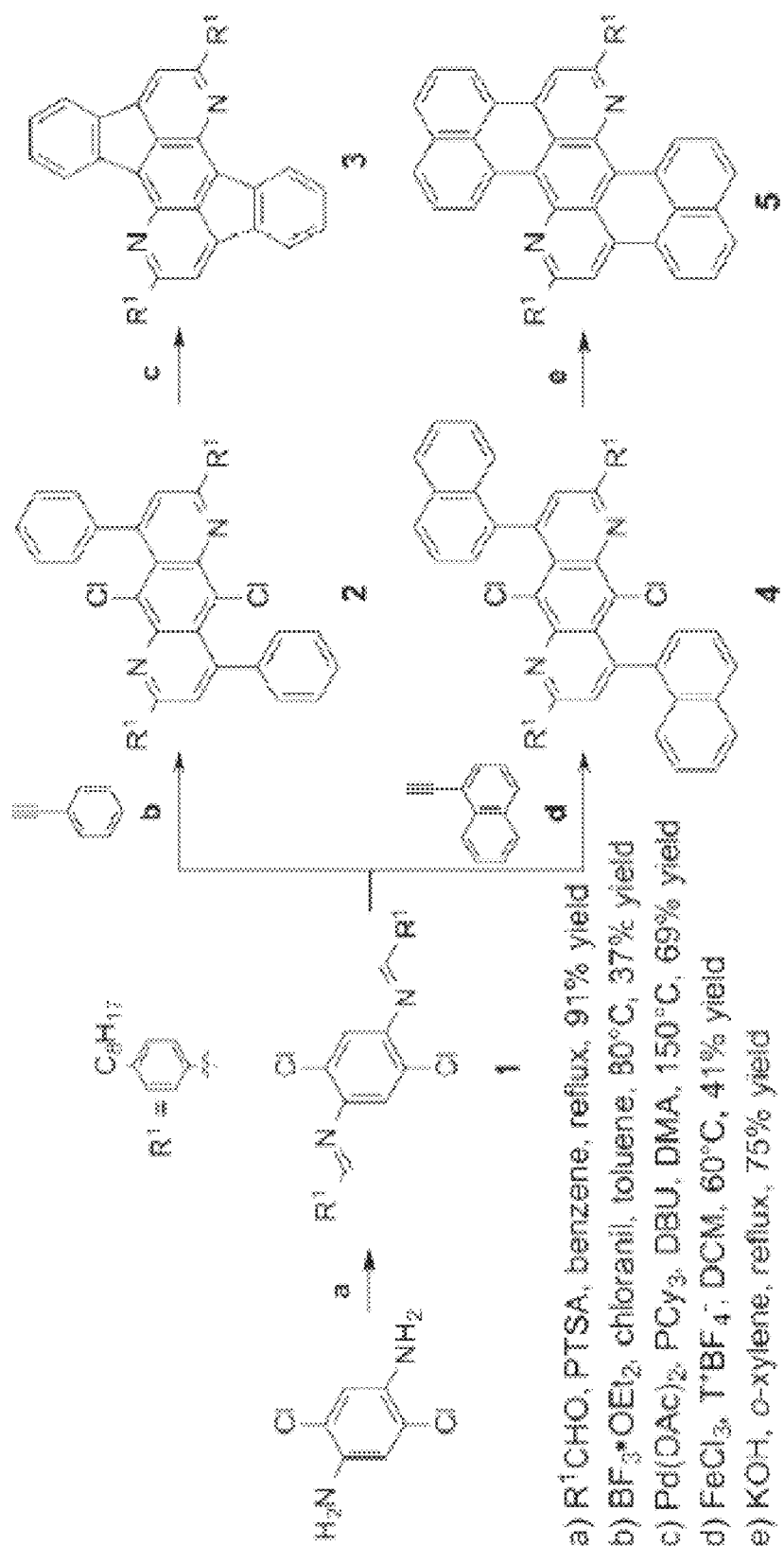
FIGS. 14A and 14B provide synthesis schemes for rubicenes and tetrabenzopentacenes in accordance with embodiments of the invention.
Figure 14B:
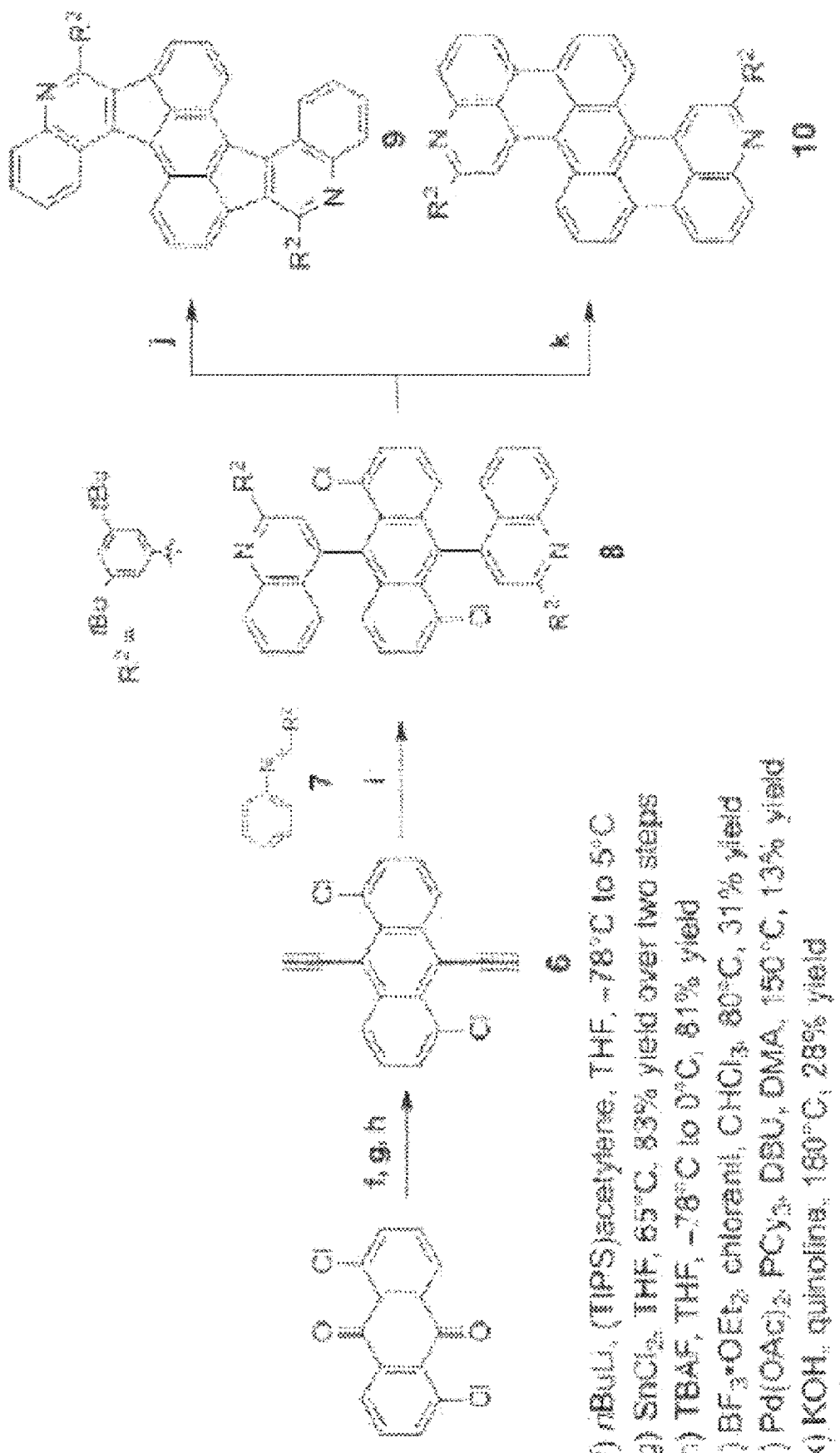

Exemplary embodiments of such synthetic schemes are provided in FIGS. 14A and 14B. It will be understood that the synthesis schemes shown in FIGS. 14A and 14B are merely exemplary and may be generalized by altering the nature of the reagents and their substituents. As shown in FIG. 14A, molecular segments (e.g., rubicene 3 and tetrabenzopentacene 5 in FIG. 14A) are formed via a Povarov reaction as previously described. More specifically, in embodiments the molecular segments (FIG. 14A) are formed by first preparing a bis(aldimine) 1 through known literature procedures as previously described. Subsequently, anthracene precursor compound 2 is obtained by reacting the aldimine with an alkyne functionalize single ring aromatic compound (e.g., phenylacetylene) in the presence of a Lewis acid mediator (e.g., $BF_3 \cdot OEt_2$) and an oxidant (e.g., chloranil) under suitable reaction times and temperatures (as previously described), while anthracene precursor compound 4 is obtained by reacting bis(aldimine) 1 with an alkyne functionalized double ring aromatic compound (e.g., 1-ethynylnaphthalene) in the presence of a Lewis acid (e.g., $FeCl_3$) and an oxidant (e.g., a TEMPO oxonium salt), again under suitable reaction conditions.

Once the highly derivatized anthracene precursors, having at least halogen, aromatic groups and desired R-group substituents functionalized along the central anthracene ring are formed, the precursors are then transformed into the desired molecular segment. For example, in some such embodiments the anthrocene precursor may be transformed via a palladium-catalyzed Heck reaction to form intramolecular C—C bonds between the acene core and pendant phenyls of the anthracene precursor to form a rubicene material 3. In analogous embodiments, tetrabenzopentacene (e.g., compound 5 in FIG. 14A) may be obtained using base-mediated cyclodehydrogenation to form intramolecular C—C bonds between the acene core and pendant naphthyls of precursor compound 4.

Although the above embodiments describe methods of forming different molecular segments via separate anthracene precursors, in other embodiments a single multifunctional anthracene precursor may be utilized capable of producing different molecular segments. One exemplary embodiment of such a method is provided in FIG. 14B. As shown, in this embodiment rubicene (compound 9 in FIG. 14B) and tetrabenzopentacene (compound 10 in FIG. 14B) are produced via a common anthracene precursor having at least halogen and quinoline substituents having desired R-groups attached thereto along the central anthracene ring. In such embodiments a Povarov reaction, is utilized to form the anthracene precursor as illustrated in FIG. 14B. As shown, to obtain the molecular segments, a halogenated bis(alkyne) anthrocene 6 is first prepared according to known techniques. Then an aldimine 7 is formed and reacted with the bis(alyne), again in the presence of a Lewis acid mediator and an oxidant, producing the anthracene precursor 8. A rubicene (compound 9 in FIG. 14B) is then prepared in accordance with embodiment using a palladium-catalyzed Heck reaction to form intramolecular C—C bonds between the acene core and pendant quinolines of the anthracene precursor. In alternative embodiments a tetrabenzopentacene (compound 10 in FIG. 14B) is produced using base-mediated cyclodehydrogenation to form intramolecular C—C bonds between the acene core and pendant quinolines of the anthracene precursor.

In summary, embodiments of methods provide a novel Povarov reaction-based methodology for the preparation of nitrogen-doped rubicenes and tetrabenzopentacenes, which are molecular segments of C70 fullerenes and N=7 armchair graphene nanoribbons, respectively. These embodiments represent the first examples of nitrogen-doped rubicenes and tetrabenzopentacenes. In addition, the method according to embodiments utilizes the formation of intramolecular carbon-carbon bonds between arene moieties, facilitating the selective installation of 5- and 6-membered rings in nitrogen-containing PAHs. In contrast, the alternative oxidative cyclodehydrogenation strategies for bond formation in arenes are well-known to be extremely difficult (or impossible) to control for electron-deficient nitrogen-containing heterocycles. (See, e.g., M. Grzybowski, K. Skonieczny, H. Butenschön, D. T. Gryko, *Angew. Chem. Int. Ed.* 2013, 52, 9900-9930; *Angew. Chem.* 2013, 125, 10084-10115, the disclosure of which is incorporated herein by reference.) Embodiments also provide two distinct yet complementary synthetic pathways, which allow for synthetic flexibility and access to molecules that feature nitrogen heteroatoms at different locations and/or possess modular peripheral alkyl substituents, further allowing for the rational, multifaceted tuning of the materials' self-assembly and electronic properties.

Embodiments are also directed to the novel nitrogen-doped molecular segments. It is known that organic electronic materials that exhibit n-type and ambipolar behavior remain quite rare, and the incorporation of nitrogen heteroatoms has been extensively validated as a design strategy for coaxing such behavior from acenes. (See, e.g., J. E. Anthony, *Chem. Rev.* 2006, 106, 5028-5048; J. E. Anthony, *Angew. Chem. Int. Ed.* 2008, 47, 452-483; Angew. Chem. 2008, 120, 460-492; U. H. F. Bunz, *Acc. Chem. Res.* 2015, 48, 1676-1686; *Polycyclic Arenes and Heteroarenes: Synthesis, Properties, and Applications* (Ed.: Q. Miao), Wiley-VCH, Weinheim, 2015. J. E. Anthony, A. Facchetti, M. Heeney, S. R. Marder, X. Zhan, Adv. Mater. 2010, 22, 3876-3892; Y. Zhao, Y. Guo, Y. Liu, *Adv. Mater.* 2013, 25, 5372-5391; and X. Gao, Y. Hu, *J. Mater. Chem. C* 2014, 2, 3099-3117, the disclosures of which are incorporated herein by reference.) Consequently, embodiments of such nitrogen-doped analogues are promising for use in bulk organic semiconductors. Finally, embodiments of the modular constructs allow for the construction of a variety of atomically-defined nitrogen-doped molecular segments of fullerenes and graphene nanoribbons. Accordingly, many embodiments are directed to extended carbonaceous frameworks formed using such molecular segment.

Synthesis of Graphene Nanoribbon Precursors and Graphene Nanoribbons

As previously discussed, many embodiments describe the modular synthesis of polyquinolines and polybenzoquinolines, in other embodiments such compounds are utilized as a generic class of GNR precursor polymers. As discussed in the sections above, embodiments according to the disclosure provide methods of forming such polyquinoline and polybenzoquinoline precursors via a general aza-Diels-Alder reaction. In addition, embodiments of methods also provide AB-type bifunctional monomers and AA/BB-type reagents to synthesize congested but soluble polybenzoquinoline also via a Diels-Alder-type polymerization reaction. Finally, embodiments are also provided that demonstrate the scope and modularity of such methods by preparing polybenzoquinolines and oligobenzoquinolines of various sizes and that feature different peripheral substituents. Overall, these embodiments enable facile and rapid access to a large family of quinoline- and benzoquinoline-based materials, which can then be used as precursors for polymerization reactions to produce graphene nanoribbons, as will be described herein.

Accordingly, in some embodiments various graphene nanoribbons may be produced by polymerizing a quinoline or benzoquinoline-based compound. In some such embodiments quinoline-based compounds may be used as precursors to form polyquinolines and polybenzoquinolines via a Diels-Alder polymerization reaction and then these precursors may in turn be used to form graphene nanoribbons, such as through surface-assisted or solution-based cyclodehydrogenation of the polymeric quinoline-based precursor. (See, e.g., J. Cai, P. et al., *Nature* 2010, 466, 470-473; and X. Yang, et al., *J. Am. Chem. Soc.* 2008, 130, 4216-4217, the disclosures of which are incorporated herein by reference.)

Figure 15:
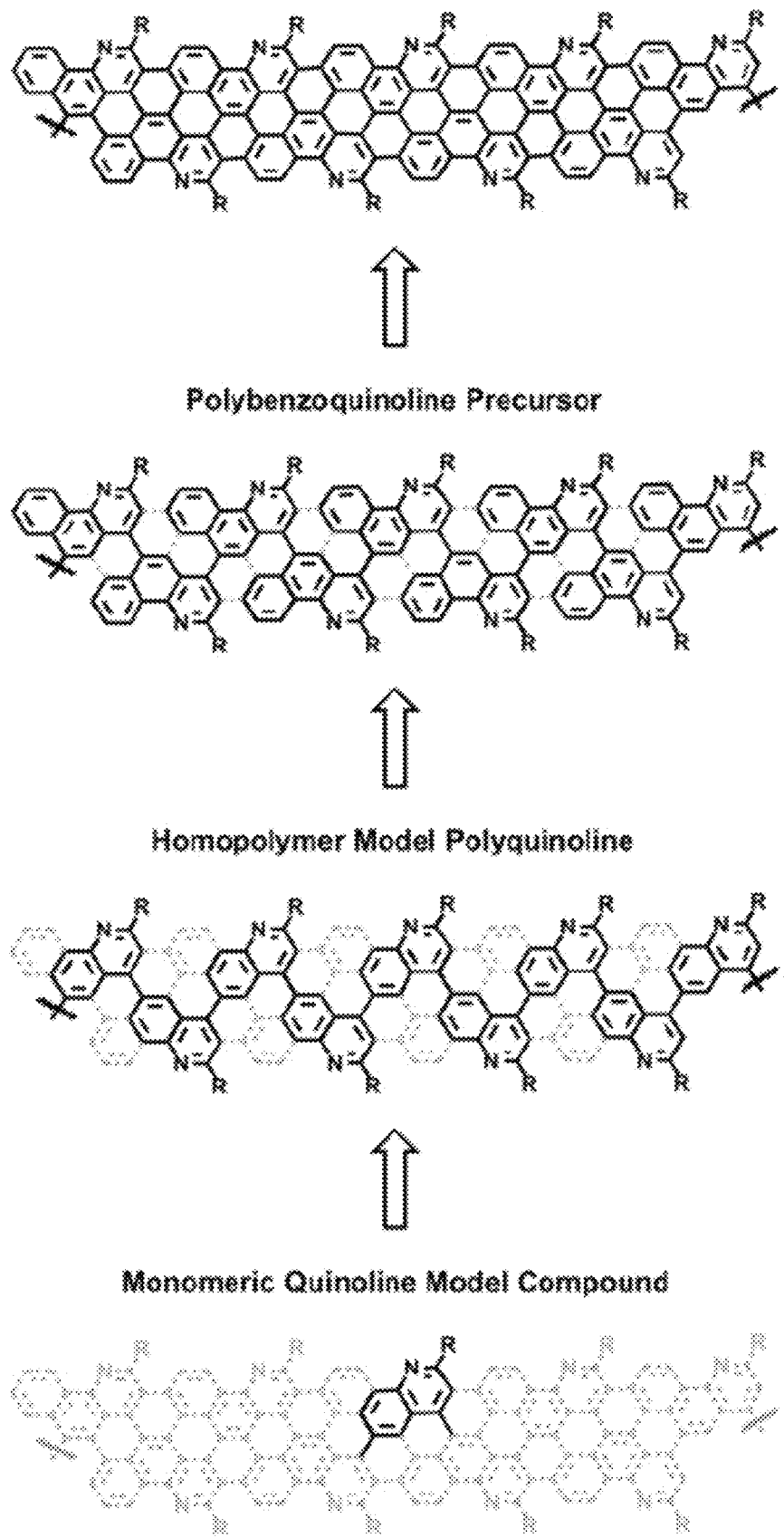
FIG. 15 provides a synthesis scheme for armchair graphene nanoribbons in accordance with embodiments of the invention.

As shown in FIG. 15 by varying the nature of the quinoline-based compounds used in forming the precursors various types of graphene nanoribbons may be formed. For example, in some embodiments a polybenzoquinoline precursor is utilized to form a nitrogen-doped N=7 armchair GNR via cyclodehydrogenation, as shown in FIG. 15. As shown, in such embodiments the formation of a well-defined nitrogen-doped GNR is implemented via a precursor consisting of benzoquinoline subunits linked at their 4 and 6 positions (FIG. 15).

Figure 16A:
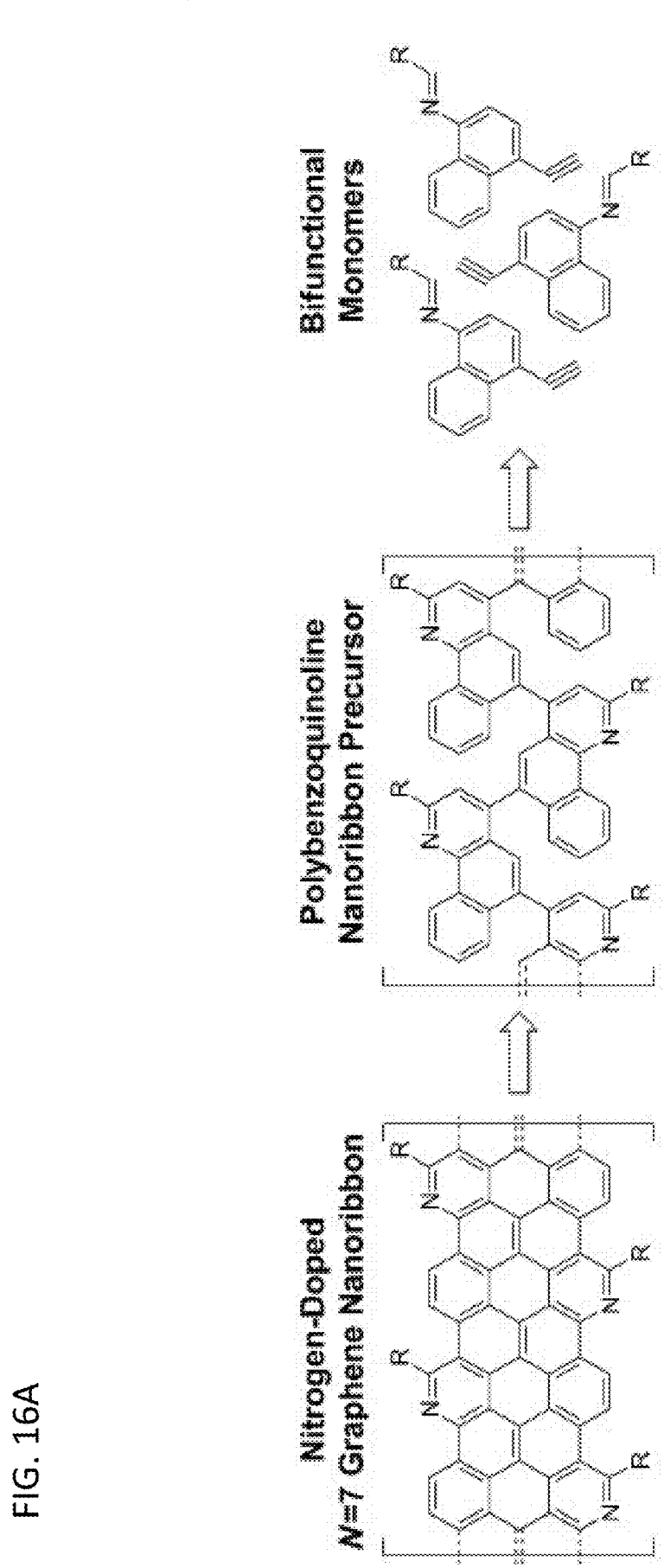
FIGS. 16A and 16B provide synthesis schemes for nitrogen-doped graphene nanoribbons from bifunctional quinoline monomers in accordance with embodiments of the invention.
Figure 16B:
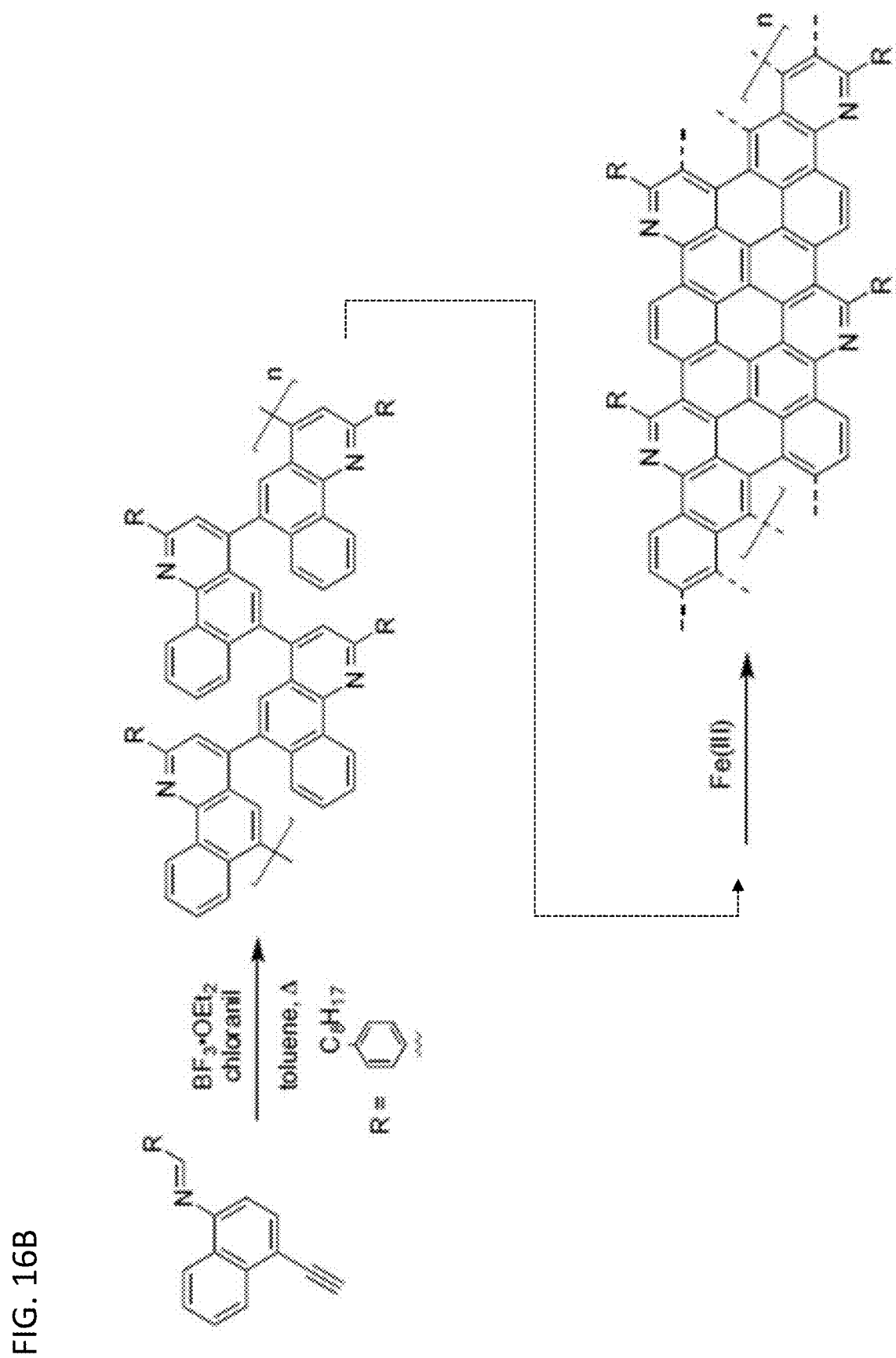

Regardless of the specific GNR to be formed, in embodiments the quinoline-based precursors are produced via a aza-Diels-Alder (Povarov) reaction that constructs the quinoline and benzoquinoline precursor subunits from alkyne- and aldimine-modified monomers (FIG. 16A). Consequently, polymerization of the bifunctional monomers according to embodiments furnishes the desired quinoline or polybenzoquinoline precursor (FIG. 16A, middle), which can then be cyclodehydrogenated into a GNR (e.g., nitrogen-doped N=7 armchair GNR) (FIG. 16A, left). An exemplary synthesis scheme for producing polybenzoquinoline precursors from bifunctional monomers and then cyclization of such polybenzoquinoline precursors into GNRs via the Scholl reaction is provided in FIG. 16B. It should be understood that although specific reagents, R-groups, solvents (e.g., toluene) catalysts (Fe(III)), oxidants (chloranil), Lewis acids ($BF_3.OEt_2$) and reaction conditions are listed in the synthesis scheme of FIG. 16B, suitable alternatives may be utilized as is described within this disclosure.

Figure 17:
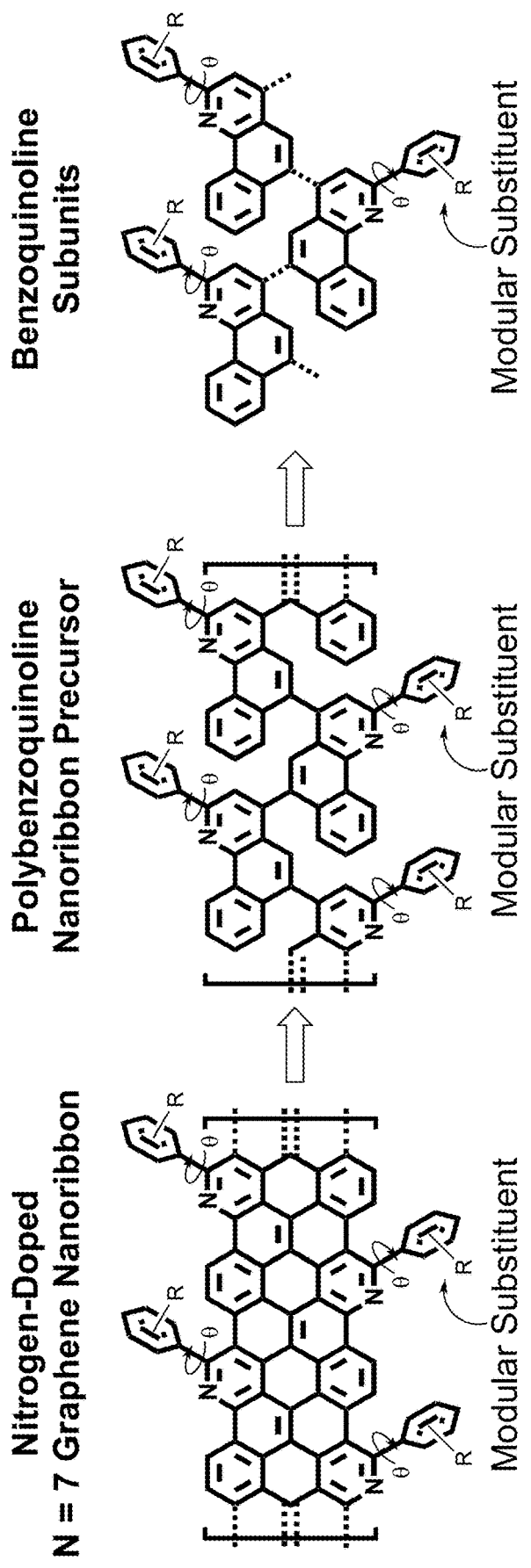
FIG. 17 provides a synthesis scheme for position 2 substituted benzoquinolines and methods of forming graphene nanoribbons therefrom in accordance with embodiments of the invention.
Figure 18A:
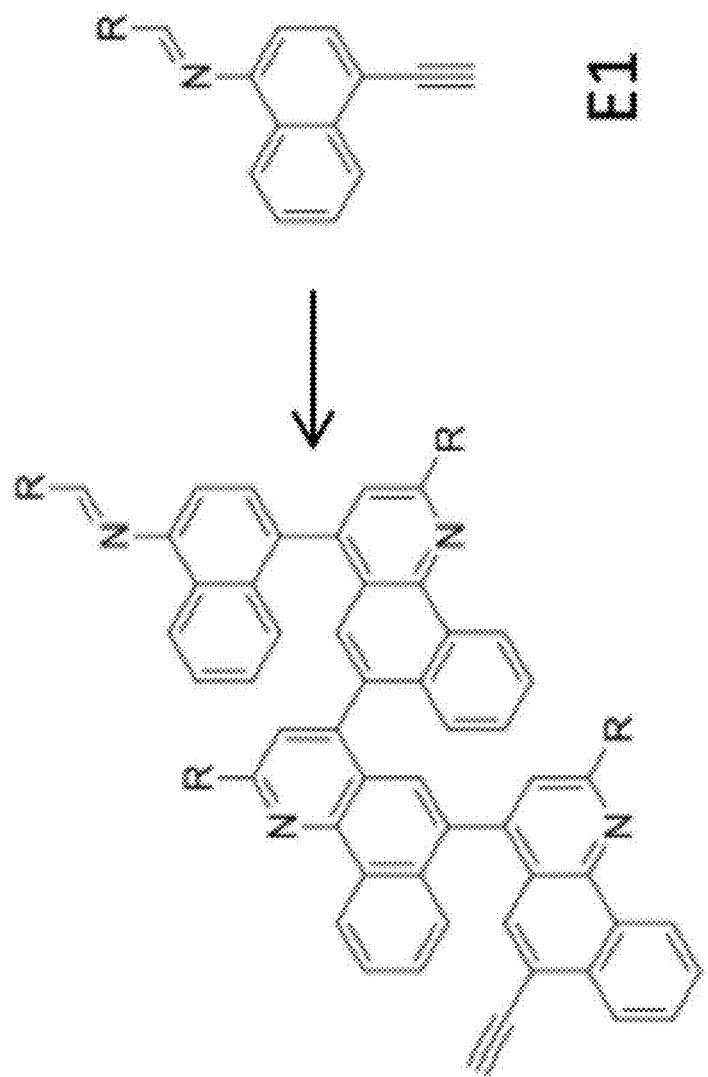
FIGS. 18A to 18D provide bifunctional benzoquinoline monomers and graphene nanoribbon precursors formed therefrom in accordance with embodiments of the invention.
Figure 18B:
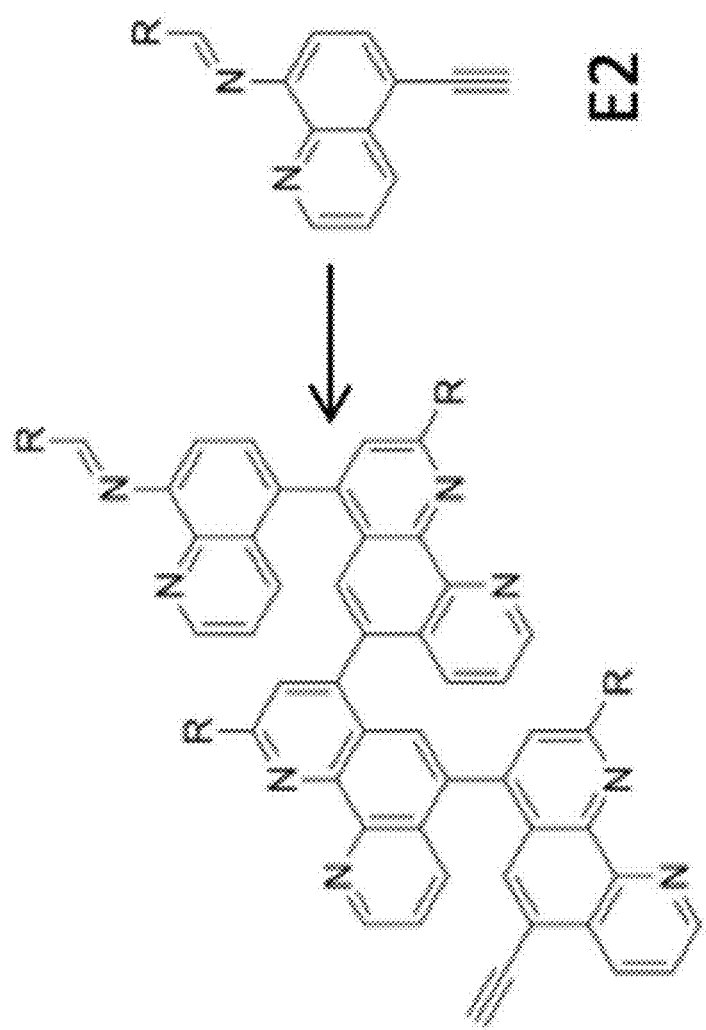
Figure 18C:
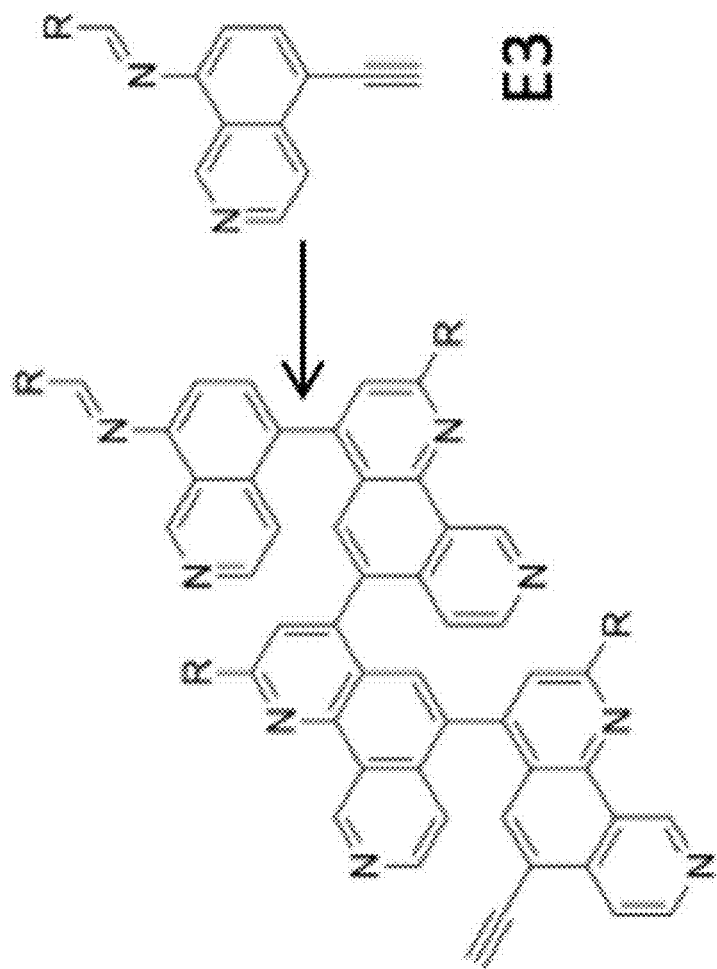
Figure 18D:
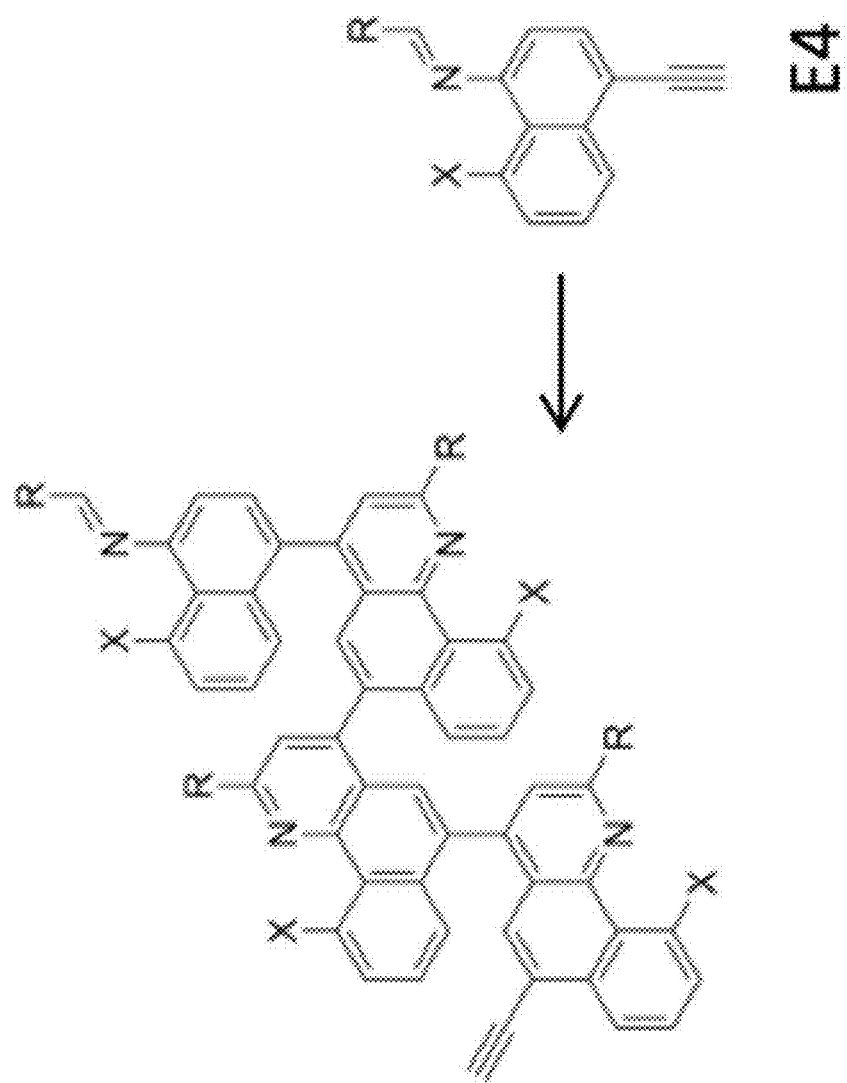
Figure 19A:
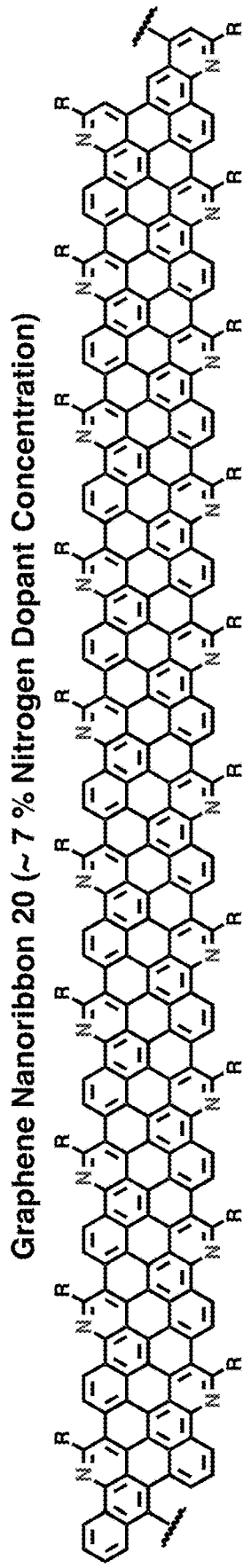
FIGS. 19A to 19E provide illustrations of nitrogen-doped graphene nanoribbons in accordance with embodiments of the invention.
Figure 19B:
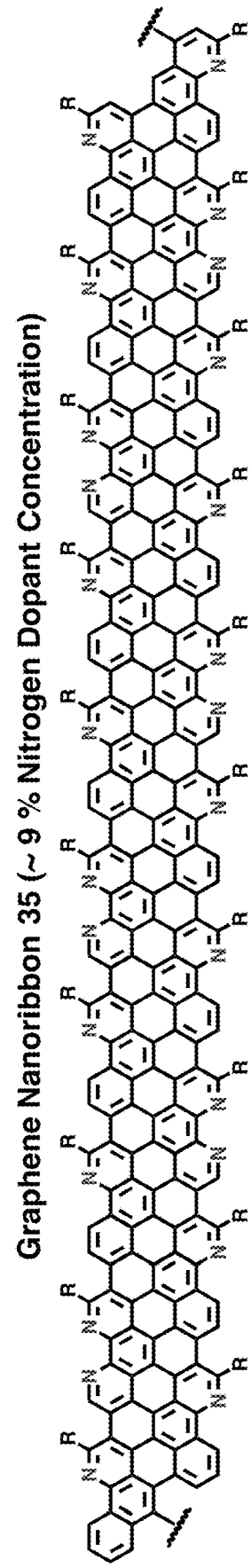
Figure 19C:
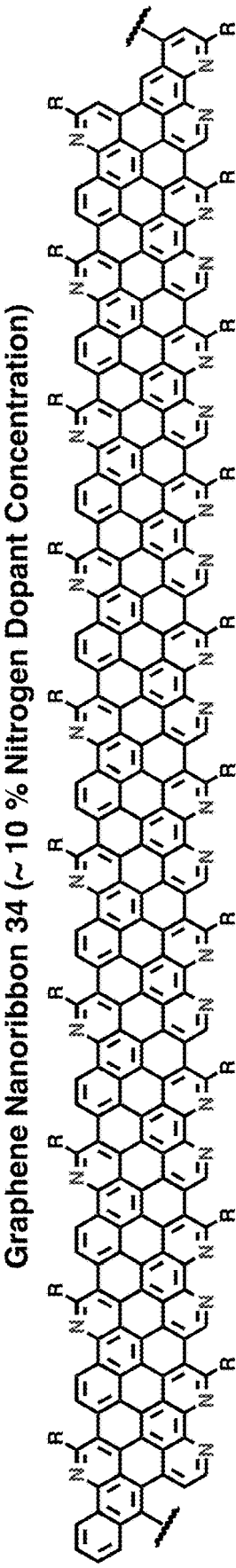
Figure 19D:
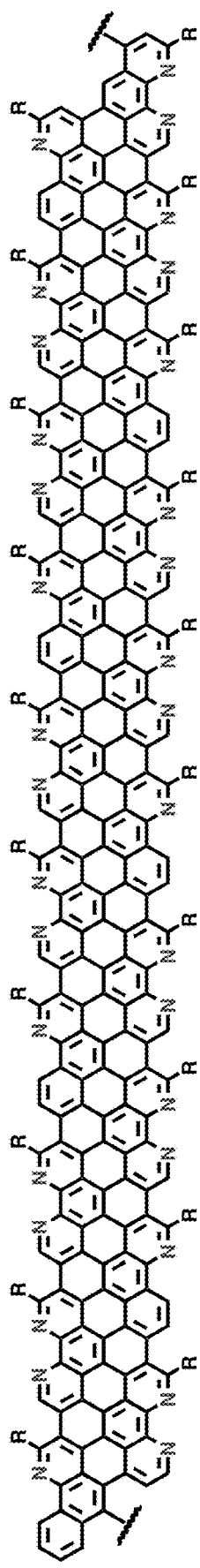
Figure 19E:
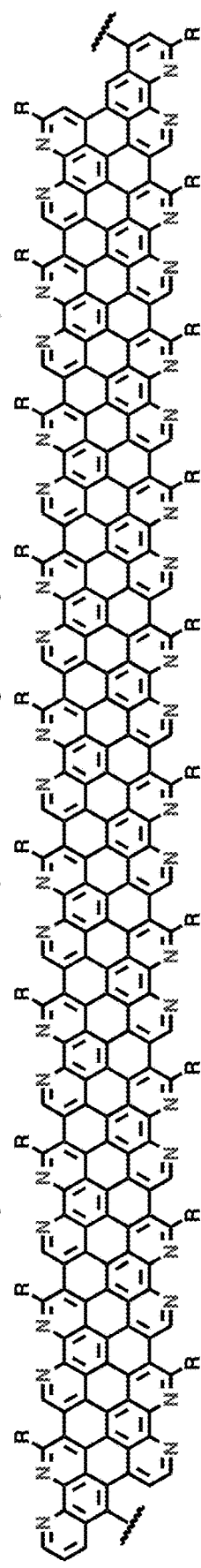

In embodiments previously described the aza-Diels-Alder (Povarov) reaction is utilized to synthesize the envisioned polybenzoquinoline precursor polymers. In alternative embodiments the methodology is used to modularly install varying chemical substituents at the 2 positions of the 4,6-linked benzoquinolines (as shown schematically in FIG. 17). As shown in the illustration the insertion of a substituent at the 2 position corresponds to edge locations in the proposed final GNRs (FIG. 17, left). Given the well-known sensitivity of the electronic structure of GNRs to edge modification, (see, e.g., Castro Neto, et al. *Rev. Mod. Phys.* 2009, 81, 109-162; Chen, L., et al. *Angew. Chem. Int. Ed.* 2012, 51, 7640-7654; Narita, A. et al. *Chem. Rec.* 2015, 15, 295-309; and Narita, A. et al. *Chem. Soc. Rev.* 2015, 44, 6616-6643, the disclosures of which are incorporated herein by reference) embodiments according to such a methodology allows for the potential control of the electrical functionality of such GNR materials.

As previously described, many different functionalities can be substituted into the monomers in accordance with embodiments. In turn, these functionalities can thereby be inserted the graphene nanoribbon precursors and ultimately the GNRs formed therefrom. Some exemplary variant monomer functionalities and how they are modularly incorporated into GNR precursors formed therefrom are shown schematically in FIGS. 18A to 18D. As demonstrated, the modular nature of such functionalities allows for a wide-variety of substitution, including, for example, aromatic ring heteroatoms and various substituent alkyl chains, halogens, and various other substituents including: alkoxys (e.g., OMe), acetyls, N-acetyls, amines (e.g., $NH_2$), alkyl amines (e.g., $N(Me)_2$) and sulfides (e.g. SMe), etc.

Utilizing the modular nature of the monomers produced in accordance with embodiment it is then possible in accordance with other embodiments to engineer specific substituents within the GNRs produced therefrom. For example, some embodiments are directed to methods of controlling the amount of nitrogen doping in the GNR. Some exemplary nitrogen-doped GNRs are shown schematically in FIGS. 19A to 19E. In many embodiments variable nitrogen doping of from ~7% to 14% may be provided for N=7 armchair GNRs by altering the nitrogen content of the quinoline-based monomers described herein and from which the GNRs are formed.

The above embodiments therefore provide a framework for the rational, design and modular construction of GNRs from quinoline-based precursor building blocks having exquisite variability and variety.

EXEMPLARY EMBODIMENTS

The following provides information about the methods and materials used to conduct the exemplary studies that produced the data discussed. It will be understood that this data and the accompanying examples are only provided as illustration and are not meant to limit the scope of the systems, methods and apparatus described throughout the disclosure.

Materials and General Experimental Procedures.
Materials

All chemicals were purchased from Acros Organics or Sigma-Aldrich, and all solvents were obtained from Fisher Scientific and used as received unless otherwise noted. The toluene used to prepare the model systems and polymer was dried with 3 Å molecular sieves and stored under argon. All glassware was oven dried at 150° C. overnight. The reactions were performed under dry argon unless otherwise noted.

Compound Purification Procedures

Flash chromatography was performed using a Combi-Flash Rf 200 purification system manufactured by Teledyne Isco. Deactivated silica gel was prepared by flushing the silica gel cartridge with 1/9 triethylamine/hexanes, followed by hexanes to remove excess triethylamine. Preparatory size exclusion chromatography for polyquinolines was performed with chloroform as the mobile phase using a gravity fed column (70 mm×254 mm) containing BioBeads SX-1 resin (200-400 mesh, Bio-Rad Laboratories, Hercules, Calif.). Additional purification-relevant information and protocols are noted below as required.

Reaction Product Characterization Procedures

All intermediates and products were characterized with a combination of nuclear magnetic resonance (NMR) spectroscopy, mass spectrometry, Fourier transform infrared (FTIR) spectroscopy, and/or ultraviolet-visible (UV-Vis) spectroscopy. The 1H NMR spectra were obtained on a Bruker AVANCE400, a Bruker DRX500, or an AVANCE600 instrument. The 13C NMR spectra were obtained on a Bruker DRX500 outfitted with a CryoProbe (Bruker TCI 500 MHz, 5 mm diameter tubes). Chemical shifts were reported in ppm for 1H and 13C NMR. The chemical shifts for the NMR data were referenced as follows: for samples in CDCl3, the 1H NMR were referenced to tetramethylsilane (TMS) at 0.00, and the 13C NMR were referenced to CDCl3 at 77.16; for samples in CD2Cl2, the 1H NMR were referenced to the solvent peak at 5.32, and the 13C NMR were referenced to the solvent peak at 54.00. The data are labeled as follows: chemical shift, multiplicity (s=singlet, d=doublet, t=triplet, q=quartet, quint=quintet, m=multiplet, br s=broad singlet), the coupling constants (in Hertz), and the integration value. The high resolution electrospray mass spectrometry (HRMS ESI) data was obtained at the University of California, Irvine Mass Spectrometry Facility on a Waters LCT Premier electrospray time-of-flight instrument. FTIR spectra were obtained on a Nicolet Nexus 670 FTIR spectrophotometer. The UV-Vis spectra were collected on an Agilent Cary 100 Series spectrophotometer in tetrahydrofuran (THF) at room temperature.

Polymer Characterization and Analysis Procedures

The polyquinolines were analyzed with size exclusion chromatography (SEC). For the crude polymer, the SEC analysis was performed in THF using an Agilent Technologies 1260 Infinity Series separations module equipped with two ResiPore GPC columns connected in series (7.5 mm×300 mm, multiple pore size, 3 μm) from Agilent Technologies (Santa Clara, Calif.). The separations module was connected to an Agilent 1260 infinity dual angle light scattering, refractive index, and viscometer detectors in series. The flow rate was 1.0 mL/min with an injection volume of 50-100 μL and sample concentration of 1.0 mg/mL.

The purified polymer was characterized by size exclusion chromatography via multi-angle light scattering (SEC-MALS). The SEC analysis was performed using an Agilent Technologies 1260 Infinity Series separations module equipped with two GPC columns (7.8 mm×300 mm, 104 Å pore size, 5 μm & 7.8 mm×300 mm, 100 Å pore size, 5 μm) from MZ Analysentechnik (Mainz, Germany). The separations module was connected to a DAWN HELEOS II MALS detector equipped with a 785 nm laser and 20 nm bandpass interference filters to minimize fluorescence effects (Wyatt Technology Corp., Santa Barbara, Calif.). The concentration was measured by the Optilab TrEX differential refractive index detector at 785 nm (Wyatt Technology Corp., Santa Barbara, Calif.). The flow rate was 0.7 mL/min with an injection volume of 100 μL and sample concentration of 3.0 mg/mL. The above system was used to determine the molecular weight (Mw and Mn) and PDI values reported for the purified polymer. The molecular weight data was analyzed with the Astra 6.1.2 software suite by using a dn/dc of 0.27 mL/g. For purified polyquinoline 4, corresponding to FIG. 3, the analysis yielded values of Mn=10.1 kg mol−1, Mw=10.4 kg mol−1, and Mw/Mn=1.04.

Example 1

Quinoline/Polyqunioline Studies

Model quinoline compounds were synthesized via the aza-Diels-Alder (Povarov) reaction, as illustrated in FIG. 3A. Schiff bases 1a and 1b (FIG. 3A) were formed in a single step from commercially available reagents by using known literature protocols. The Schiff bases were reacted with phenylacetylene in the presence of a Lewis acid mediator and the sacrificial oxidant chloranil, which helped avoid endogenous consumption of the imine. A number of Lewis acids known to mediate the Povarov reaction, were screened. Overall, the reaction exclusively produced 2a and 2b (FIG. 3A) as the products in good yields.

Figure 20A:
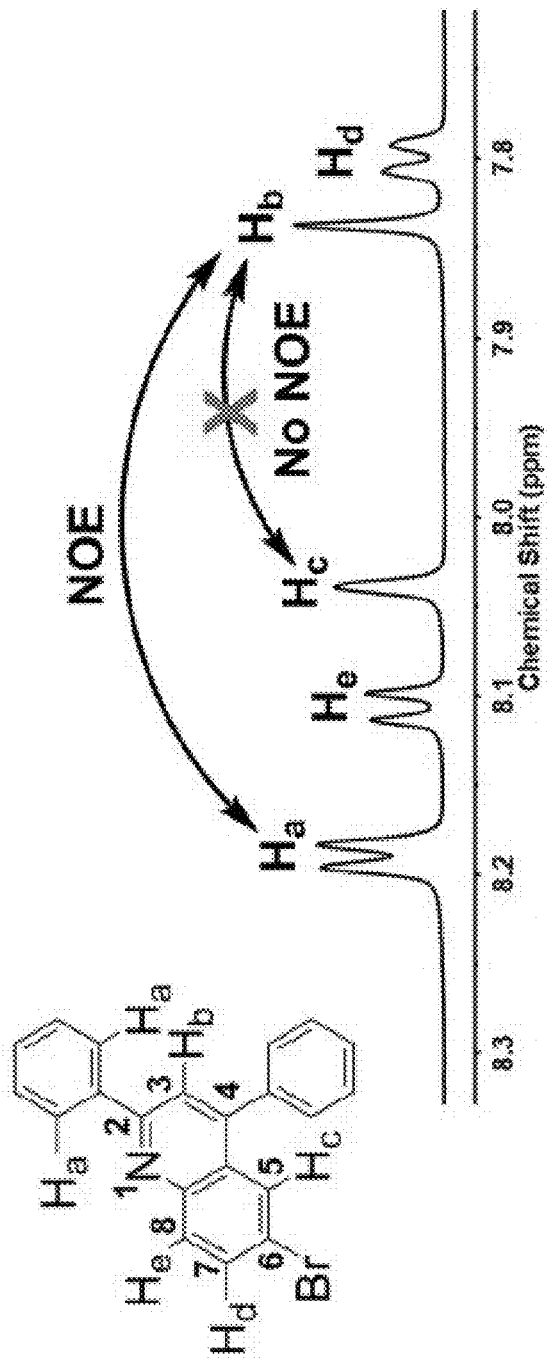
FIGS. 20A and 20B provide: A) the chemical structure and $^1$H NMR spectrum; and B) the X-ray crystal structure of quinoline in accordance with embodiments of the invention.
Figure 20B:
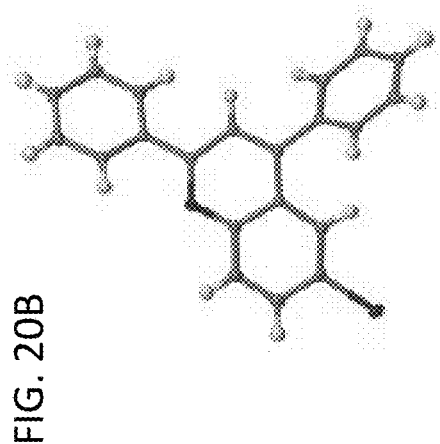

Model compound 2a (FIG. 3A was characterized with 1H NMR spectroscopy (FIGS. 20A and 20B). The 1H NMR spectrum featured three apparent doublets at 8.19 ppm, 8.11 ppm, and 7.80 ppm; a broad apparent singlet at 8.04 ppm; and a singlet at 7.84 ppm. The doublet at 8.19 ppm was assigned to the ortho position of one of the quinoline's pendant phenyl groups (Ha), and the narrow singlet at 8.04 ppm to position 3 on the quinoline ring (Hb). The remaining doublets at 8.11 ppm and 7.80 ppm were assigned to positions 7 and 8 of the quinoline ring, respectively (Hd and He), and the broad apparent singlet at 8.04 ppm to position 5 of the quinoline ring (Hc). These assignments were validated for all of the proton resonance peaks were further validated via 2D Correlation Spectroscopy (COSY) experiments.

It is important to note that the NMR spectra obtained for the reaction mixtures indicated the presence of a single regioisomer. To confirm this observation, the regioisomers' identities were evaluated via 1D-Nuclear Overhauser Effect (NOE) experiments. For compound 2a (FIG. 3A), a 2% enhancement in the NOE signal was observed between protons Ha and Hb on the quinoline ring, indicating their proximity. However, an enhancement in the NOE signal was not observed between Hb and Hc. These findings confirmed that only a single regioisomer was produced during the course of the reaction.

The absolute configuration of the product was further confirmed by growing crystals of compound 2a (FIG. 3A) and determining its structure with standard X-ray crystallography techniques (FIG. 20B). An analysis of the structure indicated that the pendant phenyl substituents were twisted out of planarity relative to the quinoline ring system, with the phenyl ring at position 2 of the quinoline possessing a smaller dihedral angle (24° than the phenyl ring at position 4 (45°). This difference was likely due to the absence of a hydrogen on the pyridinic nitrogen and the consequent reduced allylic strain at position 2. Thus, the X-ray crystallographic analysis unequivocally confirmed the identity of compound 2a (FIG. 3A).

Having validated the regioselectivity of the reaction conditions, the bifunctional AB-type monomer necessary for the polymerization reaction illustrated in FIG. 4A was prepared. The design of this monomer incorporated the requisite alkyne and aldimine functional groups within a single substrate, as well as an alkyl chain for enhanced solubility. By adapting the reaction conditions used to synthesize compound 1 (FIG. 3A), a Schiff base (compound 3 in FIG. 4A) was prepared in 43% isolated yield. Notably, the preparation of the monomer required inexpensive, commercially available reagents and only a single synthetic step.

Figure 21:
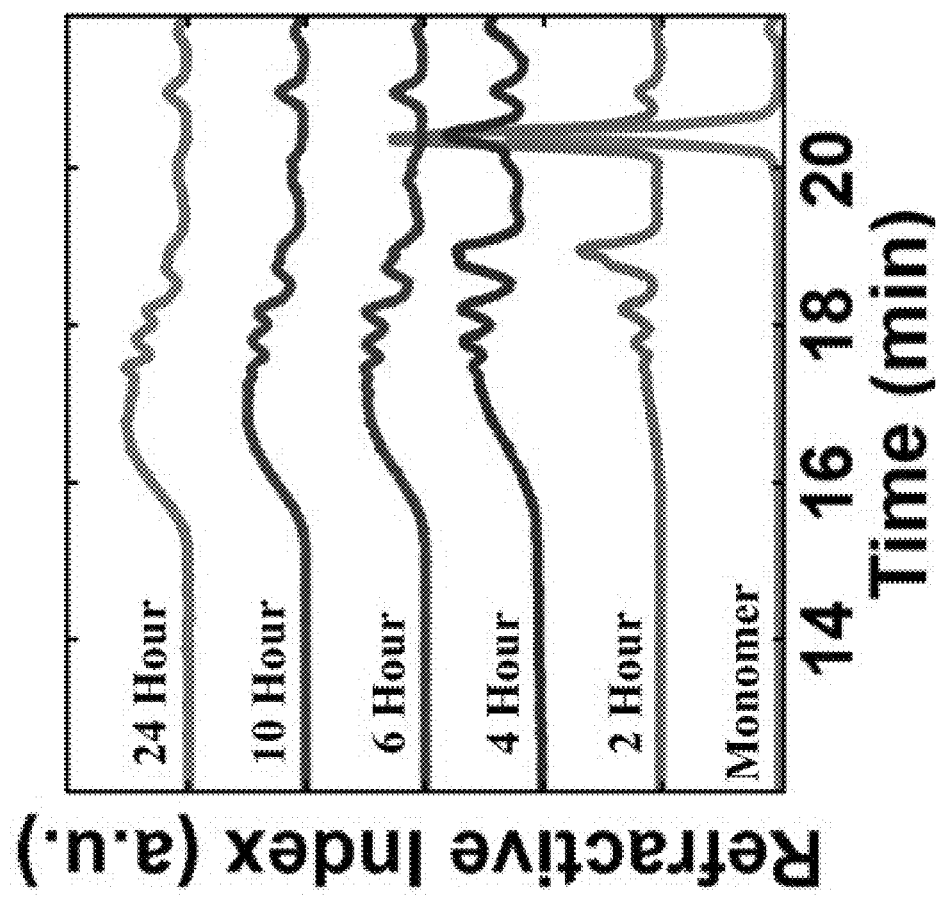
FIG. 21 provides the results of an SEC-RI analysis of a polymerization reaction in accordance with embodiments of the invention.

Then the reaction conditions optimized for the synthesis of compound 2 (FIG. 3A) were used to polymerize AB-type monomer 3 (FIG. 4A). The reaction progress was monitored by size exclusion chromatography with a refractive index detector (SEC-RI), as illustrated in FIG. 21. Initially, a chromatogram of a sample of the pure monomer showed a single sharp peak, as expected. Subsequently, 2 hours after the start of the reaction, monomer consumption was accompanied by the appearance of small oligomers. After 4 hours, the chromatogram indicated the presence of higher molecular weight species, and after 6 hours, the monomer was completely consumed, leading to the appearance of additional higher molecular weight species. Furthermore, after 10 hours, the chromatogram showed only a slight enhancement in the size of the polymeric product, with essentially no further increase observed after 24 hours. The gradual molecular weight build-up during the polymerization, as well as the high apparent polydispersity of the crude product, were consistent with a step-growth mechanism and closely resembled literature reports for Diels-Alder AB-type polymerizations. (See, e.g., Bailey, W. J. *Step Growth Polymerization*; Marcel Dekker: New York, 1972; Vol. 3; Schlüter, A. D. *In Synthesis of Polymers*; Wiley-VCH Verlag GmbH: 2008, p 459-483; and Tasdelen, M. A. *Polym. Chem.* 2011, 2, 2133-2145, the disclosures of which are incorporated herein by reference.)

Figure 22:
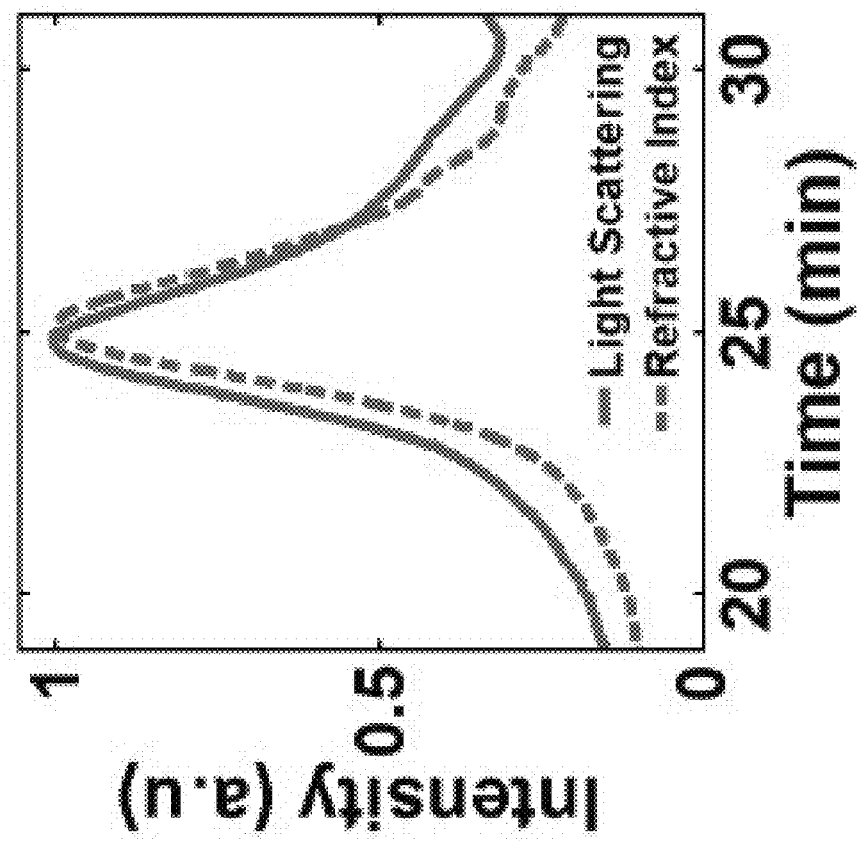
FIG. 22 provides the results of an SEC-MALS analysis of polyquinoline in accordance with embodiments of the invention.

Polymer 4 (FIG. 4A) was purified for further analysis. The reaction mixture was first quenched after a period of 24 hours by addition of aqueous sodium bicarbonate. Per literature precedent, the crude mixture was then treated with 2,3-dichloro-5,6-dicyano-1,4-benzoquinone (DDQ), definitively ensuring the rearomatization of the reaction products and the elimination of any potential remaining defects. (See, e.g., Meyers, A. I.; Wettlaufer, D. G. *J. Am. Chem. Soc.* 1984, 106, 1135-1136, the disclosure of which is incorporated herein by reference.) In turn a two-step chromatography/ethanol precipitation procedure was used to remove low molecular weight contaminants and isolate purified polymer 4 (FIG. 4A) in moderate yield. After purification, the polyquinoline was analyzed with size exclusion chromatography via a multi-angle light scattering detector (SEC-MALS) to obtain its unambiguous molecular weight; a representative light scattering chromatogram is shown in FIG. 22. The purified material possessed a number average molecular weight (Mn) of 10.1 kg mol−1 with a polydispersity index (PDI) of 1.04, corresponding to a degree of polymerization of 32. This material was used for all subsequent characterization steps.

Figure 23A:
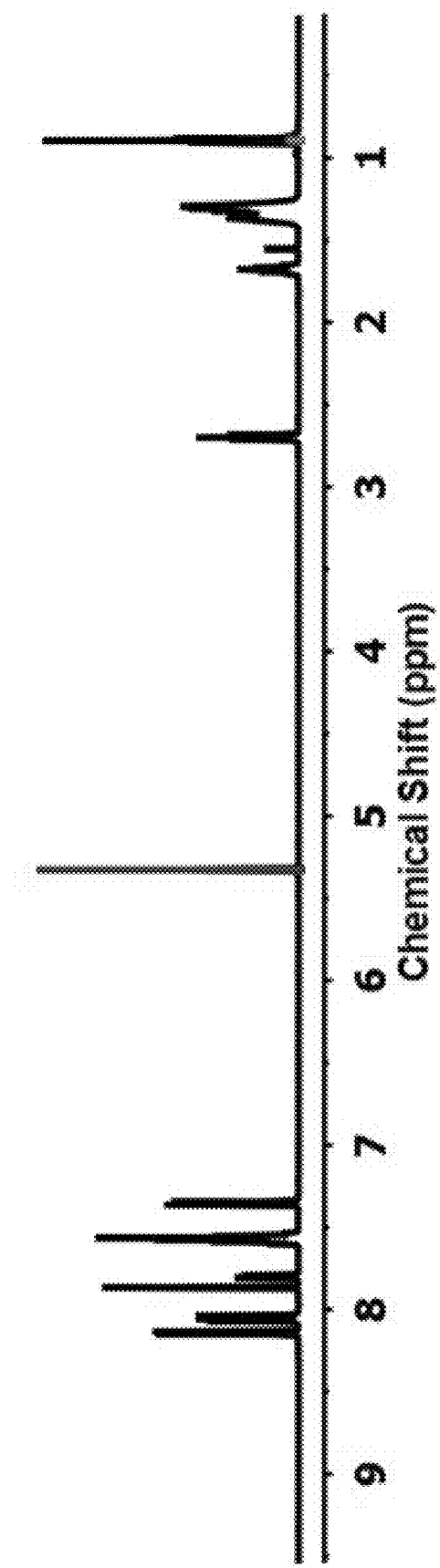
FIGS. 23A to 23C provide the structure and $^1$H NMR of: A) a model quinoline; B) a quinoline monomer; and C) a polyquinoline in accordance with embodiments of the invention.
Figure 23B:
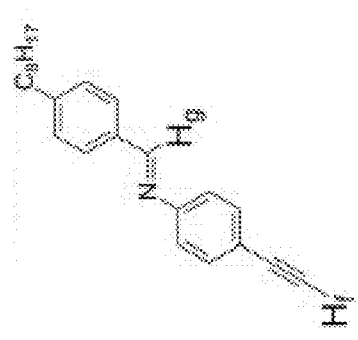
Figure 23B:
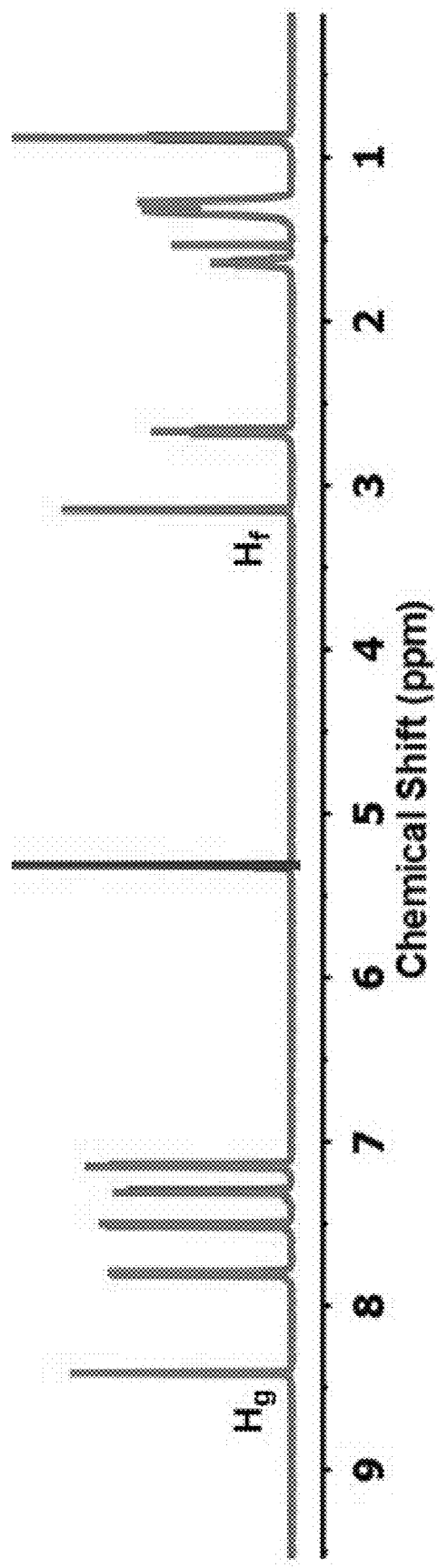
Figure 23C:
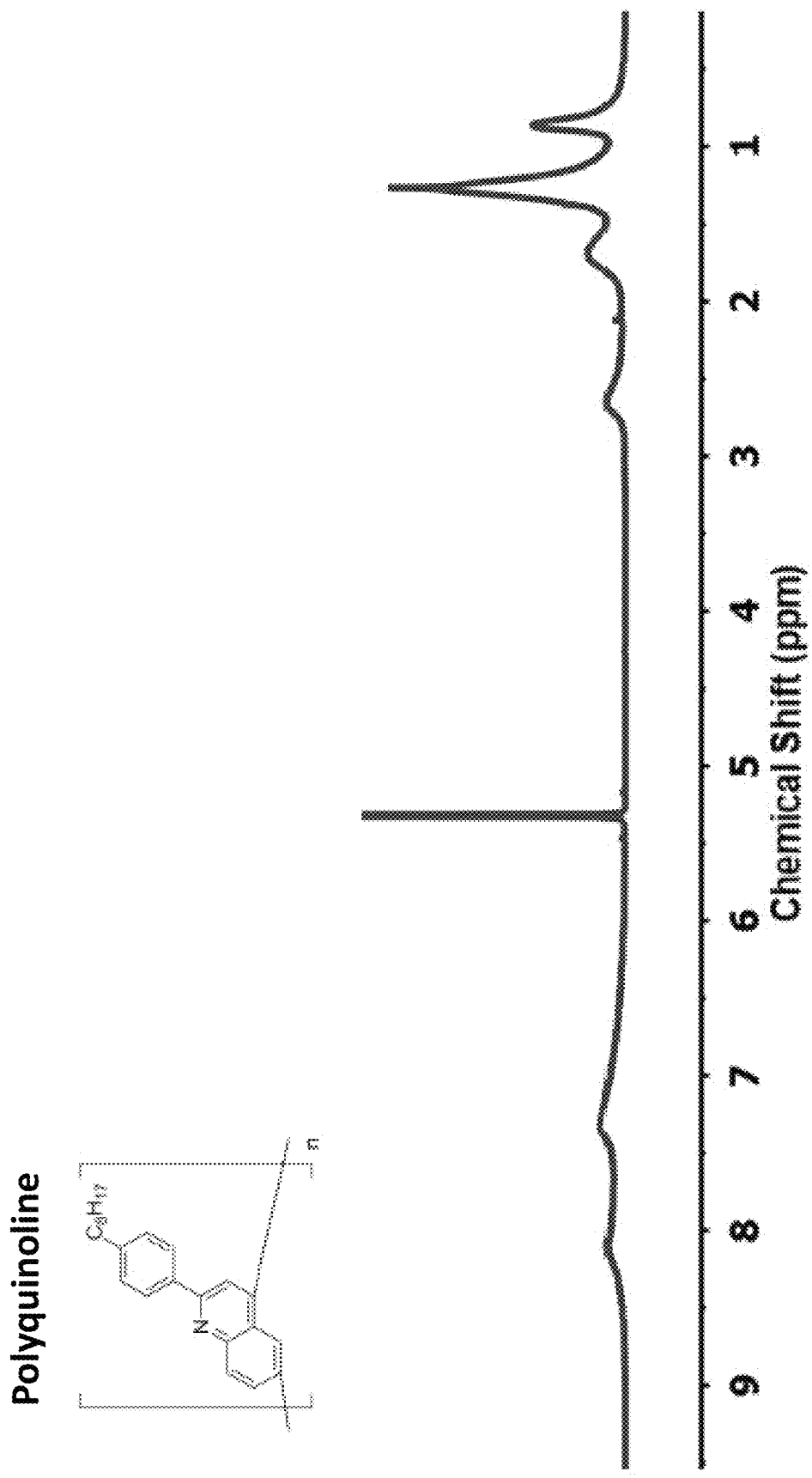

Purified polymer 4 (FIG. 4A) was then analyzed with 1H NMR spectroscopy by comparing its spectrum to the spectra of model quinoline 2b (FIG. 3A) and monomer 3 (FIG. 4A) as summarized in FIGS. 23A to 23C. First, it is noted that the NMR spectrum of compound 4 featured signal broadening, as expected for a polymeric material (FIG. 23C). The resonances of the aromatic peaks between 7.0 and 8.5 ppm (FIG. 23C) were also shifted downfield relative to the aromatic region of the monomer (FIG. 23B) but were in a similar location to those found for the aromatic region of the model quinoline (FIG. 23A). In addition, the NMR spectra of model compound 2b (FIG. 23A) and 4 (FIG. 23C) lacked the characteristic peaks at 3.15 ppm and 8.41 ppm associated with the alkyne and aldimine proton resonances, respectively. These peaks were prominent in the spectrum of monomer 3 (Hf and Hg in FIG. 23B). Finally, the integration ratio between the aromatic and aliphatic regions of compound 4 (FIG. 23C) was ~1:2, as would be expected based on the postulated structure and repeat unit of the polymer. In their totality, these observations indicate the formation of an extended aromatic system consisting of 4,6-linked quinoline subunits.

Figure 24:
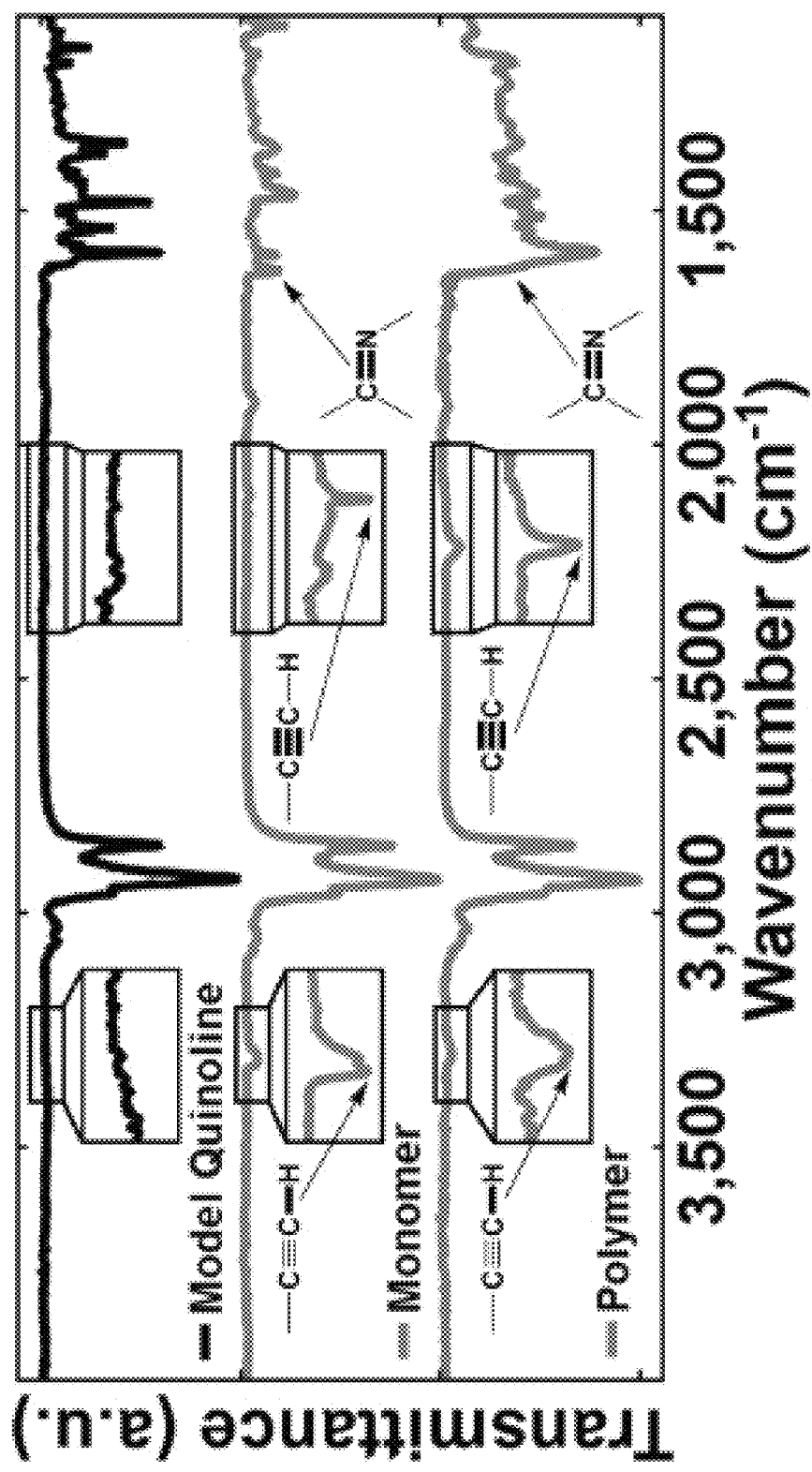
FIG. 24 provides FTIR spectra for a model quinoline, a quinoline monomer, and a polyquinoline in accordance with embodiments of the invention.

Polyquinoline (compound 4, FIG. 4A) was analyzed with FTIR spectroscopy, comparing its spectrum (FIG. 24) to those obtained for quinoline model compound 2b (FIG. 3A) and monomer 3 (FIG. 4A). The spectrum of compound 4 (FIG. 4A) revealed a cluster of peaks at 1500 $cm^{-1}$-1600 $cm^{-1}$, which could be attributed in part to its aromatic quinoline core. This spectrum also featured broad peaks at 1616 $cm^{-1}$, 2216 $cm^{-1}$, and 3298 $cm^{-1}$ that can be assigned based on literature precedent to the polymer's imine, alkyne CC, and alkyne CH terminal functionalities, respectively (FIG. 24, polymer trace). These proposed assignments were corroborated by the spectrum of monomer 3 (FIG. 4A), which featured peaks at 1626 $cm^{-1}$, 2146 $cm^{-1}$, and 3319 $cm^{-1}$, presumably corresponding to its imine, alkyne CC, and alkyne CH functionalities, respectively (FIG. 24, monomer trace). The assignments were further supported by the spectrum of model compound 2b (FIG. 3A), which lacked the imine and alkyne peaks but did feature a cluster of peaks at 1500 $cm^{-1}$-1600 $cm^{-1}$, likely in part due to its quinoline core (FIG. 24, model quinoline trace). Together, the observations provided additional confirmation of the identity of compound 4 (FIG. 4A) and indicated that some of the polymer's imine and alkyne terminal groups (which were not readily detected with 1H NMR) probably remained intact after the reaction and workup.

Figure 25:
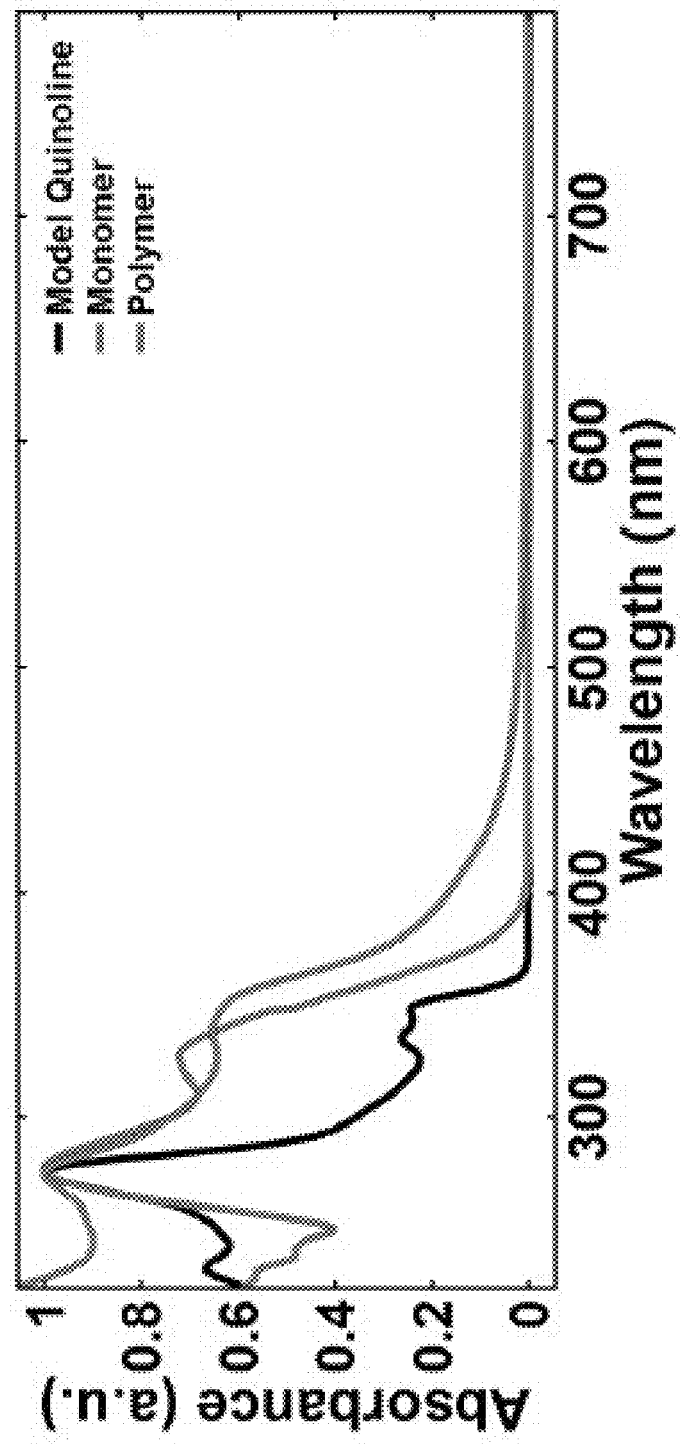
FIG. 25 provides normalized UV-vis absorbance spectra for a model quinoline, a quinoline monomer and a polyquinoline in accordance with embodiments of the invention.

Finally, the optical properties of polymer 4 (FIG. 4A) were investigated with UV-Vis spectroscopy (FIG. 25). The spectrum obtained for compound 4 (FIG. 4A) featured broad peaks at 275 nm and 338 nm, with an absorption onset at 460 nm (FIG. 25, polymer trace). In comparison, the spectrum of model quinoline 2b (FIG. 3A) featured sharper peaks at 275 nm, 335 nm, and 348 nm, with an absorption onset at 365 nm (FIG. 25, model quinoline); and the spectrum of monomer 3 (FIG. 4A) featured peaks at 277 nm and 327 nm, with an absorption onset at 386 nm (FIG. 25, monomer trace). The red shift in the absorption onset and the broadening observed for the polyquinoline's spectrum, relative to the spectra of both the monomer and the model quinoline, were indicative of the formation of a macromolecule with an extended π-conjugated system.

Example 2

AA/BB-Type aza-Diels-Alder Reaction

Model crowded biquinoline (FIG. 6 compounds 2a-c) were synthesized via the Povarov reaction, as illustrated in FIG. 6. Established literature protocols were used to form bis(aldimines) 1a-c (FIG. 6). Next, compounds 1a-c (FIG. 6) were reacted with phenylacetylene in the presence of $BF_3.OEt_2$ as a Lewis acid mediator and chloranil as an oxidant, furnishing biquinolines 2a-c (FIG. 6). Overall, the synthesis utilized mild conditions and commercial starting materials to produce regioisomerically pure products in excellent yield.

Figure 26A:
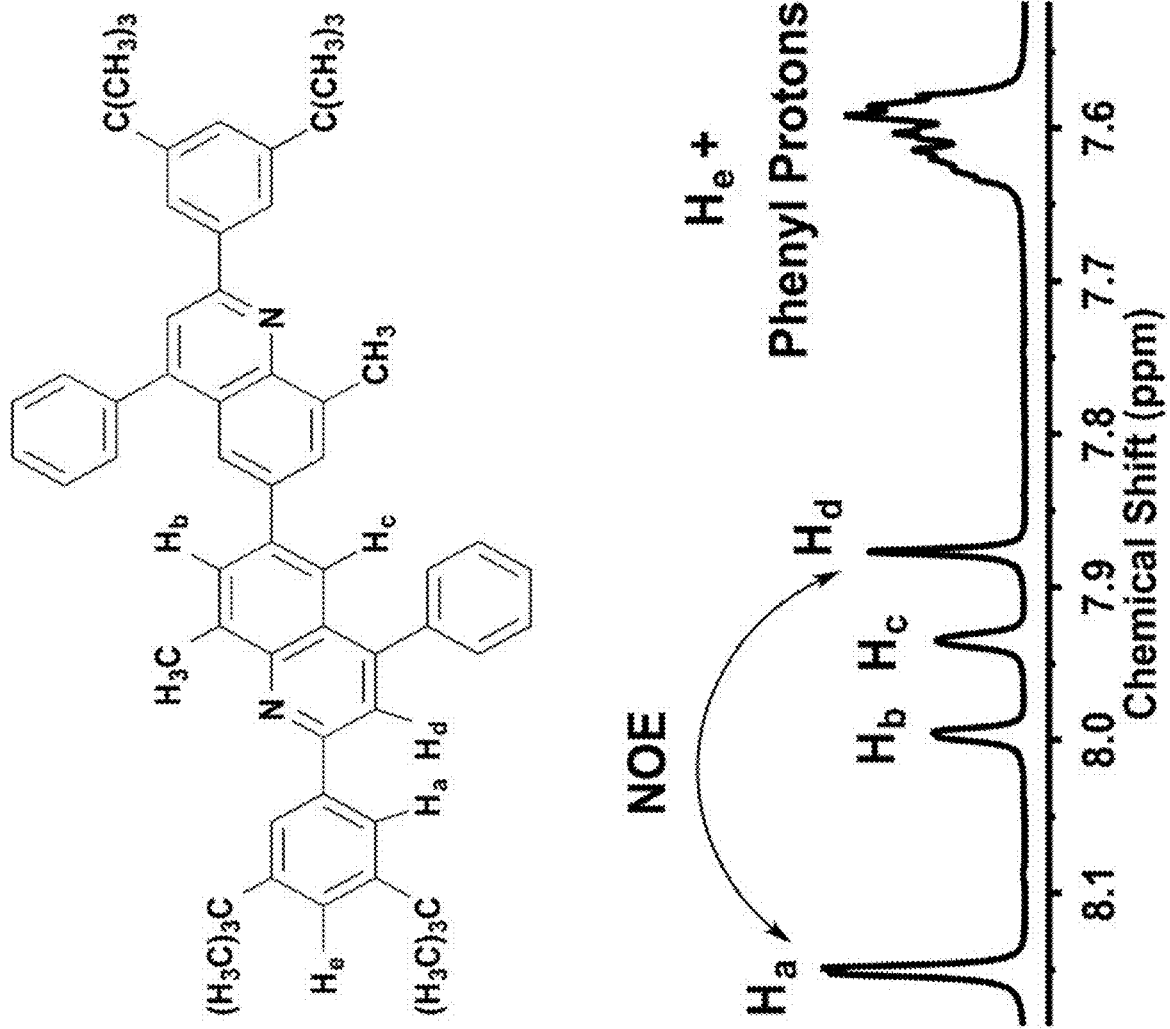
FIGS. 26A and 26B provide: A) a chemical structure and $^1$H NMR spectra; and B) a X-ray crystal structure for a biquinoline in accordance with embodiments of the invention.

Model compounds 2a-c (FIG. 6) were characterized with nuclear magnetic resonance (NMR) spectroscopy and mass spectrometry. As an example, the aromatic region of the 1H NMR spectrum for compound 2b (FIG. 6) is illustrated in FIG. 26A. This spectrum featured two apparent doublets at 8.15 and 7.99 ppm; a broad singlet at 7.94 ppm; a sharp singlet at 7.88 ppm; and a singlet, which presumably overlapped with a multiplet, at 7.60 ppm. The doublet at 8.15 ppm was tentatively to the protons at the ortho positions of the quinolines' tert-butyl-substituted phenyl groups (Ha) and the doublet at 7.99 ppm to the proton at position 7 of the quinoline cores (Hb). In turn the broad singlet at 7.94 ppm was assigned to the proton at position 5 of the quinoline cores (Hc) and the sharp singlet at 7.88 ppm to position 2 of the quinoline cores (Hd). Finally, the complex signal at 7.60 ppm was attributed to the proton at the para positions of the quinolines' tert-butyl-substituted phenyls (He), as well as to an overlapping multiplet from the quinolines' unsubstituted pendant phenyls. The assignments for all of the proton resonances were further validated by 2D correlation spectroscopy (COSY) experiments.

To gain insight into the regioisomeric identity of the products, w the Nuclear Overhauser Effect (NOE) was observed (FIG. 26A). For these experiments, compound 2b (FIG. 6) was analyzed because its spectrum was more straightforward to interpret. A clear enhancement in the NOE signal between proton Ha of the quinoline systems and proton Hd of the pendant tert-butyl-substituted phenyl groups can be observed, confirming their proximity (FIG. 26A). This observation suggested that the reaction conditions likely produced only a single regioisomer, in agreement with previous findings for analogous quinoline and benzoquinoline systems.

Figure 26B:
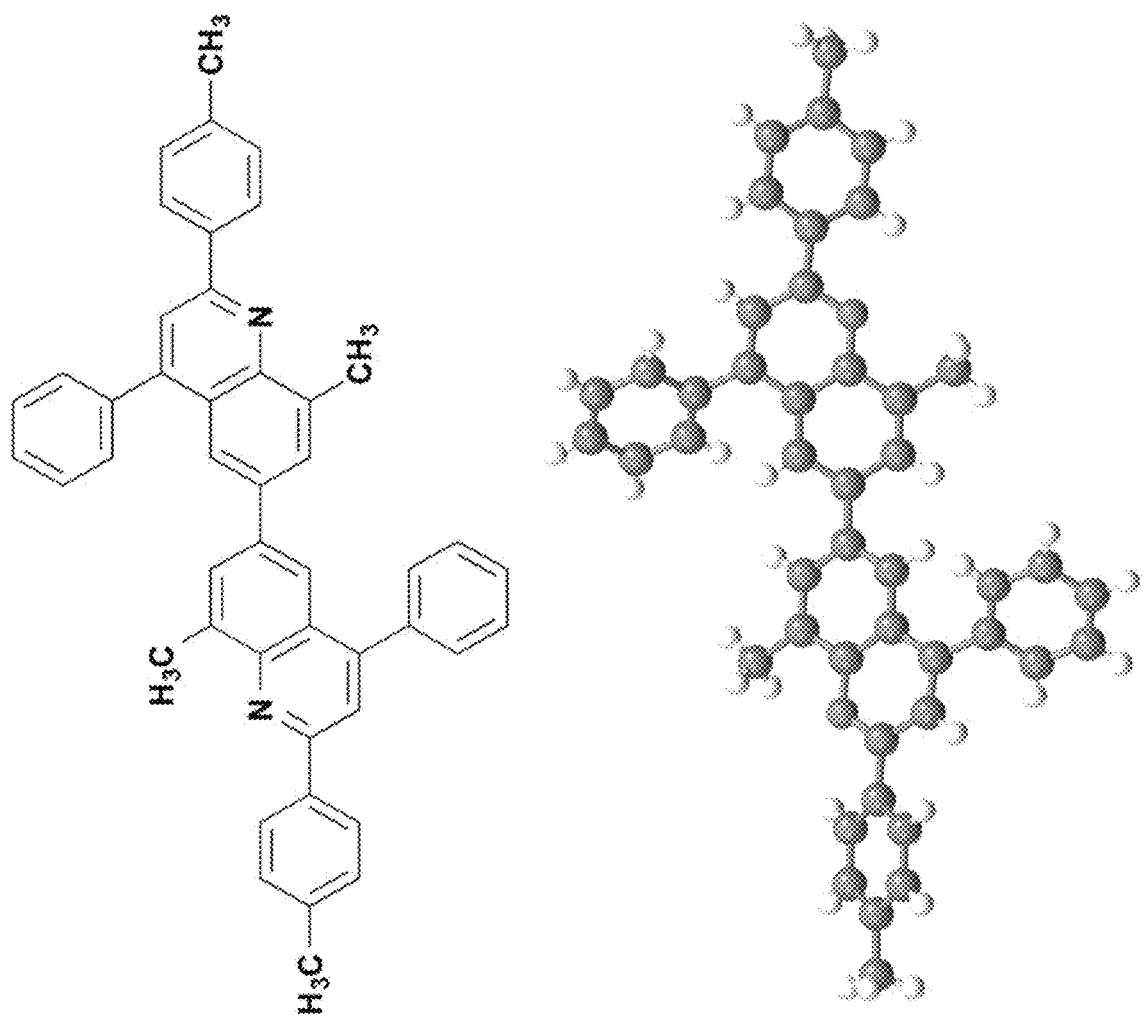

The connectivity and absolute configurations of the compounds was further confirmed with X-ray crystallography (FIG. 26B). For these experiments, compound 2a (FIG. 6) was analyzed because it readily produced crystals of sufficient quality for X-ray diffraction analysis. The crystal structure revealed that the quinolines featured pendant methyl-substituted phenyl rings at the 2 position and pendant unsubstituted phenyl rings at the 4 position, validating the NOE analysis (FIG. 26B). Moreover, it was found that the connected aromatic systems (quinolines and phenyls) were all twisted out of planarity relative to one another, presumably due to steric interactions (FIG. 26B). Together with the COSY experiments, the crystal structure definitively confirmed the identity of compound 2a (FIG. 6), and thus, the regioselectivity of the reaction conditions.

Figure 27A:
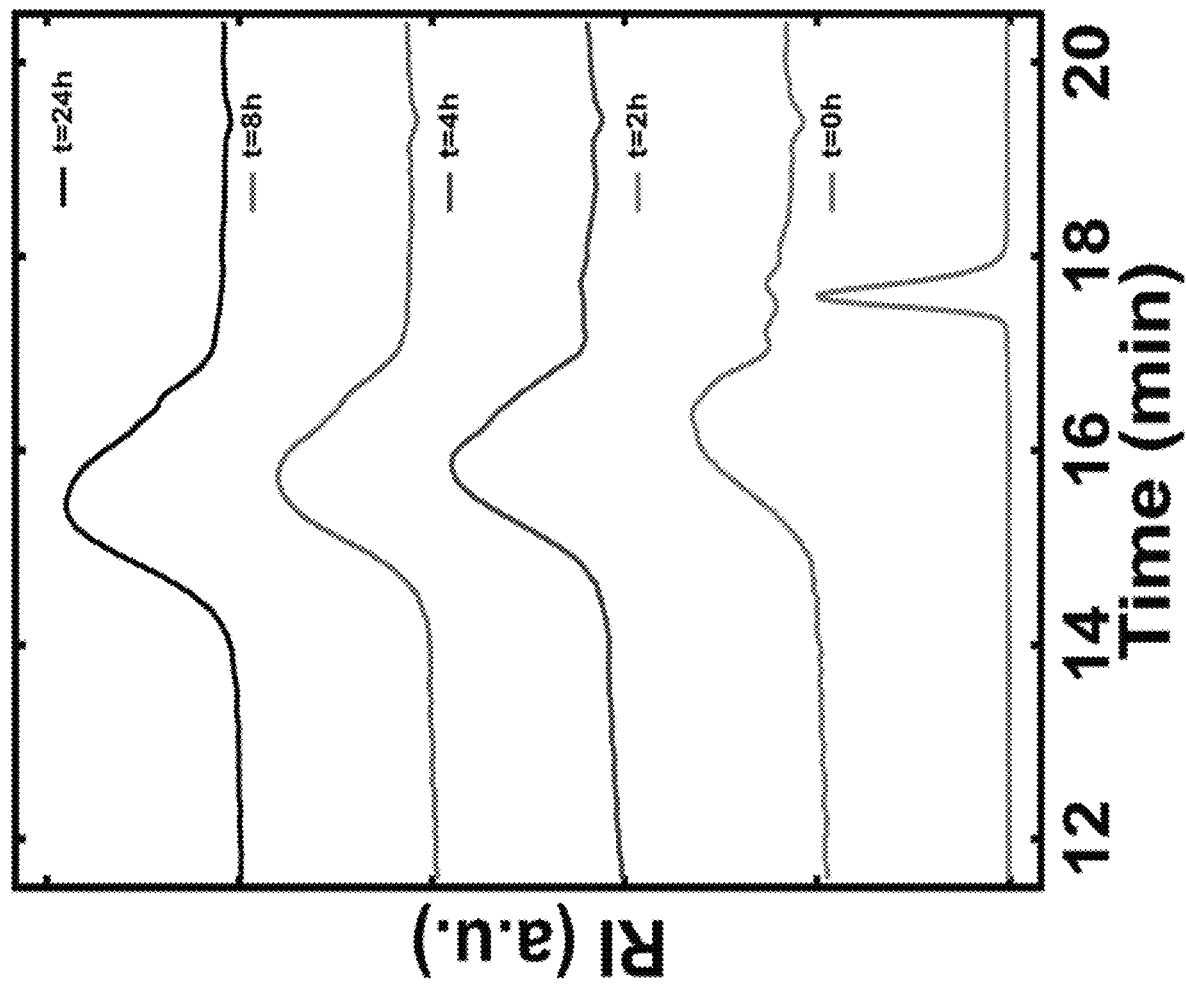
FIGS. 27A and 27B provide an SEC-RI analysis: A) during a polymerization reaction; and B) after polymerization for a polyquinoline in accordance with embodiments of the invention.

Having evaluated the regiospecificity of the strategy, polyquinolines were prepared, as illustrated in FIG. 7. Here, diimine 1c (FIG. 7) was reacted with diethynyl benzene in an AA/BB-type polymerization under the conditions developed for the synthesis of compounds 2a-c (FIG. 6). The progress of this polymerization was monitored by size exclusion chromatography with a refractive index detector (SEC-RI), as illustrated by the representative chromatograms in FIGS. 27A and 27B. Initially, a chromatogram of the starting materials showed a single sharp peak, corresponding to monomer 1c (FIG. 27A, 0h trace). Subsequently, after 2 h, monomer consumption was accompanied by the appearance of low molecular weight oligomers (FIG. 27A). In turn, after 4 h, the monomer was nearly completely consumed, leading to the appearance of additional higher molecular weight species (FIG. 27A). Furthermore, after 8 h, the chromatogram showed only a slight enhancement in the size of the polymeric product (FIG. 27A), with an additional modest increase found after 24 h (FIG. 27A). The buildup in molecular weight observed during the reaction was consistent with a step-growth mechanism and resembled literature precedent for Diels-Alder AA/BB-type polymerizations.

Figure 27B:
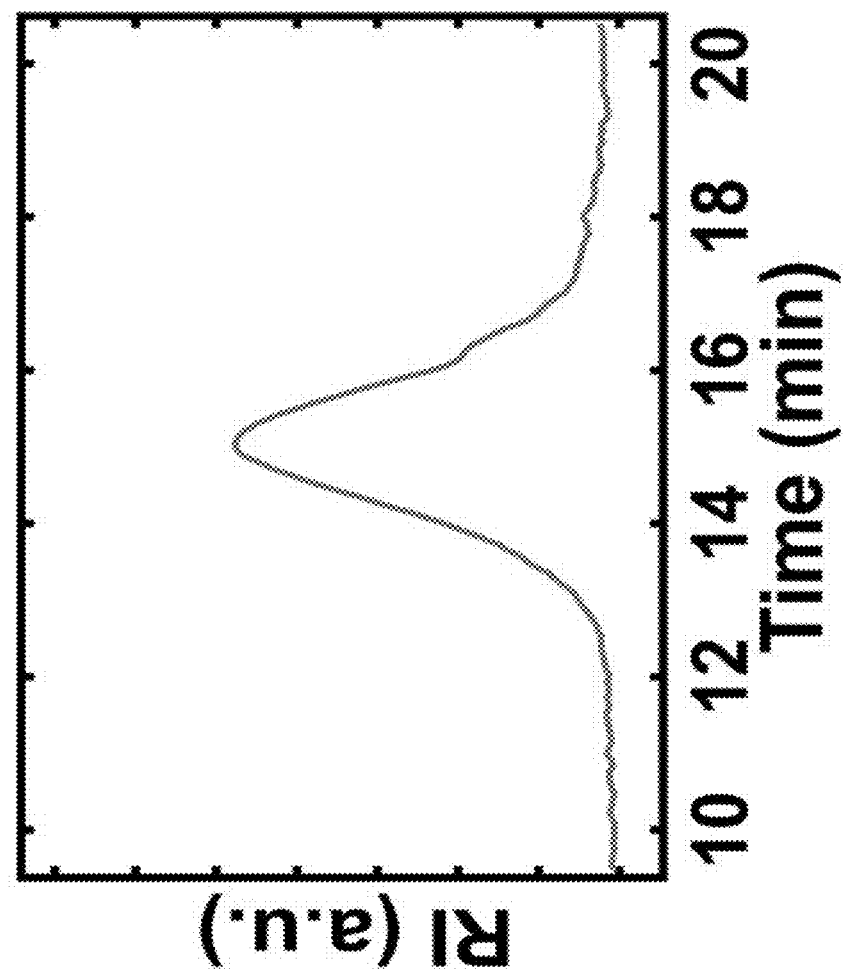

Polymer 3c (FIG. 7) was processed and analyzed with SEC-RI. To this end, the reaction was first quenched through the addition of aqueous sodium bicarbonate after a period of 72 h. Subsequently, compound 3c (FIG. 7) was treated with 2,3-dichloro-5,6-dicyano-1,4-benzoquinone (DDQ), ensuring rearomatization of the quinoline core, and then precipitation this polymer from ethanol, ensuring removal of any residual low molecular weight contaminants. FIG. 27B shows a representative chromatogram obtained for compound 3c (FIG. 7) after precipitation; the polyquinoline possessed a weight average molecular weight (Mw) of 33.2 kg mol$^{-1}$, a number average molecular weight (Mn) of 14.8 kg mol$^{-1}$, and a polydispersity index (PDI) of 2.24. The polydispersity of the polymer further supported the notion of a step-growth mechanism and again matched literature precedent for Diels-Alder AA/BB-type polymerizations.

Figure 28A:
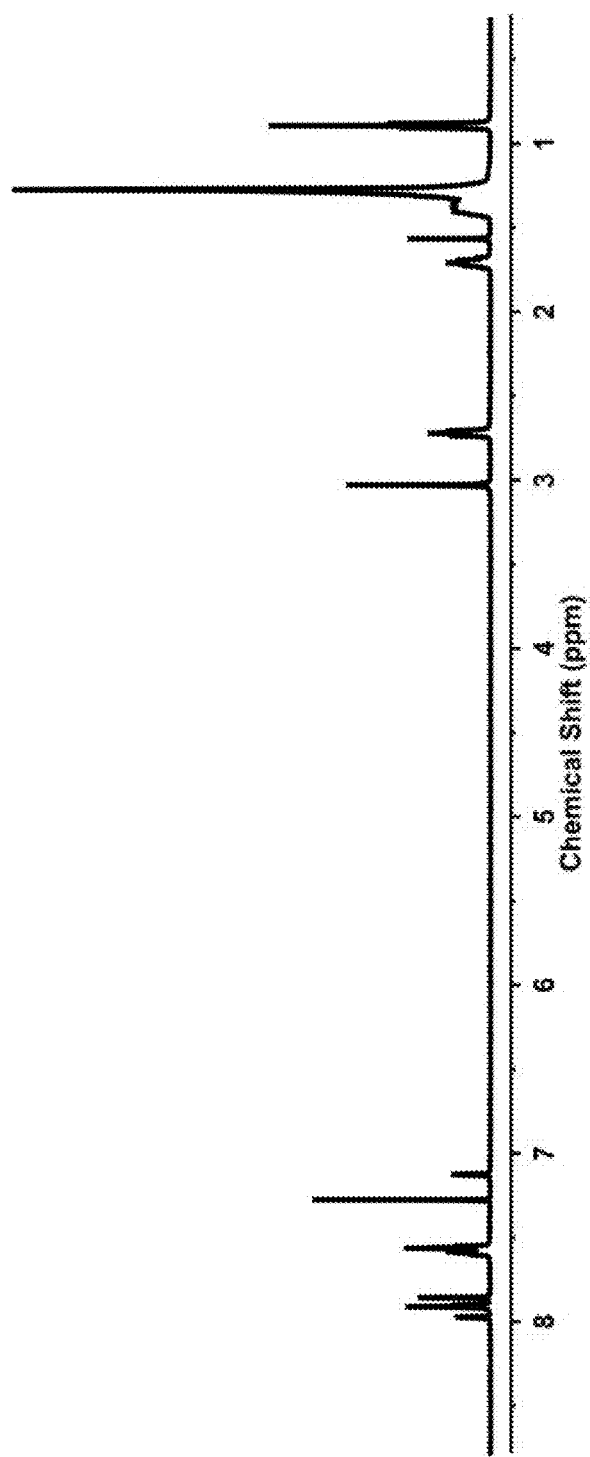
FIGS. 28A and 28B provide the chemical structure and $^1$H NMR spectra for: A) a model quinoline compound; and B) polyquinoline in accordance with embodiments of the invention.

Polyquinoline 3c was further analyzed (FIG. 7) via 1H NMR spectroscopy, with model biquinoline 2c (FIG. 6) serving as a useful reference. It is first noted that the 1H NMR spectra of both compound 3c (FIG. 28B) and compound 2c (FIG. 28A) featured resonances between 7.0 and 8.5 ppm in the aromatic region, which could be associated with the quinoline and phenyl moieties, as well as resonances between 0.0 and 3.0 ppm in the alkyl region, which could be associated with the methyl and dodecyl functionalities. Although the observed signals were in similar positions for both the polymer and the model compound, the spectrum of compound 3c (FIG. 28B) featured significant broadening relative to the spectrum of compound 2c (FIG. 28A), as expected for a polymeric material. Moreover, the integration ratio between the aromatic and alkyl regions of compound 3c was ~1:6, matching predictions based on the structure of the model biquinoline and the repeat unit of the polyquinoline. Overall, the analysis confirmed the formation of an extended macromolecule comprised of linked biquinoline and phenyl subunits.

Figure 29:
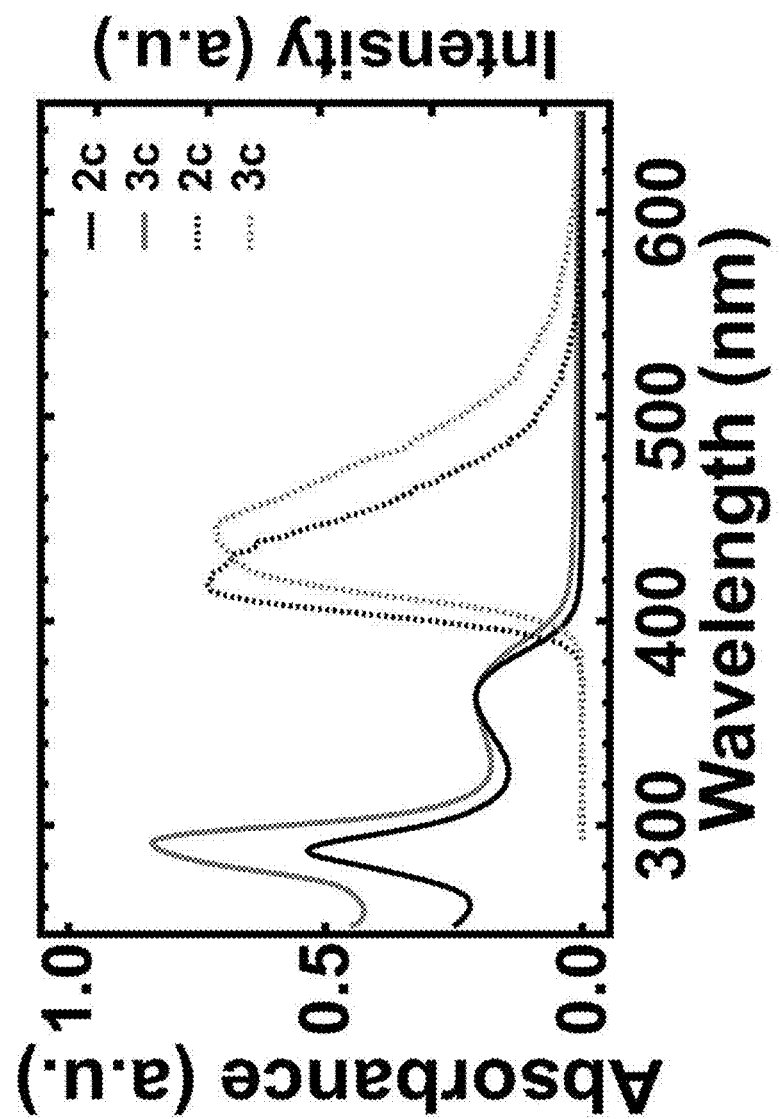
FIG. 29 provides normalized UV-vis absorbance spectra for a model quinolines and polyquinolines in accordance with embodiments of the invention.

The electronic properties of polyquinoline 3c (FIG. 7) and model biquinoline 2c (FIG. 6) were investigate with UV-vis spectroscopy (FIG. 29). The spectrum obtained for compound 3c featured peaks at 291 nm and 363 nm, as well as an absorption onset at 435 nm (FIG. 29, solid 3c). In comparison, the spectrum obtained for compound 2c featured peaks at 288 nm and 363 nm, as well as an absorption onset of 425 nm (FIG. 29, solid 2c). Moreover, the spectrum of the polyquinoline was broadened and tailed into the red, relative to the one of the model biquinoline. Overall, the observations were consistent with the formation of a π-conjugated macromolecule.

Next the photophysical properties of polyquinoline 3c and model biquinoline 2c (FIGS. 6 & 7) were observed with fluorescence spectroscopy. The emission spectrum obtained for compound 3c featured a peak at 419 nm (FIG. 29, dashed 3c), while the emission spectrum obtained for compound 2c featured a peak at 446 nm (FIG. 29, dashed 2c). Thus, the polyquinolines possessed a more substantial Stokes shift, compared to the biquinoline. These findings were again consistent with the formation of a 7-conjugated macromolecule.

Figure 30:
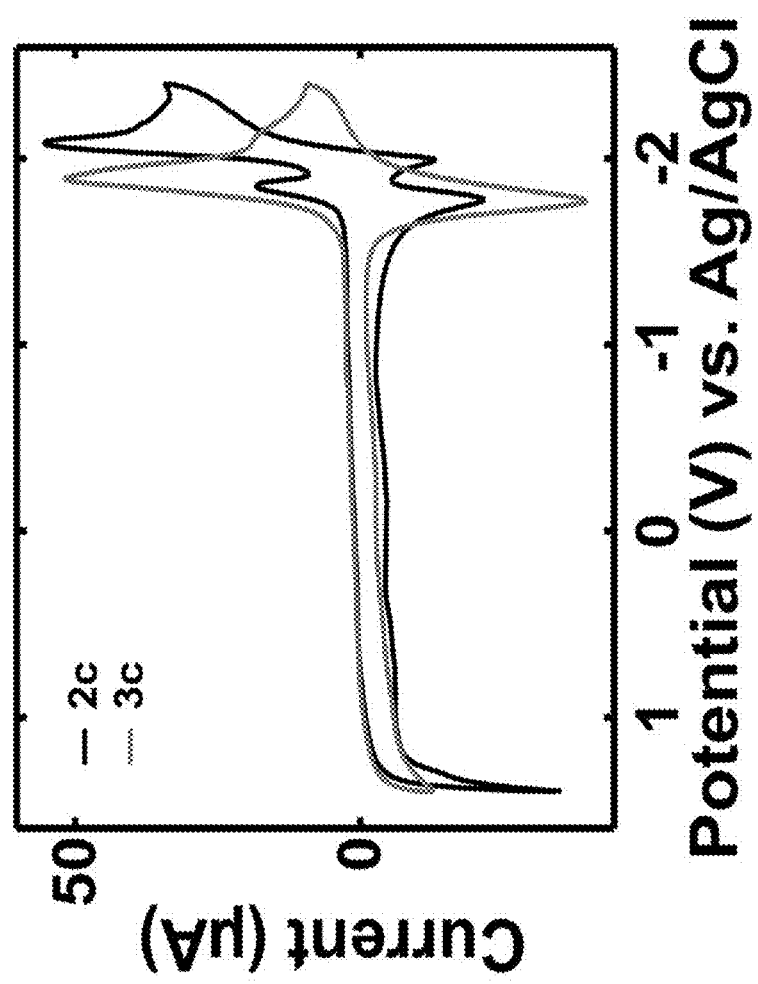
FIG. 30 provides cyclic voltammetry for thin films of a model quinoline and polyquinoline in accordance with embodiments of the invention.

In addition, the electrochemical properties of thin films from both polyquinoline 3c (FIG. 7) and model biquinoline 2c (FIG. 6) were studied with cyclic voltammetry (FIG. 30). At reductive potentials, the voltammogram obtained for compound 3c featured a quasi-reversible redox couple with a midpoint potential of −1.83 V vs. Ag/AgCl and an irreversible cathodic wave with a peak potential of −2.13 V vs. Ag/AgCl (FIG. 30, 3c trace). The voltammogram obtained for compound 2c was similar and featured two quasi-reversible redox couples with midpoint potentials of −1.81 V vs. Ag/AgCl and −2.04 V vs. Ag/AgCl (FIG. 30, 2c trace). Moreover, within the accessible potential window, the voltammograms obtained for both the polyquinoline and the biquinoline did not exhibit any redox activity at oxidative potentials. Overall, the electrochemical measurements demonstrated that the redox properties of the polymers and model compounds were similar.

Figure 31:
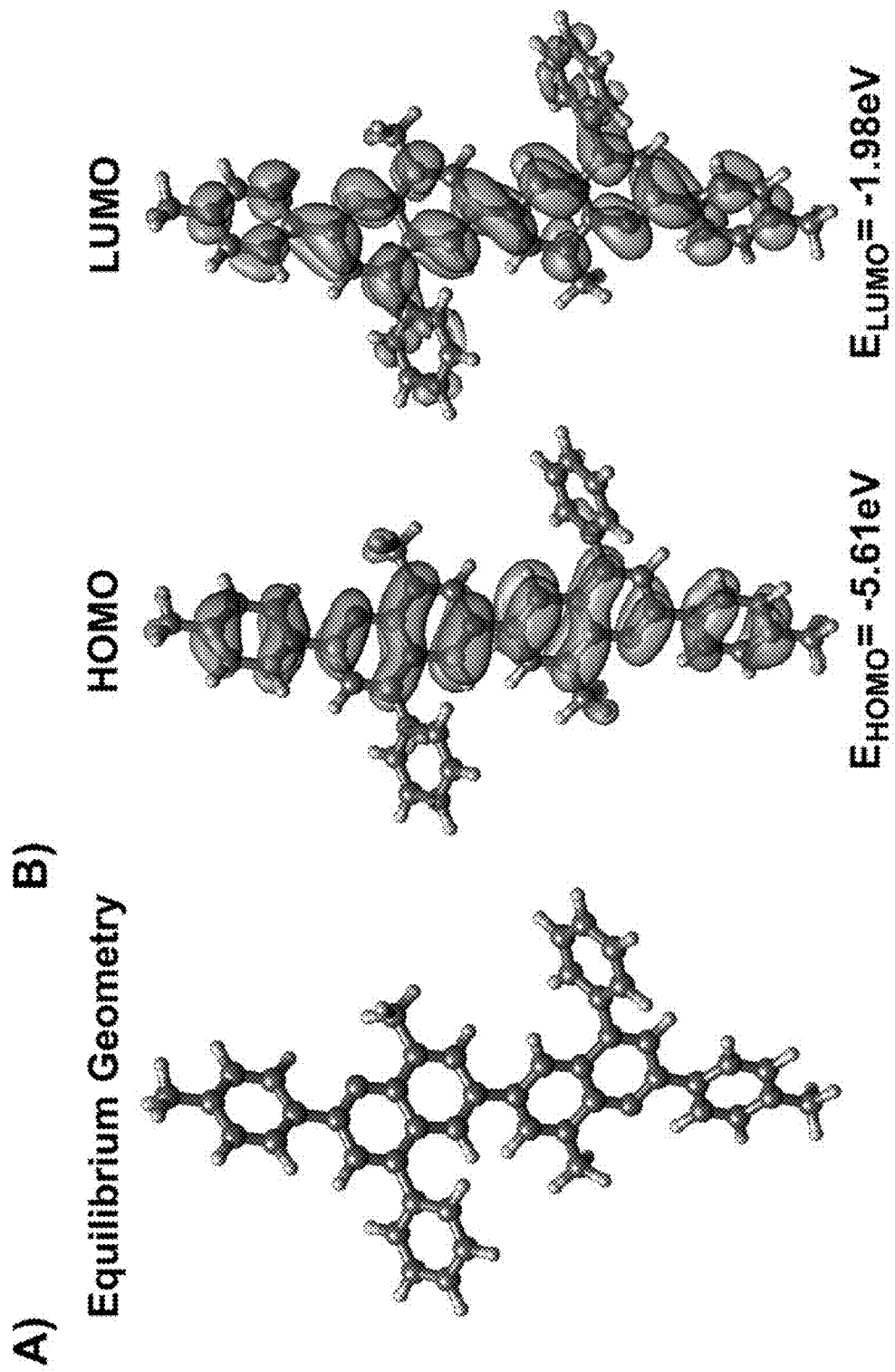
FIGS. 31A and 31B provide: A) the energy minimized equilibrium for a model quinoline; and B) the HOMO and LUMO for the model quinoline in accordance with embodiments of the invention.

Finally, to gain additional insight into the electronic properties of the materials and interpret the electrochemical findings, density functional theory (DFT) calculations were performed for model biquinoline 2c (FIG. 6). From these calculations, the equilibrium molecular geometry were obtained, as well as the shapes and energies of this molecule's highest occupied molecular orbital (HOMO) and lowest unoccupied molecular orbital (LUMO) (FIG. 31). It was thus possible to assign the first redox couple observed at −1.81 V vs. Ag/AgCl for the biquinoline to its LUMO. It was found that the electrochemically-determined LUMO energy of −2.6 eV was similar to the theoretically-calculated LUMO energy of −2.0 eV, indicating that compound 2c possessed a large electron affinity (FIG. 31B). Moreover, a HOMO energy of −5.7 eV was extracted from the DFT calculations (FIG. 31B), indicating that compound 2c (FIG. 6) possessed a large ionization potential. This analysis suggested that materials based on the crowded biquinoline motif hold promise as n-type organic semiconductors.

Example 3

Polybenzoquinolines benzoquinoline model compounds 3a,b and 5a,b were synthesized via the Povarov reaction, as illustrated in FIG. 8A. To prepare model compounds 3a and 3b (FIG. 8), first aldimines 1a and 1b were formed via a known literature protocol. Then naphthyl alkyne 2 was reacted with 1a or 1b in the presence of BF$_3$OEt$_2$ as the Lewis acid mediator and chloranil as the sacrificial oxidant, producing monomeric benzoquinolines 3a or 3b (FIG. 8), respectively. Next, to prepare dimeric model compounds 5a and 5b (FIG. 8), the pendant bromides of compounds 3a and 3b are converted to alkynes, forming compounds 4a and 4b (FIG. 8), respectively. Alkyne 4a was then reacted with aldimine 1a and alkyne 4b with aldimine 1b, producing benzoquinolines 5a and 5b (FIG. 8). This linear synthetic strategy furnished the desired regioisomerically pure products in moderate yields.

Pentameric compound 8 was then prepared as a longer model benzoquinoline (FIG. 8B). To construct compound 8, compound 5b was used as the sole starting material and generated complementary building blocks 6 and 7. Thus, to synthesize compound 6, the pendant bromide of 5b was converted to an alkyne, and to synthesize compound 7, the acetyl-protected amine of 5b was converted to an aldimine. Subsequently alkyne 6 and aldimine 7 were combined under Povarov conditions, furnishing compound 8. Here, by independently modifying the bromide and amine termini of the precursors, an arduous linear synthesis was avoided to produce a benzoquinoline macromolecule.

Figure 32A:
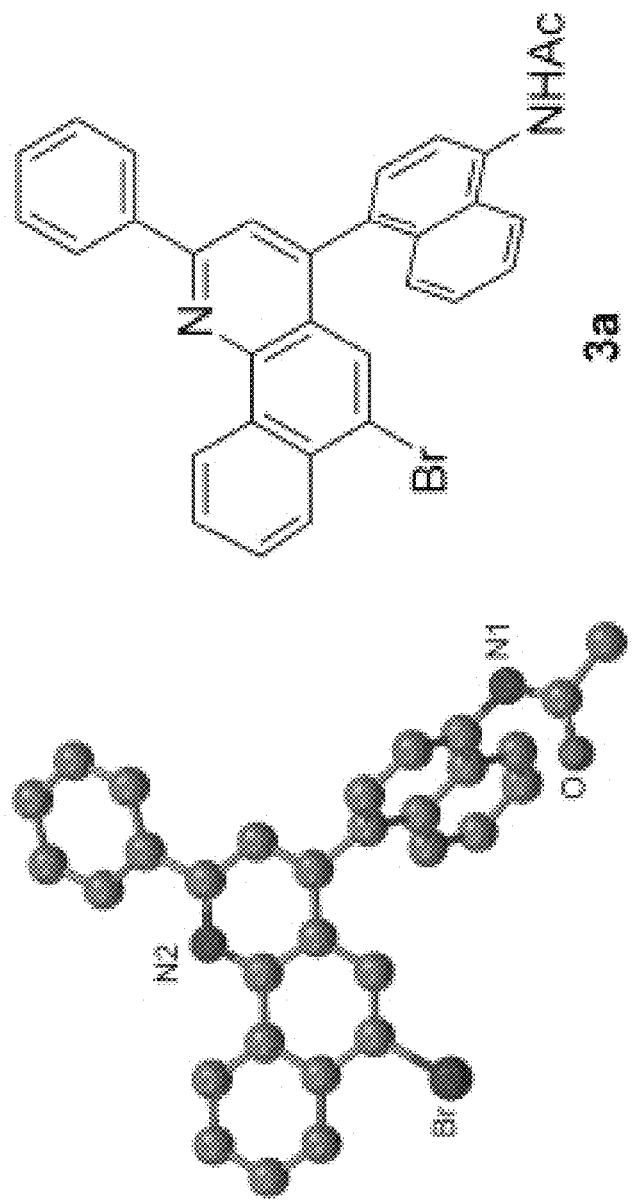
FIGS. 32A and 32B provide the X-ray crystal structures and chemical structures for two benzoquinolines in accordance with embodiments of the invention.
Figure 32B:
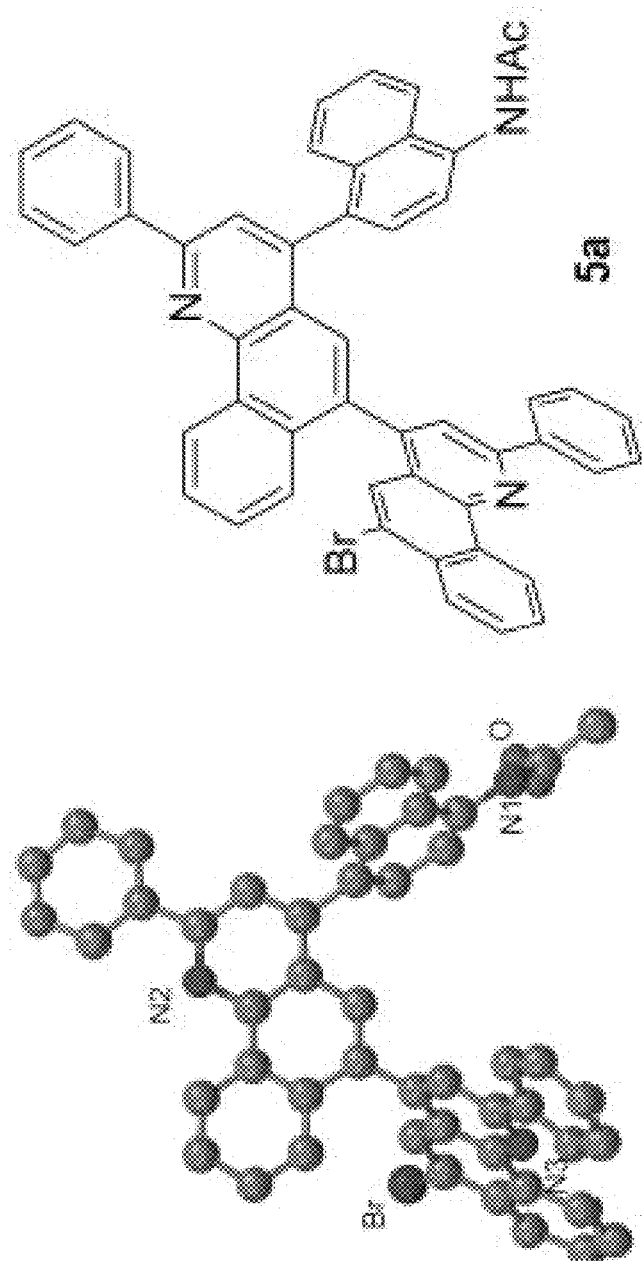

Benzoquinoline model compounds (3a, 3b, 5a, 5b, and 8 from FIG. 8) were characterized with 1H and 13C nuclear magnetic resonance (NMR) spectroscopy, mass spectrometry (MS), and/or X-ray crystallography. In particular, crystals of 3a and 5a were grown and their solid-state structures determined through standard X-ray crystallography techniques (FIGS. 32A and 32B). Although the resolution for compound 5a was quite poor, both crystal structures confirmed that the reaction conditions produced only the desired regioisomers and connectivity, as further supported by a detailed NMR analysis for compound 3b. The crystal structures also revealed that the naphthyl moieties of both compounds 3a and 5a were almost completely orthogonal with respect to their neighboring benzoquinoline subunits (FIGS. 32A & 32B) and that the two constituent benzoquinoline subunits of compound 5a were twisted out of planarity with respect to one another in the solid state (FIG. 32B). Altogether, these experiments definitively confirmed the identity of the model compounds.

With the model compounds in hand, elongated benzoquinoline macromolecules were synthesized. Thus, polybenzoquinoline 11a was prepared through polymerization of AB-type bifunctional monomers via the Povarov reaction. Therefore it was possible to produce monomer 10a from 4-iodonaphthylamine 9 in only three steps (FIG. 8B). The design of this monomer incorporated the requisite alkyne and aldimine functional groups within a single substrate, as well as an alkyl chain for enhanced solubility. The reaction conditions optimized for the synthesis of compounds 3b, 5b, and 8 (FIG. 8A) were then used to polymerize 10a (FIG. 8B). The resulting reaction mixture was analyzed via size exclusion chromatography with a refractive index detector (SEC-RI), and through calibration with standards, an Mn of 2730 g mol$^{-1}$, an Mw of 5420 g mol$^{-1}$, and a PDI of 1.98 were obtained for compound 11a. This product's polydispersity was consistent with a step-growth polymerization mechanism, as expected for a Diels-Alder-type reaction.

Figure 33:
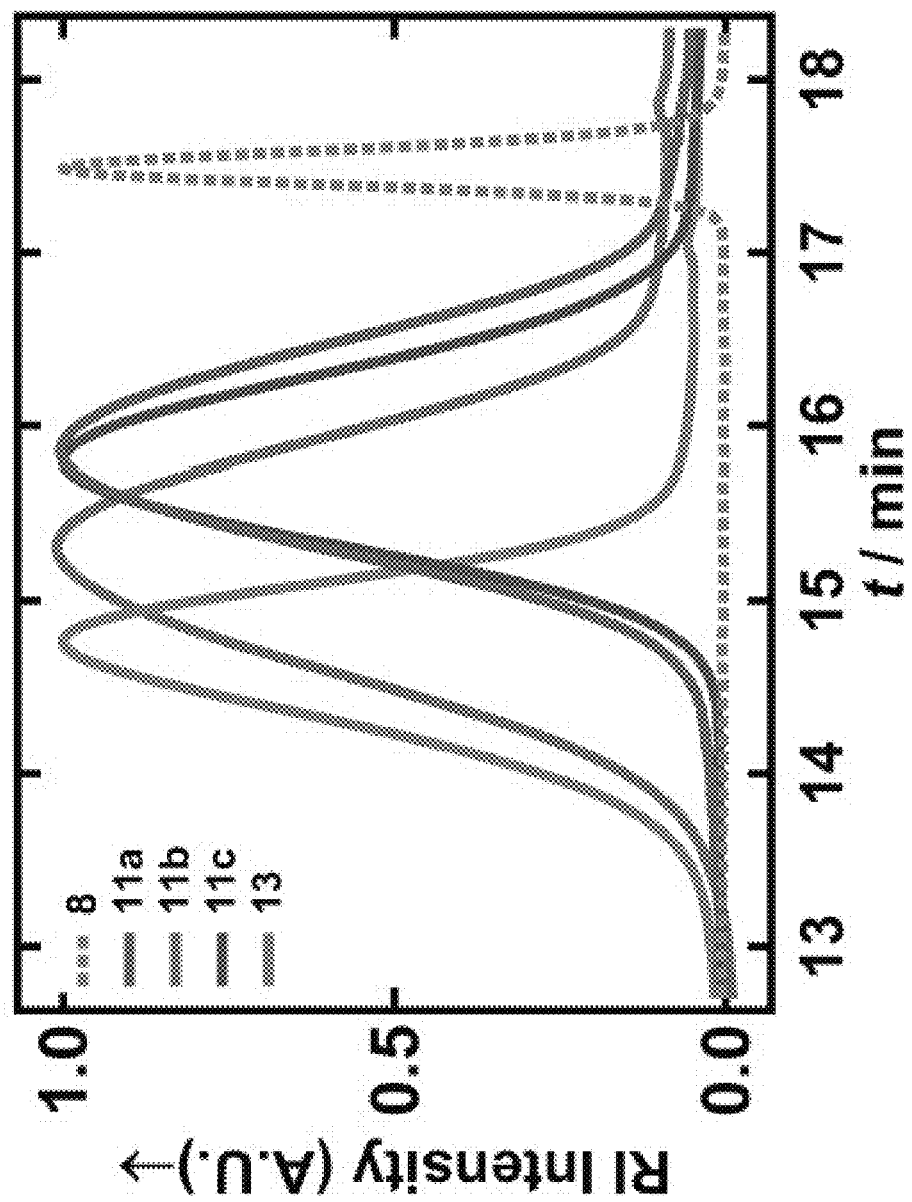
FIG. 33 provides SEC-RI chromatograms for polybenzoquinolines in accordance with embodiments of the invention.

Polybenzoquinoline 11a was subsequently processed and again characterized. The reaction was terminated by addition of phenylacetylene and purified the resulting material through sequential precipitation/chromatography. Then compound 11a was analyzed via SEC-RI with respect to calibration standards. The measurement yielded an Mn of 7840 g mol−1, an Mw of 10500 g mol−1, and a PDI of 1.34, corresponding to ~21 benzoquinoline subunits for purified compound 11a (FIG. 3 and Table 1). For comparison, the same measurement for monodisperse benzoquinoline model compound 8 yielded an Mn of 2110 g mol−1, an Mw of 2120 g mol−1, and a PDI of 1.01, reinforcing the accuracy of the analysis (FIG. 33 and Table 2, below). Notably, despite its aromatic character and crowded architecture, compound 11a was readily soluble in most common organic solvents, presumably due to a partially contorted geometry, as observed for the model compounds. The observations were consistent with the preparation of an extended polybenzoquinoline.

TABLE 2

Compound Properties

| Compound | $M_n$ [g mol$^{-1}$] | $M_w$ [g mol$^{-1}$] | PDI | N[b] |
|---|---|---|---|---|
| 8 | 2110 | 2120 | 1.01 | 5 |
| 11a | 7840 | 10500 | 1.34 | 21 |
| 11b | 15500 | 22300 | 1.44 | 25 |
| 11c | 8960 | 10900 | 1.22 | 22 |
| 13 | 29600 | 36200 | 1.22 | 60 |

Figure 34:
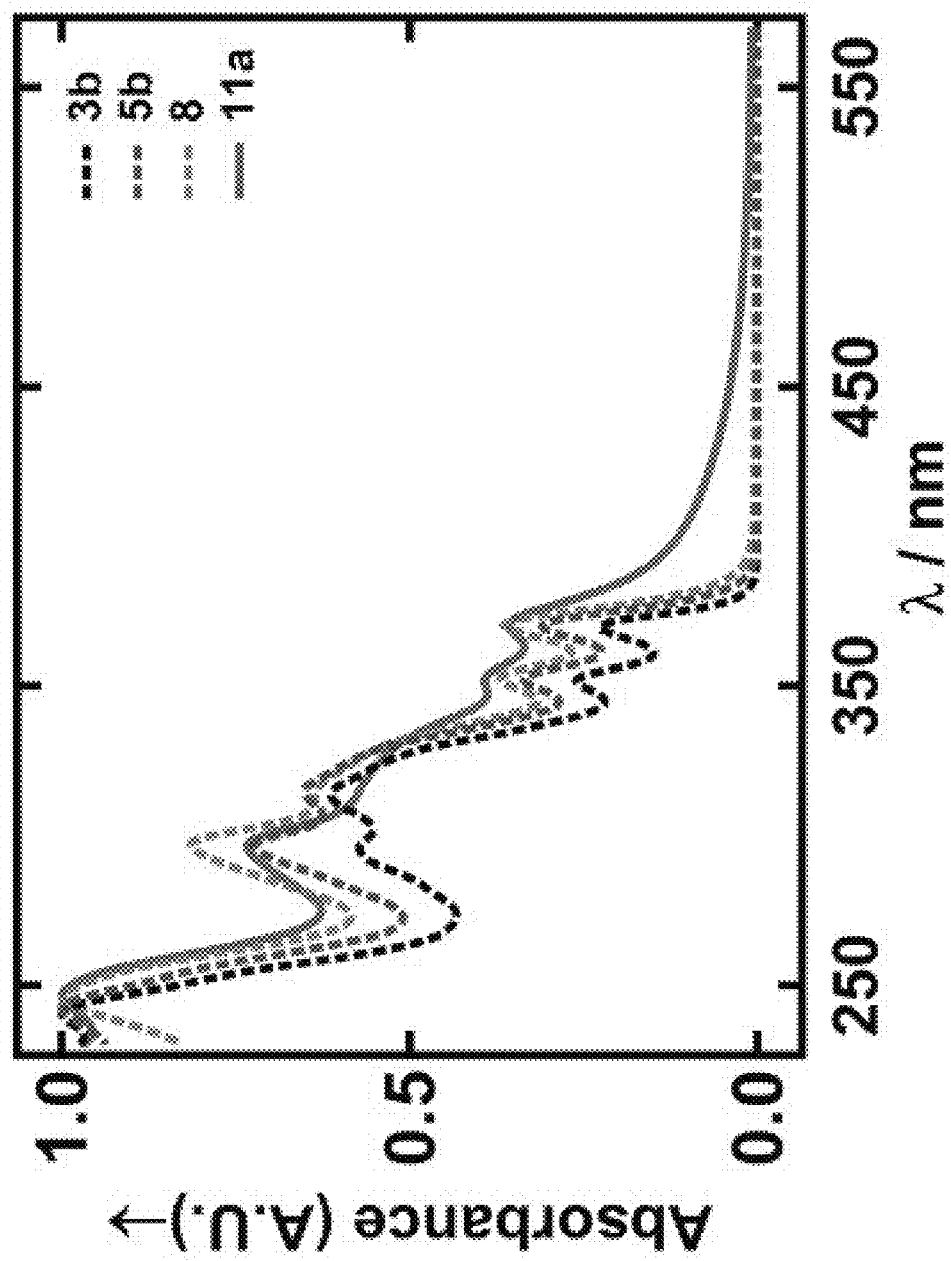
FIG. 34 provides UV-vis absorbance spectra for benzoquinoline compounds in accordance with embodiments of the invention.

Compounds 3b, 5b, 8, and 11a were further characterized with ultraviolet-visible (UV-vis) spectroscopy (FIG. 34). The spectra obtained for compounds 3b, 5b, and 8 showed characteristic absorbance peaks with maxima at nearly identical positions of 297 nm, 314 nm, 352 nm, and 370 nm. By comparison, the spectrum obtained for 11a featured broadened absorption maxima at similar positions and an onset of absorption that was red-shifted from ~380 nm to ~450 nm. Together, these measurements corroborated the formation of an extended polybenzoquinoline system for compound 11a.

To demonstrate that the polymerization strategy was modular and capable of accommodating different peripheral substituents the reaction conditions already validated for the synthesis of compound 10a was utilized to prepare monomers 10b and 10c, which incorporated branched alkyl chain and fluorine substituents, respectively (FIG. 9A). These conditions were then used similar to those developed for the synthesis of compounds 3b, 5b, 8, and 11a to furnish polybenzoquinolines 11b and 11c from monomers 10b and 10c, respectively (FIG. 9A). Standard purification and analysis procedures yielded the data shown in FIG. 33 and Table 2 for compounds 11b and 11c, confirming the success of the polymerization reactions. The preparation of distinct polybenzoquinolines under similar reaction conditions underscored the potential general scope of the approach.

Finally, the polymerization strategy was applied to the preparation of an even longer, sequence-variable polybenzoquinoline macromolecule. The procedure was slightly modified to convert 3b into bifunctional monomer 12 in four steps (FIG. 9B). The design of 12 incorporated the requisite alkyne and aldimine functional groups, an expanded aromatic core containing an additional benzoquinoline subunit, and alternating linear and branched alkyl side chains. Polymerization of 12 under standard reaction conditions furnished polybenzoquinoline 13. Per the SEC-RI measurement, this polymer featured an Mn of 29600 g mol$^{-1}$, an Mw of 36200 g mol$^{-1}$, and a PDI of 1.22, corresponding to ~60 repeating main chain benzoquinoline subunits (FIG. 33 and Table 2). Moreover, despite its increased size relative to compounds 11a-11c, and 13 exhibited good solubility in common organic solvents. Overall, these findings demonstrated the potential modularity of the approach, portending favorably for the synthesis of polybenzoquinoline-based graphene nanoribbon precursors with tunable sequence contexts.

Example 4

Crowded Benzoquinolines

A model 2,4,6-substituted benzoquinoline 3a is first synthesized via the Lewis acid-promoted Povarov reaction, as illustrated in FIG. 10. Thus, an aldimine precursor 1a was first prepared from commercially available starting materials (4-bromonaphylamine and octyl benzaldehyde) through a known literature protocol. To furnish 3a. A variety of Lewis acid promoters were screened for the cycloaddition of naphthyl alkyne 2 to aldimine 1a (FIG. 11); here, the sacrificial oxidant chloranil was included to ensure that compound 3a was fully aromatized. Although several Lewis acids (entries 1 to 4 in FIG. 11) resulted in modest yields for compound 3a, good yields and regioselectivity were obtained for AgOTf (67%), ZnCl2 (75%), and $BF_3 \cdot OEt_2$ (83%) (entries 6-8 in FIG. 11). Based on these observations, $BF_3 \cdot OEt_2$ was selected as the most promising Lewis acid for the subsequent experiments.

Having determined the optimal reaction conditions for the regioselective production of benzoquinoline 3a, the scope of the reaction was determined. Therefore different commercially available aldehyde derivatives were used to prepare distinct aldimines 1b-1i. Each of these aldimines was coupled with alkyne 2 to furnish regioisomerically pure 4,6-substituted benzoquinolines 3b-3i, as confirmed by 1H and 13C nuclear magnetic resonance (NMR) spectroscopy. Notably, the reaction conditions readily enabled the preparation of benzoquinolines featuring both electron withdrawing (entries 8, 9, 10, and 12 in FIG. 11) and electron donating (entry 15 in FIG. 11) substituents in good yields of >65%. Moreover, the protocol was capable of accommodating sterically hindered aldimines featuring ortho substituents on their pendant phenyl rings (entries 8 and 13 in FIG. 11), with little deleterious effect on the yields. Finally, it was discovered that the conditions could even accommodate aliphatic substituents (entry 14 in FIG. 11). Together, the above observations underscored the general applicability of the overall procedure for the production of varied crowded benzoquinolines.

Figure 35:
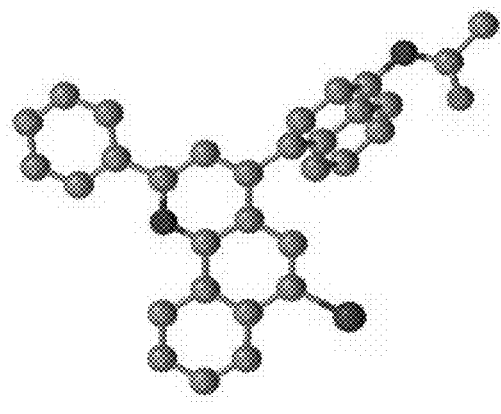
FIGS. 35A and 35B provide X-ray crystal structures for: A) an aldimine; and B) a benzoquinoline in accordance with embodiments of the invention.
Figure 35:
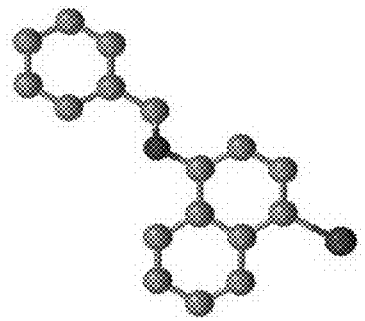

With the compounds in hand, insight into their absolute configurations was determined. Thus, the solid-state structures obtained were analyzed and compared for aldimine 1a and benzoquinoline 3e with standard X-ray crystallography techniques (FIG. 35). For aldimine 1a, it was found that the pendant phenyl ring was only slightly out of plane with the naphthyl system (FIG. 35A). Thus, pi-conjugation along the imine backbone appeared to be maintained. For benzoquinoline 3e, it was found that there was a small dihedral angle of ~15° between the pendant phenyl ring and the newly formed benzoquinoline system (FIG. 35B). Moreover, the crystal structure further confirmed the regioselectivity of the general reaction conditions (FIG. 35B). These crystallographic studies provided additional confirmation for the identity of the molecules.

Figure 36:
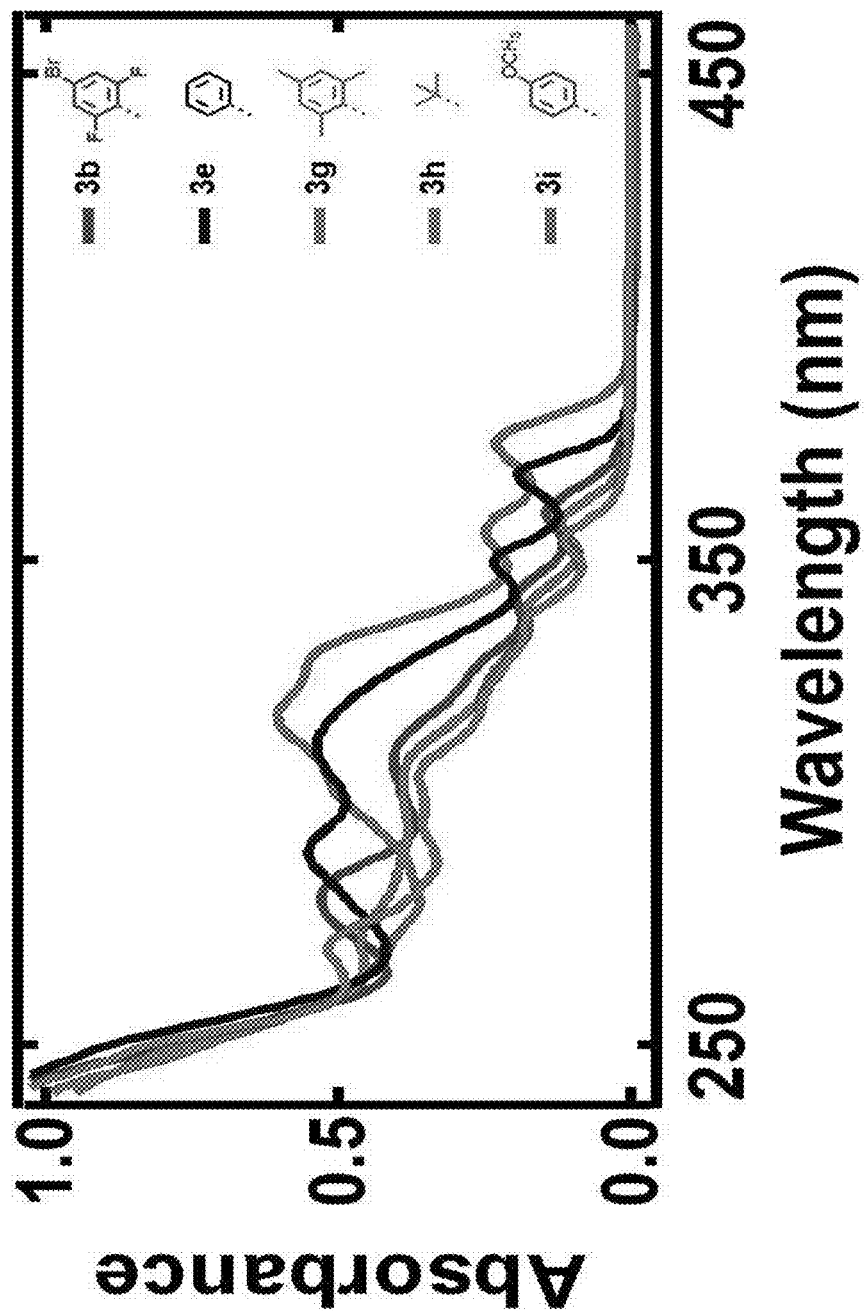
FIG. 36 provides UV-vis absorbance spectra for benzoquinoline model compounds in accordance with embodiments of the invention.

Next the electronic properties of benzoquinolines 3a-3i were investigated with UV-vis spectroscopy. As a specific example, the spectrum measured for compound 3e featured absorption peaks with maxima at 224 nm, 240 nm, 295 nm, 313 nm, 351 nm, and 370 nm (FIG. 36). This spectrum also differed somewhat from the spectrum of the benzo[h]quinoline core due to the presence of additional and/or red-shifted peaks; the difference could be readily rationalized by considering the aromatic substituents and expanded pi-conjugated system of 3e (relative to the benzo[h]quinoline). In general, the spectra of the benzoquinoline compounds all featured clusters of peaks at 220-300 nm and 300-375 nm but were blue- or red-shifted with respect to one another, as illustrated for compounds 3b, 3e, 3g, 3h, and 3i (FIG. 36). Overall, the spectra of the compounds were qualitatively quite similar.

When analyzing the molecules' spectroscopic properties, the spectra of compounds 3b and 3g were both substantially blue shifted with respect to that of compound 3e, and even generally resembled the spectrum of compound 3h (FIG. 36). Indeed, based only on a straightforward analysis of electron withdrawing and electron donating groups, one might expect a change in the positions of the HOMO and LUMO levels for halogen-substituted compound 3b and methyl-substituted compound 3g, but not necessarily a dramatic change in their spectra and HOMO-LUMO gap (all with respect to the spectrum of unsubstituted 3e). Here, based on the solid state structure of compound 3e in FIG. 35B, it is hypothesized that steric interactions between the crowded benzoquinoline core and the 2,6 substituents of the pendant phenyl rings of compounds 3b and 3g increased the dihedral angle between the two systems, twisting them out of co-planarity. This effect would decouple the phenyl and benzoquinoline aromatic systems and reduce the overall size of the pi-conjugated framework for compounds 3b and 3g, inducing the observed blue shifts in the spectra.

To provide theoretical validation for the hypothesis, DFT calculations were performed for all of the crowded 2,4,6-substituted benzoquinolines. As illustrative examples, FIG. 12 shows the chemical structures and corresponding HOMO and LUMO isosurface plots for compounds 3b, 3e, 3g, 3h, and 3i. First, it is found that the orientation of the naphthyl substituent relative to the benzoquinoline core was similar for these molecules, with a typical dihedral angle of ~74°. This observation indicated that the naphthyl moiety likely played a minor role in the unexpected blue shift observed for compounds 3b and 3g. Second, it is found that the dihedral angle between the pendant phenyl ring and benzoquinoline core for compounds 3b, 3e, 3g, and 3i could be roughly correlated with the localization of the HOMO and LUMO (FIG. 12). Indeed, these molecular orbitals were more likely to encompass the pendant phenyl ring for compounds 3b and 3e, than for compounds 3g and 3i. Moreover, the HOMO and LUMO orbitals of compound 3g resembled those of compound 3h, indicating that the pendant phenyl of compound 3g was electronically decoupled from its benzoquinoline core (FIG. 12). Overall, this analysis indicated that steric effects play an important role in dictating the electronic properties of the compounds.

Example 5

Molecular Segments and Graphene Nanoribbons

Rubicene and tetrabenzopentacene were synthesized via the Povarov reaction, as illustrated in FIG. 14A. To prepare compounds 3 and 5 in FIG. 14A, bis(aldimine) 1 was first formed through a known literature procedure. Subsequently, compound 2 was obtained by reacting the bis(aldimine) 1 with phenylacetylene in the presence of $BF_3 \cdot OEt_2$ as a Lewis acid mediator and chloranil as an oxidant, and compound 4 was obtained by reacting bis(aldimine) 1 with 1-ethynylnaphthalene in the presence of $FeCl_3$ as Lewis acid and a TEMPO oxonium salt as an oxidant. Next, compound 3 was synthesized by using the palladium-catalyzed Heck reaction to form intramolecular C—C bonds between the acene core and pendant phenyls of compound 2. In an analogous approach, compound 5 was synthesized by using base-mediated cyclodehydrogenation to form intramolecular C—C bonds between the acene core and pendant naphthyls of compound 4. This pathway furnished desired products 3 and 5 in moderate yields.

Rubicene 9 and tetrabenzopentacene 10 were also synthesized via the Povarov reaction, as illustrated in FIG. 14B. To obtain compounds 9 and 10 (FIG. 14B), a bis(alkyne) 6 is first prepared. Then aldimine 7 is formed and reacted with bis(alkyne) 6, again in the presence of a Lewis acid mediator and an oxidant, producing anthracene intermediate 8. Rubicene (compound 9 in FIG. 14B) was prepared using the palladium-catalyzed Heck reaction to form intramolecular C—C bonds between the acene core and pendant quinolines of anthracene precursor 8. In an analogous approach tetrabenzopentacene compound 10 was synthesized using base-mediated cyclodehydrogenation to form intramolecular C—C bonds between the acene core and pendant quinolines of anthracene precursor 8.

Figure 37:
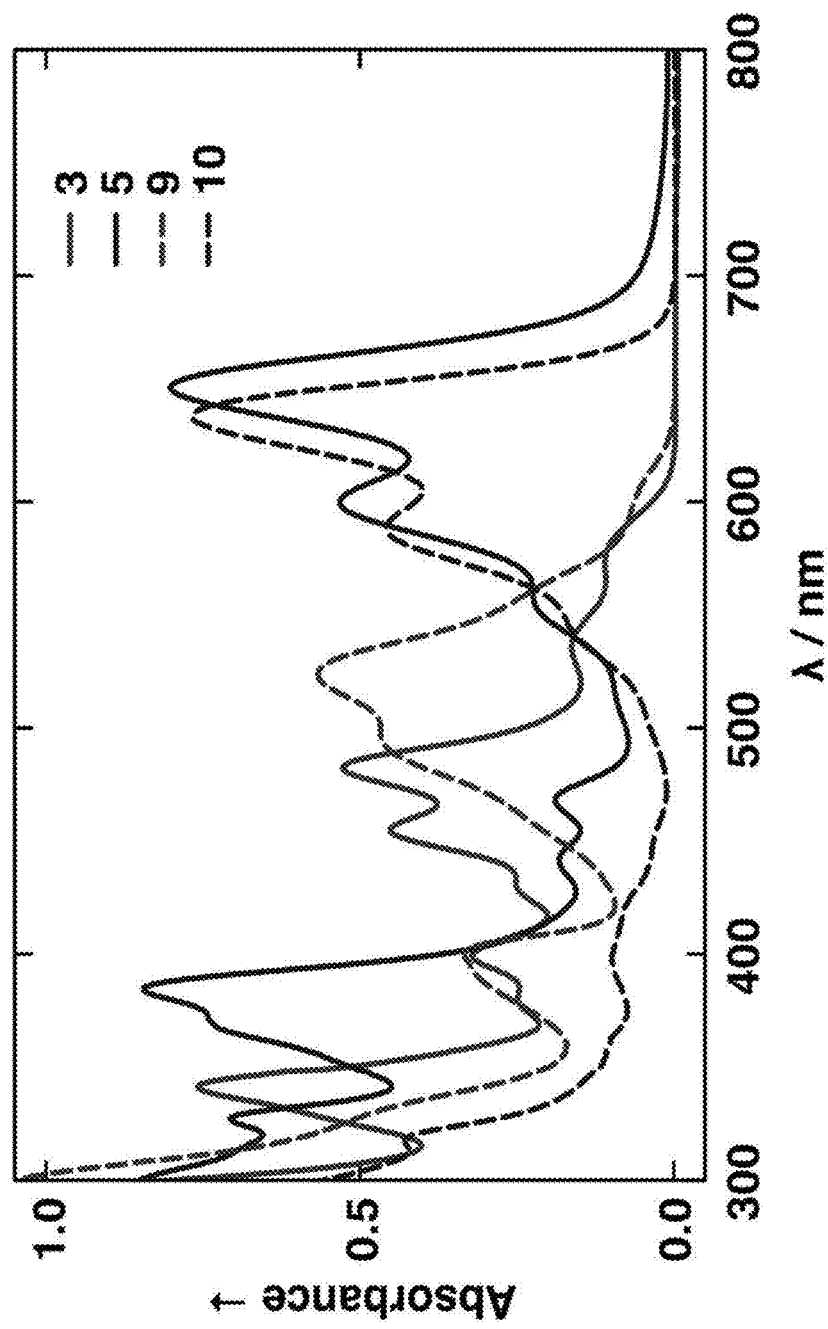
FIG. 37 provides UV-vis absorption spectra for rubicene and tetrabenzopentacene compounds in accordance with embodiments of the invention.

The electronic properties of compounds 3, 5, 9, and 10 were investigated with ultraviolet-visible (UV/Vis) spectroscopy. For compounds 3 and 9, it was found that the spectra generally resembled those reported for rubicene and its derivatives. For example, the spectrum obtained for compound 3 featured characteristic clusters of absorption peaks at 341 nm, 399 nm, and 483 nm (FIG. 37). By comparison, the spectrum obtained for compound 9 was broadened and red-shifted (presumably due to the molecule's expanded aromatic system), with prominent absorption peaks at 400 nm and 524 nm (FIG. 37). Likewise, it is found that the spectra for compounds 5 and 10 were similar to the classic ones reported for tetrabenzopentacene and other pentacene derivatives. The spectrum obtained for compound 5 featured a cluster of three characteristic absorption peaks at 555 nm, 600 nm, and 650 nm (FIG. 37). The spectrum obtained for compound 10 was slightly blue-shifted but comparable to compound 5, with absorption peaks at 543 nm, 588 nm, and 638 nm (FIG. 37). Overall, these findings indicated that the electronic properties of the nitrogen-doped rubicene and tetrabenzopentacene variants generally resembled those of their all-carbon parent molecules.

Figure 38:
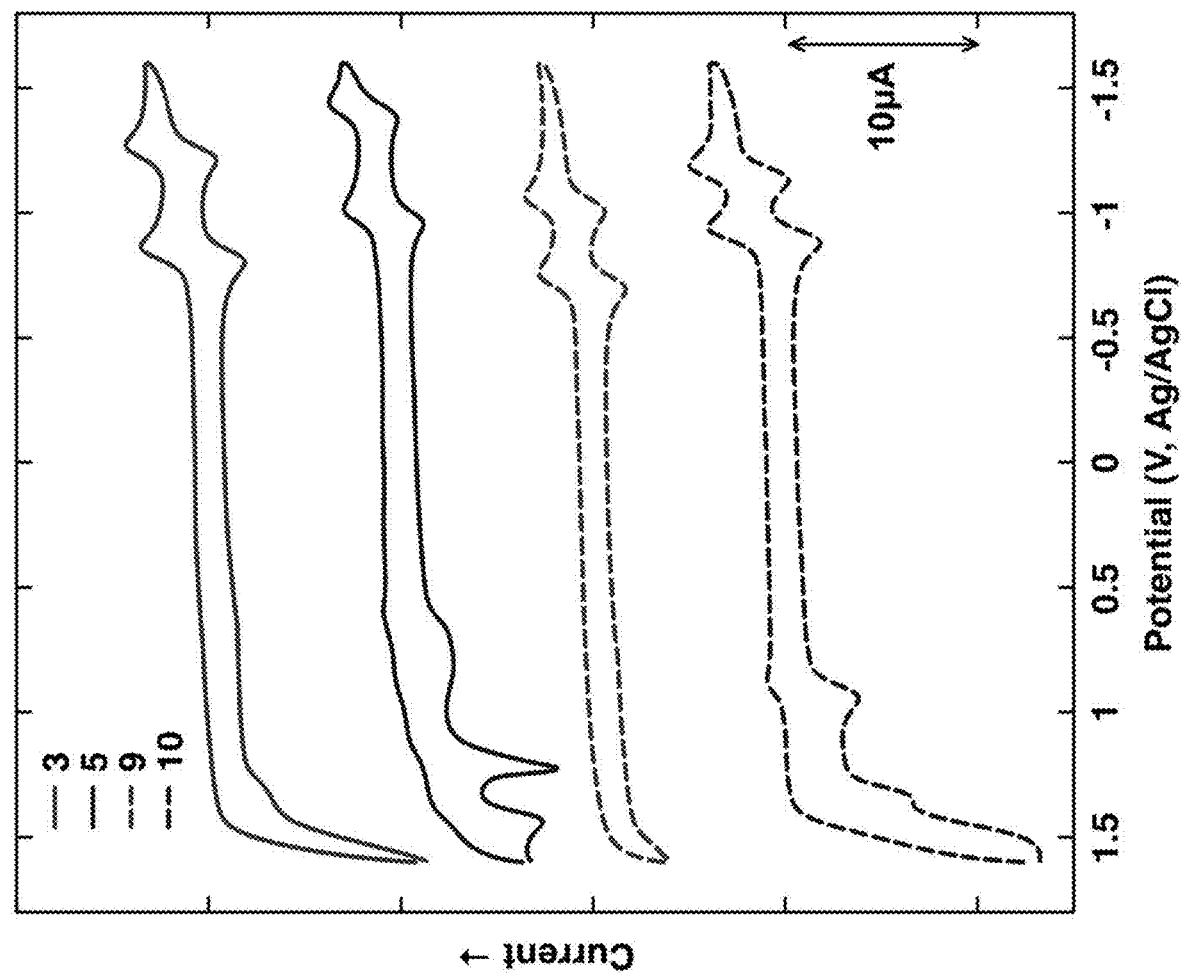
FIG. 38 provides cyclic voltammograms for rubicene and tetrabenzopentacene compounds in accordance with embodiments of the invention.

The electrochemical behavior of compounds 3, 5, 9, and 10 were next investigated with cyclic voltammetry (CV) (FIG. 38). Interestingly, it was found that compounds 3 and 9 were easier to reduce but more difficult to oxidize compared to previously reported all-carbon rubicene derivatives (Table 3, below). For compound 3, the voltammogram featured two quasi-reversible redox couples at reductive potentials of −0.83 V vs. Ag/AgCl and −1.24 V vs. Ag/AgCl, but no obvious reversible redox couples at oxidative potentials. For compound 9, the voltammogram was similar, with two quasi-reversible redox couples at reductive potentials of −0.73 V vs. Ag/AgCl and −1.04 V vs. Ag/AgCl, and, again, no obvious reversible redox couples at oxidative potentials. Likewise, it was found that compounds 5 and 10 were easier to reduce but more difficult to oxidize than previously reported all-carbon pentacene derivatives. For compound 5, the voltammogram featured two quasi-reversible redox couples at reductive potentials of −0.99 V vs. Ag/AgCl and −1.41 V vs. Ag/AgCl, as well as one quasi-reversible redox couple at oxidative potentials of 0.70 V vs. Ag/AgCl. For compound 10, the voltammogram was similar, with two quasi-reversible redox couples at reductive potentials of −0.91 V vs. Ag/AgCl and −1.16 V vs. Ag/AgCl, as well as one quasi-reversible redox couple at oxidative potentials of 0.91 V vs. Ag/AgCl. Overall, these findings indicated that the incorporation of nitrogen heteroatoms enhanced the molecules' electron accepting properties, in agreement with literature precedent for various heteroacenes.

TABLE 3

Molecular Orbital Energy Summary

| Compound | HOMO [eV] | LUMO [eV] | HOMO$^{(DFT)}$ [eV] | LUMO$^{(DFT)}$ [eV] |
|---|---|---|---|---|
| Rubicene | −5.51 | −3.40 | −5.54 | −2.80 |
| 3 | −5.71 | −3.68 | −5.60 | −3.01 |
| 9 | −5.74 | −3.77 | −5.80 | −3.25 |
| Tetrabenzopentacene | — | — | −4.71 | −2.71 |
| 5 | −4.94 | −3.50 | −4.89 | −2.87 |
| 10 | −5.23 | −3.58 | −5.13 | −3.11 |

Figure 28A:
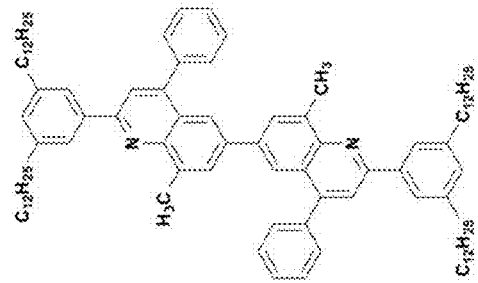
Figure 28B:
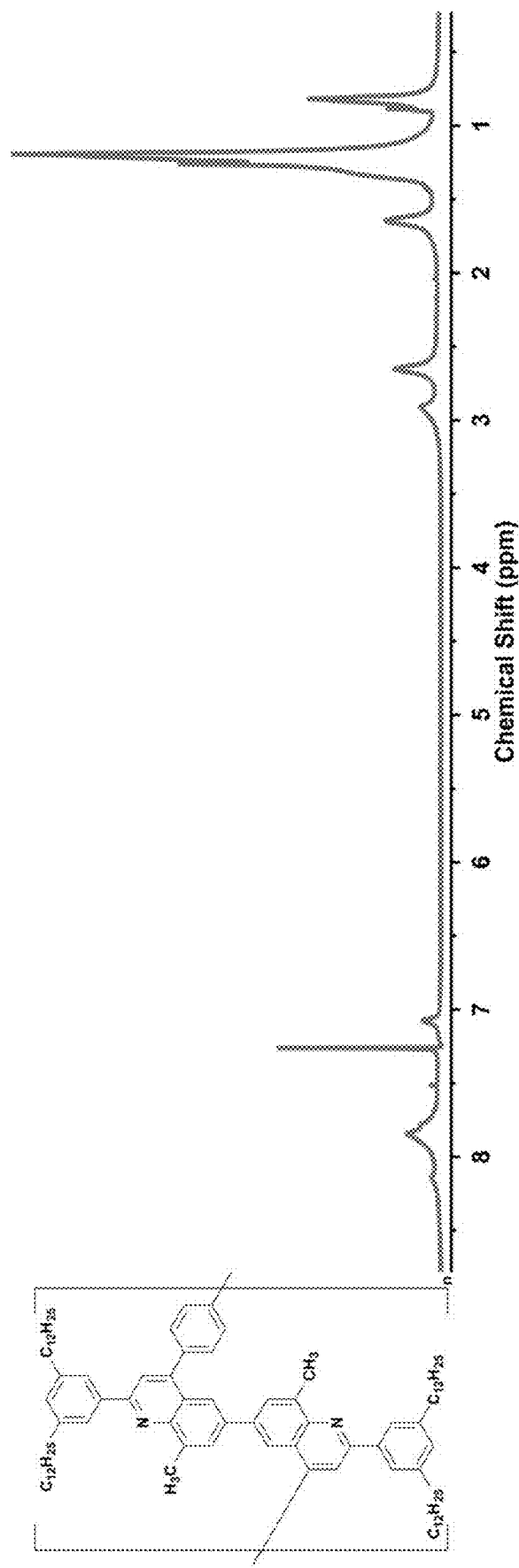
Figure 39:
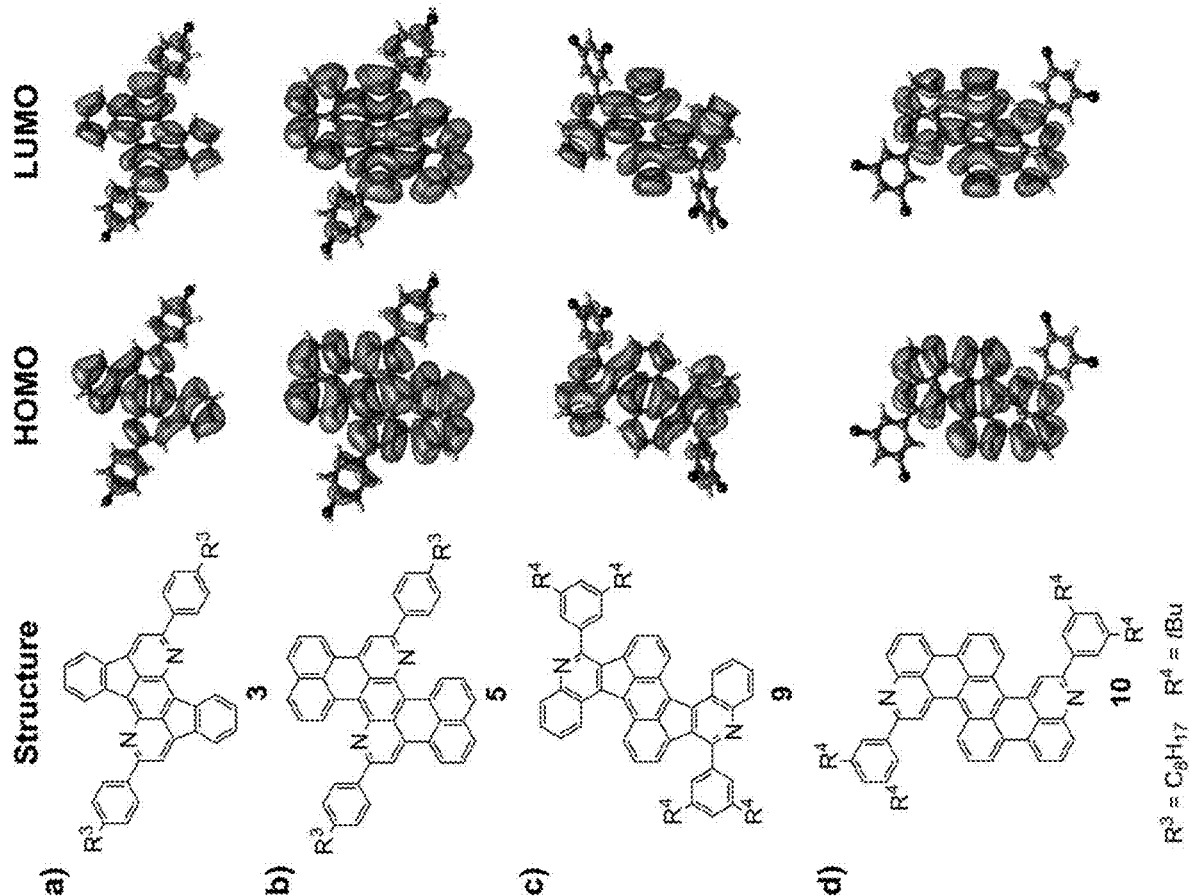
FIGS. 39A to 39D provide the chemical structure, HOMO and LUMO for rubicenes and tetrabenzopentacene compounds in accordance with embodiments of the invention.

To gain further insight into the electronic structure of the molecules, density functional theory (DFT) calculations were performed for compounds 3, 5, 9, and 10 (FIGS. 39A to 39D), as well as for their all-carbon analogues. From these calculations, the shapes and energies of the highest occupied molecular orbitals (HOMOs) and the lowest unoccupied molecular orbitals (LUMOs) were obtained for all six molecules (FIG. 39 and Table 3, below). It was thus possible to assign the redox couples observed with cyclic voltammetry for compounds 3, 5, 9, and 10 to the HOMO and LUMO, as appropriate (Table 1). The DFT calculations indicated that, regardless of the presence of heteroatoms, the HOMO and LUMO were similar in shape and localized on the aromatic core for both the three rubicenes and the three terabenzopentacenes. However, it was found that the energies of the theoretically-predicted HOMO and LUMO for all of the nitrogen-doped compounds were lowered with respect to their all-carbon parent molecules, as also suggested by the electrochemical measurements (FIG. 38 and Table 1). Notably, the electronic properties of the molecules appeared to be influenced by the precise location of the nitrogen dopants, with compound 9 featuring a lower lying LUMO and HOMO than compound 3, and compound 10 featuring a lower lying LUMO and HOMO than compound 5, again in agreement with the electrochemical measurements (FIG. 28 and Table 1). Overall, the theoretical calculations supported the experimental findings and implied that the molecules constitute exciting candidate n-type organic semiconductor materials.

INCORPORATION BY REFERENCE

All patents, patent applications, and publications cited in this specification are herein incorporated by reference in their entirety to the same extent as if each independent patent, patent application, or publication was specifically and individually indicated to be incorporated by reference.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method of producing bi-quinolines or polyquinolines comprising:
reacting a bifunctional aromatic aldimine with an aromatic mono- or bialkynyl in the presence of a Lewis acid mediator and an oxidant to produce the corresponding bi-quinoline or polyquinoline, wherein:
the bifunctional aromatic aldimine is of formula:

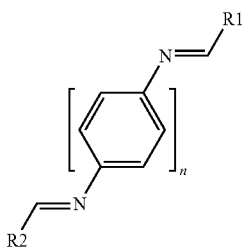

comprising:
a first aromatic core comprising aromatic or heteroaromatic rings,
wherein
n is a number of distinct rings and is an integer of at least 1, and
the first aromatic core is optionally substituted with one or more functionalities each independently selected from the group: a halogen, an alkyl, an alkoxy, an acetyl, an N-acetyl, an amine, an alkyl amine, a sulfide, or any combination thereof;
a first aldimine functionality immediately and covalently attached to the first aromatic core, wherein
R1 is an aromatic or heteroaromatic functionality optionally substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof; and
a second aldimine functionality immediately and covalently attached to the first aromatic core, wherein
R2 is one of the functionalities selected from the group of: R1, a substituted aromatic ring, an unsubstituted aromatic ring, a substituted heteroaromatic ring, and an unsubstituted heteroaromatic ring; and
the aromatic mono- or bialkynyl comprises a second aromatic core and one or two aromatic terminal alkyne functionalities respectively; and wherein
the first and the second aldimine functionalities of the bifunctional aromatic aldimine react with the one or two aromatic terminal alkyne functionalities of the aromatic mono- or bialkynyl to yield the corresponding bi-quinoline or polyquinoline comprising quinoline moieties incorporating the nitrogens of the first and the second aldimine functionalities.

2. The method of claim 1, wherein n is 2 such that the first aromatic core is a naphthyl and the quinoline moieties are benzoquinoline.

3. The method of claim 1, wherein n is 2 and the ring that does not bear the first aldimine functionality is heteroaromatic.

4. The method of claim 3, wherein the heteroaromatic ring is a pyridine-type and the quinoline moieties are of the phenanthroline variant.

5. The method of claim 2, wherein the first aldimine functionality is attached at position 1 of the naphthyl, and the naphthyl is further functionalized at position 8 with at least one of: aliphatic group, electron withdrawing group, electron donating group.

6. The method of claim 1, wherein n is at least 2 and some or all of the aromatic rings of the first aromatic core are linked at the 4 and 6 positions rather than fused, such that the aromaticity of the first aromatic core is maintained.

7. The method of claim 1, wherein the second aromatic core is a naphthyl moiety.

8. The method of claim 7, wherein the naphthyl moiety is substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof.

9. The method of claim 1, wherein both the aromatic monoalkynyl comprising one aromatic terminal alkyne functionality and the aromatic bialkynyl comprising two aromatic alkyne functionalities are used in the same reaction mixture to control the length of the polyquinolines.

10. A method of forming nitrogen-doped aromatic molecular segments or graphene nanoribbons comprising:
reacting a bifunctional aromatic aldimine with an aromatic mono- or bialkynyl in the presence of a Lewis acid mediator and an oxidant to produce the corresponding bi-quinoline or polyquinoline, and
forming intramolecular C—C bonds between aromatic and heteroaromatic moieties of the corresponding bi-quinoline or polyquinoline to form the corresponding nitrogen-doped molecular segment or graphene nanoribbon, wherein:
the bifunctional aromatic aldimine is of formula:

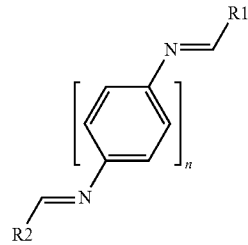

comprising:
a first aromatic core comprising aromatic or heteroaromatic rings,
wherein
n is a number of distinct rings and is an integer of at least 1, and
the first aromatic core is optionally substituted at any of its aromatic or heteroaromatic rings with one or more functionalities each independently selected from the group: a halogen, an alkyl, an alkoxy, an acetyl, an N-acetyl, an amine, an alkyl amine, a sulfide, or any combination thereof;

a first aldimine functionality immediately and covalently attached to the first aromatic core, wherein
R1 is an aromatic or heteroaromatic functionality optionally substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof; and
a second aldimine functionality immediately and covalently attached to the first aromatic core, wherein
R2 is one of the functionalities selected from the group of: R1, a substituted aromatic ring, an unsubstituted aromatic ring, a substituted heteroaromatic ring, and an unsubstituted heteroaromatic ring; and
the aromatic mono- or bialkynyl comprises a second aromatic core, and one or two aromatic terminal alkyne functionalities, respectively; and wherein
the first and the second aldimine functionalities of the bifunctional aromatic aldimine react with the one or two aromatic terminal alkyne functionalities of the aromatic mono- or bialkynyl to yield the corresponding bi-quinoline or polyquinoline comprising quinoline moieties incorporating the nitrogens of the first and the second aldimine functionalities.

11. The method of claim 10, wherein n is 1, the first aromatic core is a benzene additionally substituted with two Cl functionalities at positions 2 and 5, the second aldimine functionality is located at position 4, the aromatic monoalkynyl is phenylacetylene, and two intramolecular CC bonds are formed via Heck reaction such that the corresponding nitrogen-doped molecular segment or graphene nanoribbon is a rubicene nitrogen-doped molecular segment.

12. The method of claim 10, wherein n is 1, the first aromatic core is a benzene additionally substituted with two Cl functionalities at positions 2 and 5, the second aldimine functionality is located at position 4, the aromatic monoalkynyl is naphthyl alkyne, and two intramolecular C—C bonds are formed via base mediated cyclodehydrogenation reaction such that the corresponding nitrogen-doped molecular segment or graphene nanoribbon is a tetrabenzopentacene nitrogen-doped molecular segment.

13. The method of claim 10, wherein the aromatic bialkynyl is 1,5-dichloro-9,10-diethynylanthracene, and intramolecular C—C bonds are formed via Heck reaction.

14. The method of claim 10, wherein the aromatic bialkynyl is 1,5-dichloro-9,10-diethynylanthracene, and intramolecular C—C bonds are formed via base mediated cyclodehydrogenation reaction.

15. A bifunctional aromatic aldimine for producing quinolines, polyquinolines, nitrogen-doped aromatic molecular segments, and graphene nanoribbons according to:

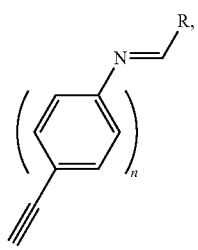

and comprising:
an aromatic core comprising aromatic or heteroaromatic rings, wherein
n is a number of distinct rings and is an integer of at least 1, and
the aromatic core is optionally substituted at any of its aromatic or heteroaromatic rings with one or more functionalities each independently selected from the group: a halogen, an alkyl, an alkoxy, an acetyl, an N-acetyl, an amine, an alkyl amine, a sulfide, or any combination thereof;
an aldimine functionality immediately and covalently attached to the aromatic core, wherein R is a substituted or unsubstituted aromatic or heteroaromatic ring; and
an aromatic terminal alkyne functionality immediately and covalently attached at any position of the aromatic core and capable of reacting with an aromatic aldimine in an aza-Diels Alder Povarov reaction.

16. The bifunctional aromatic aldimine of claim 15, wherein R is substituted with at least one functionality, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof.

17. The bifunctional aromatic aldimine of claim 16, wherein R has at least two substitutions.

18. The bifunctional aromatic aldimine of claim 15, wherein n is at least 2.

19. The bifunctional aromatic aldimine of claim 15, wherein n is 2 and the ring that does not bear the aldimine functionality is heteroaromatic.

20. The bifunctional aromatic aldimine of claim 15, wherein n is 2 and the ring that does not bear the aldimine functionality is further functionalized with at least one of: aliphatic group, electron withdrawing group, electron donating group.

21. The bifunctional aromatic aldimine of claim 15, wherein n is at least 2 and some or all of the aromatic rings of the aromatic core are linked at the 4 and 6 positions rather than fused, such that the aromaticity of the aromatic core is maintained.

22. A method of producing polyquinolines comprising:
reacting a bifunctional aromatic aldimine with itself in the presence of a Lewis acid mediator and an oxidant to produce the corresponding polyquinoline, wherein:
the bifunctional aromatic aldimine is of formula:

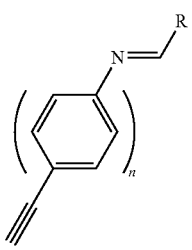

comprising:
an aromatic core comprising aromatic or heteroaromatic rings,
wherein
n is a number of distinct rings and is an integer of at least 1, and the aromatic core is optionally substituted at any of its aromatic or heteroaromatic rings with one or more functionalities each independently selected from the group: a halogen, an alkyl, an alkoxy, an acetyl, an N-acetyl, an amine, an alkyl amine, a sulfide, or any combination thereof;

an aldimine functionality immediately and covalently attached to the aromatic core, wherein R is an aromatic or heteroaromatic functionality optionally substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof; and an aromatic terminal alkyne functionality immediately and covalently attached at any position of the aromatic core; and wherein the aldimine functionality of one molecule of the bifunctional aromatic aldimine reacts with the aromatic terminal alkyne functionality of another molecule of the bifunctional aromatic aldimine to yield the corresponding polyquinoline comprising quinoline moieties incorporating the nitrogens of the aldimine functionalities.

23. The method of claim 22, wherein n is 2 such that the aromatic core is a naphthyl and the quinoline moieties are benzoquinoline.

24. The method of claim 22, wherein n is 2 and the ring that does not bear the aldimine functionality is heteroaromatic.

25. The method of claim 24, wherein the heteroaromatic ring is a pyridine-type the quinoline moieties are of the phenanthroline variant.

26. The method of claim 23, wherein the aldimine functionality is attached at position 1 of the naphthyl, and the naphthyl is further functionalized at position 8 with at least one functional group selected from the list: aliphatic group, electron withdrawing group, electron donating group.

27. The method of claim 22, wherein n is at least 2 and some or all of the aromatic rings of the aromatic core are linked at the 4 and 6 positions rather than fused, such that the aromaticity of the aromatic core is maintained.

28. The method of claim 22, wherein n is at least 2 and any ring that does not bear the aldimine functionality is further functionalized with at least one of: aliphatic group, electron withdrawing group, electron donating group.

29. The method of claim 22, wherein an altered aromatic aldimine is added to the reaction mixture to control the length of the polyquinolines, wherein the altered aromatic aldimine comprises all of the elements of the bifunctional aromatic aldimine except for one element chosen from the list: the aromatic terminal alkyne functionality or the aldimine functionality.

30. A method of forming nitrogen-doped graphene nanoribbons comprising:

reacting a bifunctional aromatic aldimine with itself in the presence of a Lewis acid mediator and an oxidant to produce the corresponding polyquinoline, and forming intramolecular C—C bonds between aromatic and heteroaromatic moieties of the corresponding polyquinoline to form the corresponding nitrogen-doped graphene nanoribbon, wherein:

the bifunctional aromatic aldimine is of formula:

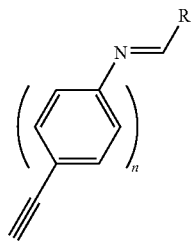

comprising:

an aromatic core comprising aromatic or heteroaromatic rings, wherein n is a number of distinct rings and is an integer of at least 1, and the aromatic core is optionally substituted at any of its aromatic or heteroaromatic rings with one or more functionalities each independently selected from the group: a halogen, an alkyl, an alkoxy, an acetyl, an N-acetyl, an amine, an alkyl amine, a sulfide, or any combination thereof;

an aldimine functionality immediately and covalently attached to the aromatic core, wherein R is an aromatic or heteroaromatic functionality optionally substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof; and an aromatic terminal alkyne functionality immediately and covalently attached to the aromatic core; and wherein the aldimine functionality of one molecule of the bifunctional aromatic aldimine reacts with the aromatic terminal alkyne functionality of another molecule of the bifunctional aromatic aldimine to yield the polyquinolines comprising quinoline moieties incorporating the nitrogens of the aldimine functionalities.

31. The method of claim 30, wherein the intramolecular C—C bonds are formed via cyclodehydrogenation.

32. The method of claim 30, wherein n is 2 such that the aromatic core is a naphthyl and the quinoline moieties are benzoquinoline.

33. The method of claim 32, wherein the substituent at position 2 of the quinoline moieties is disposed at the edge location of the corresponding nitrogen-doped graphene nanoribbon.

34. The method of claim 30, wherein the corresponding nitrogen-doped graphene nanoribbon is a nitrogen-doped N=7 armchair graphene nanoribbon.

35. The method of claim 34, wherein the concentration of nitrogen doping can vary from 7 to 14%.

36. The method of claim 30, wherein the corresponding polyquinoline is a polyquinoline with a plurality of quinolines interlinked at the 4 and 6 positions.

37. The method of claim 32, wherein the corresponding polyquinoline is a polybenzoquinoline with a plurality of benzoquinolines interlinked at the 4 and 6 positions.

38. A method of producing nitrogen-doped graphene segments comprising:

reacting an aromatic aldimine with an aromatic bialkynyl in the presence of a Lewis acid mediator and an oxidant to produce the corresponding biquinoline; and forming intramolecular C—C bonds between aromatic and heteroaromatic moieties of the corresponding biquinoline to form the corresponding nitrogen-doped graphene segment, wherein:

the aromatic aldimine is of formula:

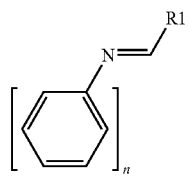

comprising:
   a first aromatic core comprising aromatic or heteroaromatic rings,
   wherein
      n is a number of distinct rings and is an integer of at least 1, and
      the first aromatic core is optionally substituted at any of its aromatic or heteroaromatic rings with one or more functionalities each independently selected from the group: a halogen, an alkyl, an alkoxy, an acetyl, an N-acetyl, an amine, an alkyl amine, a sulfide, or any combination thereof; and
   an aldimine functionality attached to the first aromatic core, wherein
      R is an aromatic or heteroaromatic functionality optionally substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof; and
the aromatic bialkynyl comprises a second aromatic core and two aromatic terminal alkyne functionalities; and wherein
the aldimine functionalities of two molecules of the aromatic aldimine react with the two aromatic terminal alkyne functionalities of one molecule of the aromatic bialkynyl to yield quinoline moieties incorporating the nitrogens of the aldimine functionalities.

39. The method of claim 38, wherein n is 2 such that the first aromatic core is a naphthyl and the quinoline moieties are benzoquinoline.

40. The method of claim 38, wherein n is 2 and the ring of the first aromatic core that does not bear the aldimine functionality is heteroaromatic.

41. The method of claim 40, wherein the heteroaromatic ring is a pyridine-type, and the quinoline moieties are of the phenanthroline variant.

42. The method of claim 39, wherein the aldimine functionality is attached at position 1 of the naphthyl, and the naphthyl is further functionalized at position 8 with at least one functional group selected from the list: aliphatic group, electron withdrawing group, electron donating group.

43. The method of claim 38, wherein n is at least 2 and some or all of the aromatic rings of the first aromatic core are linked at the 4 and 6 positions rather than fused, such that the aromaticity of the aromatic core is maintained.

44. The method of claim 38, wherein the second aromatic core is a naphthyl moiety.

45. The method of claim 44, wherein the naphthyl moiety is substituted with one or more substituents, each independently selected from the group: a halogen, an alkyl, an alkoxy, an acetyl, an N-acetyl, an amine, an alkyl amine, a sulfide, a nitrate, a nitrile, another electron withdrawing or electron donating functionality, or any combination thereof.

46. The method of claim 38, wherein n is 1, the aromatic alkynyl is 1,5-dichloro-9,10-diethynylanthracene, and two intramolecular C—C bonds are formed via Heck reaction such that the corresponding nitrogen-doped graphene segment is a rubicene nitrogen-doped molecular segment.

47. The method of claim 38, wherein n is 1, the aromatic alkynyl is 1,5-dichloro-9,10-diethynylanthracene, and two intramolecular C—C bonds are formed via base mediated cyclodehydrogenation reaction such that the corresponding nitrogen-doped graphene segment is a tetrabenzopentacene nitrogen-doped molecular segment.

\* \* \* \* \*